(12) United States Patent
Kaleko et al.

(10) Patent No.: US 10,584,326 B2
(45) Date of Patent: *Mar. 10, 2020

(54) BETA-LACTAMASES WITH IMPROVED PROPERTIES FOR THERAPY

(71) Applicant: Synthetic Biologics, Inc., Rockville, MD (US)

(72) Inventors: Michael Kaleko, Rockville, MD (US); Sheila Connelly, Rockville, MD (US)

(73) Assignee: Synthetic Biologics, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,411

(22) Filed: May 16, 2019

(65) Prior Publication Data

US 2020/0017844 A1 Jan. 16, 2020

Related U.S. Application Data

(63) Continuation of application No. 16/112,283, filed on Aug. 24, 2018, now Pat. No. 10,336,995, which is a continuation of application No. 15/993,159, filed on May 30, 2018, now Pat. No. 10,087,433, which is a continuation of application No. 15/674,177, filed on Aug. 10, 2017, now Pat. No. 10,011,824, which is a continuation of application No. 15/611,881, filed on Jun. 2, 2017, now Pat. No. 9,783,797, which is a continuation of application No. 15/245,517, filed on Aug. 24, 2016, now Pat. No. 9,695,409, which is a continuation of application No. 15/200,508, filed on Jul. 1, 2016, now Pat. No. 9,464,280, which is a continuation of application No. 15/160,669, filed on May 20, 2016, now Pat. No. 9,404,103, which is a continuation of application No. 15/019,474, filed on Feb. 9, 2016, now Pat. No. 9,376,673, which is a continuation of application No. 14/689,877, filed on Apr. 17, 2015, now Pat. No. 9,290,754.

(60) Provisional application No. 62/046,627, filed on Sep. 5, 2014, provisional application No. 61/980,844, filed on Apr. 17, 2014.

(51) Int. Cl.
| | | |
|---|---|---|
| *C12N 9/86* | (2006.01) | |
| *A61K 38/50* | (2006.01) | |
| *A61K 9/00* | (2006.01) | |
| *A61K 45/06* | (2006.01) | |
| *A61K 31/546* | (2006.01) | |
| *A61K 38/00* | (2006.01) | |

(52) U.S. Cl.
CPC ............ *C12N 9/86* (2013.01); *A61K 9/0053* (2013.01); *A61K 31/546* (2013.01); *A61K 38/50* (2013.01); *A61K 45/06* (2013.01); *C12Y 305/02006* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2,890,986 | A | 6/1959 | Kraut et al. |
| 2,941,995 | A | 6/1960 | Doyle et al. |
| 2,982,696 | A | 5/1961 | Puetzer et al. |
| 3,070,511 | A | 12/1962 | Weitnauer |
| 3,150,059 | A | 9/1964 | Kleinschmidt et al. |
| 3,239,394 | A | 3/1966 | Walton |
| 3,488,729 | A | 1/1970 | Chauvette et al. |
| 3,499,909 | A | 3/1970 | Weissenburger et al. |
| 5,607,671 | A | 3/1997 | Heino |
| 7,319,030 | B2 | 1/2008 | Koski et al. |
| 7,989,192 | B2 | 8/2011 | Kaariainen et al. |
| 8,894,994 | B2 | 11/2014 | Koski et al. |
| 9,034,602 | B2 | 5/2015 | Koski et al. |
| 2004/0248279 | A1 | 12/2004 | Sawada et al. |
| 2005/0158843 | A1 | 7/2005 | Koski et al. |
| 2005/0249716 | A1 | 11/2005 | Bourgeois et al. |
| 2007/0161040 | A1 | 7/2007 | Giannotta et al. |
| 2009/0181004 | A1 | 7/2009 | Kaariainen et al. |
| 2009/0311234 | A1 | 12/2009 | Koski et al. |
| 2013/0216622 | A1 | 8/2013 | Koski et al. |
| 2013/0338043 | A1* | 12/2013 | Firnberg ............... C07H 21/04 506/26 |
| 2015/0056178 | A1 | 2/2015 | Koski et al. |

FOREIGN PATENT DOCUMENTS

| | | |
|---|---|---|
| EP | 0384559 | 8/1990 |
| EP | 0420600 | 4/1991 |
| EP | 0420600 | 11/1992 |
| EP | 1564286 | 8/2005 |
| FI | 59265 | 3/1981 |
| FI | 880017 | 7/1988 |
| GB | 1241844 | 8/1971 |
| GB | 1463513 | 2/1977 |

(Continued)

OTHER PUBLICATIONS

Westphal et al., "Assessment of Biliary Excretion of Piperacilin-Tazobactam in Humans," Antimicrobial Agents and Chemotherapy, Aug. 1997, vol. 41, No. 8, pp. 1636-1640.

Whisstock et al., "Prediction of protein function from protein sequence," Q. Rev. Biophysics., 2003, vol. 36 (3):307-340.

Wildfeuer et al., "Pharmacokinetics of Sulbactam and Ampicillin Intravenously Applied in Combination to Healthy Volunteers and Patients", Arzneimittei-Forschung, 1988, vol. 38, No. 11, pp. 1640-1643.

Wishart et al., "A single mutation converts a novel phosphotyrosine binding domain into a dual-specificity phosphatase," J. Biol. Chem., 1995, vol. 270(45): 26782-26785.

(Continued)

*Primary Examiner* — Suzanne M Noakes

(74) *Attorney, Agent, or Firm* — Morgan, Lewis & Bockius LLP

(57) ABSTRACT

This invention relates to, in part, compositions of beta-lactamases and methods of using these enzymes in, for example, gastrointestinal tract (GI tract) disorders such as *C. difficile* infection (CDI).

18 Claims, 8 Drawing Sheets

Specification includes a Sequence Listing.

(56) References Cited

FOREIGN PATENT DOCUMENTS

| GB | 2199582 | 7/1998 |
|---|---|---|
| WO | 93/13795 | 7/1993 |
| WO | 97/03185 | 1/1997 |
| WO | 88/07865 | 10/1998 |
| WO | 03/040352 | 5/2003 |
| WO | 2004/016248 | 2/2004 |
| WO | 2005/078075 | 8/2005 |
| WO | 2006/122835 | 11/2006 |
| WO | 2007/147945 | 12/2007 |
| WO | 2008/065247 | 6/2008 |
| WO | 2011/148041 | 12/2011 |

OTHER PUBLICATIONS

Witkowski et al., "Conversion of .beta.-ketoacyl synthase to a Malonyl Decarboxylase by replacement of the active cysteine with glutamine," Biochemistry, 1999, vol. 38: 11643-11650.
Hata et al., "Substrate Deacylation Mechanisms of Serine-.beta.-lactamases," Biol. Pharm. Bull. 29:2151-2159 (2006).
Illing et al., "Use of integrational plasmid excision to identify cellular localization of gene expression during sporulation in Bacillus subtilis," J. Bacteriol. 172(12):6937-6941 (1990).
Leung et al., Site-directed mutagenesis of beta-lactamase I: role of Glu-166. Biochem J, May 1, 1994, vol. 299, Pt 3, pp. 671-678.
2BLM_A, PBD Accession No. 2BLM_A, Chain A, Beta-Lactamase of Bacillus Licheniformis 749(Slash)c at 2 Angstroins Resolution, Oct. 10, 2012 [online]. [Retrieved on Sep. 30, 2015]. Retrieved from the internet: <URL: http://www.ncbi.nlm.nih.gov/protein/2BLM_A> Entire document.
WP020449992, NCBI Reference Sequence: WP_020449992.1, beta-lactamase precursor [Bacillus licheniformis], Jul. 7, 2013 [online]. [Retrieved on Sep. 30, 2015]. Retrieved from the internet: <URL: http://www.ncbi.nlm.nih.gov/protein/521285724?sat=21&satkey=12563659> Entire document.
WP023857755, NCBI Reference Sequence: WP_023857755.1, beta-lactamase [Bacillus sp. CPSM8], Dec. 11, 2013 [online]. [Retrieved on Sep. 30, 2015]. Retrieved from the internet: <URL: http://www.ncbi.nlm.nih.gov/protein/564754507?sat=18&satkey=22477712> Entire document.
Altschul et al., "Gapped BLAST and PSI-BLAST: A New Generation of Protein Database Search Programs," Nucleic Acids Research, 1997, vol. 25, No. 17, pp. 3389-3402.
Ambler, "The structure of .beta.-lactamases," Phil. Trans. R. Soc. Lond. B 289: 321-331 (1980).
Ambler et al., "A Standard Numbering Scheme for the Class A Beta-Lactamases," Biochem. J., 1991, 276, pp. 269-272.
Bonnet, "Growing Group of Extended-Spectrum .beta.-Lactamases: the C T X-M Enzymes," Antimicrob. Agents Chemother. 48(1):1-14 (2004).
Bonomo et al., ".beta.-Lactamase mutations far from the active site influence inhibitor binding," Biochim. Biophys. Acta 1247:121-125 (1995).
Brogard et al., "Biliary Elimination of Ticarcillin Plus Clavulanic Acid (Ciaventin.RTM.)," Experimental and Clinical Study, International Journal of Clinical Pharmacology, Therapy and Toxicology, 1989, vol. 27, No. 3, pp. 135-144.
Broun et al., "Catalytic plasticity of fatty acid modification enzymes underlying chemical diversity of plant lipids," Science 1998, vol. 282: 1315-1317.
Bush, "Metallo-.beta.-Lactamases: A Class Apart," Clinical Infectious Diseases, 1998; 27(Suppl 1):S48-53.
Bush et al., "A Functional Classification Scheme for .beta.-Lactamases and Its Correlation with Molecular Structure," Antimicrobial Agents and Chemotherapy, Jun. 1995, vol. 39, No. 6, pp. 1211-1233.
Canica et al., "Phenotypic Study of Resistance of .beta.Lactamase-Inhibito-Resistant TEM Enzymes Which Differ by Naturally Occurring Variations and by Site-Directed Substitution at Asp276," Antimicrob. Agents Chemother. 42(6):1323-1328 (1998).
Carfi et al., "1.85 ANG. Resolution Structure of the Zinc II .beta.-Lactamase from Bacillus cereus," Acta Cryst. (1998) D54: 313-323.
Carfi et al., "X-ray Structure of the Zn11 .beta.-Lactamase from Bacteroides fragilis in an Orthorhombic Crystal Form," Acta. Cryst. (1998) D54: 47-57.
Carfi et al., "The 3-D structure of a zinc metallo-.beta.-lactamase from Bacillus cereus reveals a new type of protein fold," The EMBO Journal, 1995, vol. 14 No. 20: 4914-4921.
Chambliss, "The forgotten dosage form: enteric coated tablets," (1983) Pharm Technol 7, 124-140.
Chen et al.,".beta.-Lactamase Genes of the Penicillin-Susceptible Bacillus anthracis Sterne Strain," J. Bacteriol. 185(3):823-830 (2003).
Chica et al., "Semi-rational approaches to engineering enzyme activity: combining the benefits of directed evolution and rational design," Curr. Opin. Biotechnol., 2005, vol. 16: 378-384.
Cole, "Hydrolysis of Penicillins and Related Compounds by the Cell-Bound Penicillin Acylase of Escherichia coli," (1969) Biochem. J. 115, 733-739.
Colombo et al., "The ybxI Gene of Bacillus Subtilis 168 Encodes a Class D .beta-Lactamase of Low Activity," Antimicrobial Agents and Chemotherapy, Feb. 2004, vol. 48, No. 2, pp. 484-490.
Concha et al., "Crystal Structure of the IMP-1 Metallo .beta.-Lactamase from Pseudomonas aeruginosa and Its Complex with a Mercaptocarboxylate Inhibitor: Binding Determinants of a Potent, Broad-Spectrum Inhibitor," Biochemistry (2000) 39(15): 4288-4298.
Crawford, et al., "Over-expression, purification, and characterization of metallo-.beta.-lactarnase ImiS from Aeromonas veronii bv. sobria," Protein Expression and Purification 36 (2004) 272-279.
Davies and Abraham, "Separation, Purification and Properties of .beta.-Lactamase I and .beta.-Lactamase II from Bacillus cereus 569/H/9," (1974) Biochem. J. 143:115-127.
Delmas et al., "Structural Insights into Substrate Recognition and Product Expulsion in CTX-M Enzymes," J. Mol. Biol. 400:108-120 (2010).
Devos et al., "Practical limits of function prediction," Proteins: Structure, Function, and Genetics. 2000, vol. 41: 98-107.
Donskey, "Antibiotic Regimens and Intestinal Colonization with Antibiotic-Resistant Gram-Negative Bacilli," Clinical infectious Diseases, 2006, 43 Suppl 2, pp. S62-69.
Drawz et al, "The Role of a Second-Shell Residue in Modifying Substrate and Inhibitor Interactions in the SHV .beta.-Lactamase: A Study of Ambler Position Asn276," Biochem. 48(21):4557-4566 (2009).
Finnish Patent Search Report from Finnish Patent Office for FI 20065431, dated Oct. 24, 2007.
Galleni et al., "Standard Numbering Scheme for Class B .beta.-Lactamases," Antimicrobial Agents and Chemotherapy, Mar. 2001, vol. 45, No. 3, pp. 660-663.
Garau et al., "Update of the Standard Numbering Scheme for Class B .beta.-Lactamases," Guest Commentary, Antimicrobial Agents and Chemotherapy, Jul. 2004, pp. 2347-2349, vol. 48, No. 7.
Garau et al., "A Metallo-.beta.-lactamase Enzyme in Action: Crystal Structures of the Monozinc Carbapenemase CphA and its Complex with Biapenem," J. Mol. Biol. (2005) 345, 785-795.
Gazouli et al., "Effect of substitution of Asn for Arg-276 in the cefotaxime-hydrolyzing class A .beta.-lactamase CTX-M-4," FEMS Microbiol. Lett. 168:289-293 (1998).
Gebhard et al., "Mapping the Distribution of Conformational Information Throughout a Protein Sequence," J. Mol. Biol., 2006, 358, pp. 280-288.
Giakkoupi et al., "Aspartic acid for asparagine substitution at position 276 reduces susceptibility to mechanism-based inhibitors in SHV-1 and SHV-5 .beta.-lactamases," J. Antimicrobial. Chemother. 43:23-29 (1999).
Harmoinen et al., "Orally Administered Targeted Recombinant Beta-Lactamase Prevents Ampicillin-Induced Selective Pressure on the Gut Microbiota: A Novel Approach to Reducing Antimicrobial Resistance," Antimicrobial Agents and Chemotherapy, Jan. 2004, vol. 48, No. 1, pp. 75-79.
Harmoinen et al., "Enzymic Degradation of a .beta.-Lactam Antibiotic, Ampicillin, in the Gut; A Novel Treatment Modality," Journal

(56) References Cited

OTHER PUBLICATIONS of Antimicrobial Chemotherapy, 2003, 51, pp. 361-365. Hata et al., "Substrate Deacylation Mechanisms of Serine-.beta.-lactamases," Biol. Pharm. Bull. 29:2151-2159 (2006).
Herzberg, "Refined Crystal Structure of .beta.-Lactamase from *Staphylococcus aureus* PC1 at 2.0 .ANG. Resolution," J. Mol. Biol. 217:701-719 (1991).
Higgins et al., "In Vitro Activities of the .beta.-Lactamase Inhibitors Clavulanic Acid, Sulbactam, and Tazobactam Alone or in Combination with beta.-Lactams against Epidemiologically Characterized Multidrug-Resistant Acinetobacter baumannii Strains," Antimicrobial Agents and Chemotherapy, May 2004, vol. 48, No. 5, pp. 1586-1592.
Hirschl A et al. "Campylobacter pylori, Gastritis and Ulcus pepticum," Wien. Klin. Wsch. 14:493-497 (1987).
Horton et al., "Engineering hybrid genes without the use of restriction enzymes: gene splicing by overlap extension," 1989, Gene 77:61-68 (1989).
Huber et al. "Chapter 2. Preparative Methods for 7-Aminocephalosporanic Acid and 6-Aminopenicillanic Acid," (1972) In: Flynn E, ed. Cephalosporins and Penicillins. New York: Academic Press, 27-73.
Hyman, "Anaphylactic Shock After Therapy With Penicillinase," (1959) JAMA 169, 593-594. Illing et al., "Use of integrational plasmid excision to identify cellular localization of gene expression during sporulation in Bacillus subtilis," J. Bacteriol. 172(12):6937-6941 (1990).
International Search Report, PCT appl. No. PCT/FI93/00016 dated (May 7, 1993).
International Search Report, PCT appl. No. PCT/FI02/00861 dated (Feb. 11, 2003).
International Search Report, PCT appl. No. PCT/FI2007/050372 dated (Oct. 24, 2007).
International Search Report dated Mar. 3, 2008 for International Application No. PCT/FI2007/050627.
International Search Report, PCT appl. No. PCT/FI2011/050450 dated (Sep. 12, 2011).
Iserhard et al., "Epidemiology and Treatment of Gastric Campylobacter pylori Infection: more Questions than Answers," (1990) Hepato-Gastroenterol 37, 38-44.
Izui et al., "Large Exopenicillinase, Initial Extracellular Form Detected in Cultures of Bacillus licheniformis," Biochemistry, 1980, 19, pp. 1882-1886.
Kato et al., "Nucleotide Sequence of the .beta.-Lactamase Gene of *Alkalophilic Bacillus* sp. Strain 170," J. Gen. Microbiol. 131:3317-3324 (1985).
Katz, "Probiotics for the Prevention of Antibiotic-associated Diarrhea and Clostridium difficile Diarrhea," J. Clin. Gastroenterol., Mar. 2006, vol. 40, No. 3, pp. 249-255.
Kim and Buyn, "Purification and properties of ampicillin acylase from Pseudomonas melanogenum," (1990) Biochim Biophys Acta 1040, 12-18.
Kim et al., "Construction of spore mutants of Bacillus subtilis for the development as a host for foreign protein production," Biotechnology Letters 23:999-1004 (2001).
Kisselev L., "Polypeptide release factors in prokaryotes and eukaryotes: same function, different structure," Structure, 2002, vol. 10: 8-9.
Knox and Moews, ".beta.-Lactamase of Bacillus licheniformis 749/C: Refinement at 2 .ANG. Resolution and Analysis of Hydration," J. Mol. Bioi., 1991, 220, pp. 435-455.
Knox, "Extended-spectrum and inhibitor-resistant TEM-Type .beta.-lactamases: Mutations, Specificity, and Three-Dimensional Structure," Antimicrob. Agents Chemother., 1995, 39, 2593-2601.
Korhonen et al., "Milk Immunoglobulins and Complement Factors," British Journal of Nutrition, 2000, 84 Suppl 1, pp. S75-S80.
Kropp et al., "Metabolism of Thienamycin and Related Carbapenem Antibiotics by the Renal Dipeptidase, Dehydropeptidase-I," (1982) Antimicrob Agents Chemother 22, 62-70.

Kumakura et al., "Metabolic Fate of Clavulanic Acid and BRL 28500 in the Rat and Dog," Chemotherapy (Tokyo), 1986, 34 Suppl 4, pp. 187-201.
Lambert et al., "Susceptibility of Campylobacter pyloridis to 20 antimicrobial agents," (1986) Antimicrob Agents Chemother 30, (210): 510-511.
Ledent et al., "Unexpected Influence on a C-terminal-fused His-tag on Processing of an Enzyme and on the Kinetic and Folding Parameters", FEBS Lett, 1997, vol. 413, pp. 194-196.
Li et al., "Bottlenecks in the expression and secretion of heterologous proteins in Bacillus subtilis," Res. Microbiol. 155:605-610 (2004).
Lim et al., "Cloning, Nucleotide Sequence, and Expression of the Bacillus cereus 5/B/6 .beta.-Lactamase II Structural Gene," J. Bacteriol. 170:2873-2878 (1988).
Madan, "Methods of preparing microcapsules: interfacial polymerization," (1978) Pharm Technol 2, 68-75.
Madgwick and Waley, ".beta.-Lactamase I from Bacillus cereus," Biochem. J. 248(3):657-662 (1987).
Madonna et al., "Nucleotide sequence of the .beta.-lactamase I gene of Bacillus cereus strains 569/H and 5/B," Nucl. Acids Res. 15(4):1877 (1987).
Mandell and Sande, "Chapter 46. Antimicrobial Agents," (1990) In: Goodman and Gilman's, The Pharmacological Basis of Therapeutics, 8th Edition. New York: Pergamon Press, 1065-1097.
Marciano et al., "Analysis of the plasticity of location of the Arg244 positive charge within the active site of the TEM-1 .beta.-lactamase," Prot. Sci. 18:2080-2089 (2009).
Marmur, "A Procedure for the Isolation of Deoxylibonucleic Acid from Micro-organisms," J. Mol. Biol. (1961) 3:208-218.
Matagne et al., "Ragged N-termini and other Variants of Class A .beta.-Lactamases Analysed by Chromatofocusing," Biochem. J., 1991, 273, pp. 503-510.
Matagne et al., "Catalytic properties of class A .beta.-lactamases: efficiency and diversity," Biochem. J. 330:581-598 (1998).
Mentula et el., "Inhibition of ampicillin-induced emergence of resistance in intestinal coliforms by targeted recombinant .beta.-lactamase," International Journal of Antimicrobial Agents, (2004)24:555-561.
O'Callaghan et al., "Novel Method for Detevtion of .beta.-Lactamases by using a Chromogenic Cephalosporin Substrate, " Antimicrobial Agents and Chemotherapy, Apr. 1972, vol. 1, No. 4, pp. 283-288.
Perez-Llarena et al., "Structure-function studies of arginine at position 276 in CTX-M .beta.-lactamases," J. Antimicrob. Chemother. 61(4)792-797 (2008).
Pedraza-Reyes et al., "Temporal Regulation and Forespore-Specific Expression of the Spore Photoproduct Lyase Gene by Sigma-G RNA Polymerase during Bacillus subtilis Sporulation, " J. Bacteriol. 176(13): 3983-3991. 1994.
Pluckthun and Knowles, "The consequence of of stepwise deletions from the signal-processing site of .beta-lactamase," J. Biol.Chem., 1987, vol. 262 (9):3951-3957.
Rauws et al., "Campylobacter pyloridis-Associated Chronic Active Antral Gastritis," (1988) Gastroenterol 94, 33-40.
Rauws and Tytgat,"Cure of duodenal ulcer associated with eradicarion of Helicobacter pylon," (1990) Lancet 335, 1233-1235.
Rice et al., ".beta.-Lactam Antibiotics and Gastrointestinal Colonization with Vancomycin-Resistant Enterococci," J. Infect. Dis., 2004, 189, pp. 1113-1118.
Sambrook and Russell Molecular Cloning: A Laboratory Manual. "In vitro Amplification of DNA by the Polymerase Chain Reaction," vol. 2, Ch. 8, pp. 8.1-8.126. 2001.
Sande et al., "Chapter 44. Antimicrobial Agents," (1990) In: Goodman and Gilman's, The Pharmacological Basis of Therapeutics, 8th Edition. New York: Pergamon Press, 1018-1046.
Santillana et al., "Crystal structure of the carbapenemase OXA-24 reveals insights into the mechanism of carbapenem hydrolysis," Proc. Natl. Acad. Sci. USA, 104:5354-5359 (2007).
Santos et al., "Folding of an Abridged .beta.-Lactamase," Biochemistry, 2004, 43, pp. 1715-1723.

(56) References Cited

OTHER PUBLICATIONS

Saunders et al., "Use of Chromosomal Integration in the Establishment and Expression of blaZ, a *Staphylococcus aureus* .beta.-lactamase Gene, in Bacillus subtilis," J. Bacteriol. 157(3): 718-726. 1984.

Saves et al., "The Asparagine to Aspartic Acid Substitution at Position 276 of TEM-35 and TEM-36 is Involved in the .beta.-Lactamase Resistance to Clavulanic Acid," J. Biol. Chem. 270:18240-18245 (1995).

Sawa et al., "The Effect of Cefixime on Bacterial Flora in the Intestinal Tracts of Healthy Male Volunteers," (1985) Chemotherapy (Tokyo) 33, Suppl. 6, 169-180.

Search Report from National Board of Patents and Registration of Finland—Corresponding Finnish Application No. 20065757 dated (May 28, 2007).

Search Report from National Board of Patents and Registration of Finland—Corresponding Finnish Application No. 20105572 dated (2010).

Sen et al., "Developments in directed evolution for improving enzyme functions," Appl. Biochem Biotechnol., Aug. 18, 2007, vol. 143: 212-223.

Shimooka et al, "Absorption, Distribution, and Excretion of Sulbactam and Ampilcilin after Intravenous Administration in Rats and Dogs," Chemotherapy (Tokyo), 1988, 36 Suppl 8, pp. 66-80.

Simm et al., "Characterization of Monomeric L1 Metallo-.beta.-lactamase and the Role of the N-terminal Extension in Negative Cooperativity and Antibiotic Hydrolysis," The Journal of Biological Chemistry (Jul. 2002) vol. 277 No. 27:4744-24752.

Sjolund et al., "Long-Term Persistence of Resistant *Enterococcus* Species after Antibiotics to Eradicate Helicobacter pylori," Ann. Intern. Med. 139:483-487 (2003).

Stiefel et al., "Oral Administration of .beta.-Lactamase Preserves Colonization Resistance of Piperacillin-Treated Mice," J. Infect. Dis., 2003, 188, pp. 1605-1609.

Stiefel et al., "Orally Administered Recombinant Metallo-.beta.-Lactamase Preserves Colonization Resistance of Piperacillin-Tazobactam-Treated Mice," Antimicrobial Agents and Chemotherapy, Dec. 2005, vol. 49, No. 12, pp. 5190-5191.

Stiefel et al., "Orally administered beta-lactamase enzymes represent a novel strategy to prevent colonization by Clostridium difficile" Journal of Antimicrobial Chemotherapy, 2008, 62, 1105-1108.

Sullivan et al., "Effect of Antimicrobial Agents on the Ecological Balance of Human Microllora," Lancet Infect. Dis., 2001, vol. 1, pp. 101-114.

Supplementary EP Search Report relating to Corresponding EP 07765926.6, dated Mar. 4, 2010.

Tarkkanen et al., "P1A Recombinant .beta.-Lactamase Prevents Emergence of Antimicrobial Resistance in Gut Microflora of Healthy Subjects during Intravenous Administration of Ampicillin," Antimicrob. Agents Chemother. 53:2455-2462 (2009).

Therapeutic Drugs (1991), Dollery C, ed. Edinburgh: Churchill Livingstone, "Ceftriaxone (sodium)," c 127-c133.

Tranier et al., "The High Resolution Crystal Structure for Class A .beta.-Lactamase PER-1 Reveals the Bases for Its increase in Breadth of Activity," J. Biol. Chem. 275:28075-28082 (2000).

Walsh et al., "Metallo-.beta.-Lactamases: the Quiet before the Storm?" Clinical Microbiology Reviews (Apr. 2005) vol. 18 No. 2: 306-325.

Walther-Rasmussen et al., "Terminal truncations in Amp C .beta.-lactamase from a clinical isolate of Pseudomonas aeruginosa," Eur. J. Biochem.(1999) 263: 478-485.

\* cited by examiner

SEQUENCE LISTING

<160> NUMBER OF SEQ ID NOS: 7

<210> SEQ ID NO 1
<211> LENGTH: 263
<212> TYPE: PRT
<213> ORGANISM: Bacillus licheniformis

<400> SEQUENCE: 1

```
Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Tyr Thr Arg Asp Asp Leu Val Asn Tyr Asn Pro Ile Thr Glu
65                  70                  75                  80

Lys His Val Asp Thr Gly Met Thr Leu Lys Glu Leu Ala Asp Ala Ser
                85                  90                  95

Leu Arg Tyr Ser Asp Asn Ala Ala Gln Asn Leu Ile Leu Lys Gln Ile
            100                 105                 110

Gly Gly Pro Glu Ser Leu Lys Lys Glu Leu Arg Lys Ile Gly Asp Glu
        115                 120                 125

Val Thr Asn Pro Glu Arg Phe Glu Pro Glu Leu Asn Glu Val Asn Pro
    130                 135                 140

Gly Glu Thr Gln Asp Thr Ser Thr Ala Arg Ala Leu Val Thr Ser Leu
145                 150                 155                 160

Arg Ala Phe Ala Leu Glu Asp Lys Leu Pro Ser Glu Lys Arg Glu Leu
                165                 170                 175

Leu Ile Asp Trp Met Lys Arg Asn Thr Thr Gly Asp Ala Leu Ile Arg
            180                 185                 190

Ala Gly Val Pro Asp Gly Trp Glu Val Ala Asp Lys Thr Gly Ala Ala
        195                 200                 205

Ser Tyr Gly Thr Arg Asn Asp Ile Ala Ile Ile Trp Pro Pro Lys Gly
    210                 215                 220

Asp Pro Val Val Leu Ala Val Leu Ser Ser Arg Asp Lys Lys Asp Ala
225                 230                 235                 240

Lys Tyr Asp Asp Lys Leu Ile Ala Glu Ala Thr Lys Val Val Met Lys
                245                 250                 255

Ala Leu Asn Met Asn Gly Lys
            260
```

<210> SEQ ID NO 2
<211> LENGTH: 792
<212> TYPE: DNA
<213> ORGANISM: Bacillus licheniformis

<400> SEQUENCE: 2

```
gagatgaaag atgattttgc aaaacttgag gaacaatttg atgcaaaact cgggatcttt      60
gcattggata caggtacaaa ccggacggta gcgtatcggc cggatgagcg ttttgctttt     120
```

```
gcttcgacga ttaaggcttt aactgtaggc gtgcttttgc aacagaaatc aatagaagat    180
ctgaaccaga gaataacata tacacgtgat gatcttgtaa actacaaccc gattacggaa    240
aagcacgttg atacgggaat gacgctcaaa gagcttgcgg atgcttcgct tcgatatagt    300
gacaatgcgg cacagaatct cattcttaaa caaattggcg gacctgaaag tttgaaaaag    360
gaactgagga agattggtga tgaggttaca aatcccgaac gattcgaacc agagttaaat    420
gaagtgaatc cgggtgaaac tcaggatacc agtacagcaa gagcacttgt cacaagcctt    480
cgagcctttg ctcttgaaga taaacttcca agtgaaaaac gcgagctttt aatcgattgg    540
atgaaacgaa ataccactgg agacgcctta atccgtgccg gtgtgccgga cggttgggaa    600
gtggctgata aactggagc ggcatcatat ggaacccgga atgacattgc catcatttgg    660
ccgccaaaag gagatcctgt cgttcttgca gtattatcca gcagggataa aaaggacgcc    720
aagtatgatg ataaacttat tgcagaggca acaaaggtgg taatgaaagc cttaaacatg    780
aacggcaaat aa                                                        792
```

<210> SEQ ID NO 3
<211> LENGTH: 299
<212> TYPE: PRT
<213> ORGANISM: Bacillus licheniformis

<400> SEQUENCE: 3

```
Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
65                  70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
        195                 200                 205

Lys Arg Glu Leu Leu Ile Asp Trp Met Lys Arg Asn Thr Thr Gly Asp
    210                 215                 220

Ala Leu Ile Arg Ala Gly Val Pro Asp Gly Trp Glu Val Ala Asp Lys
225                 230                 235                 240

Thr Gly Ala Ala Ser Tyr Gly Thr Arg Asn Asp Ile Ala Ile Ile Trp
```

```
                    245                 250                 255
Pro Pro Lys Gly Asp Pro Val Val Leu Ala Val Leu Ser Ser Arg Asp
        260                 265                 270

Lys Lys Asp Ala Lys Tyr Asp Asp Lys Leu Ile Ala Glu Ala Thr Lys
        275                 280                 285

Val Val Met Lys Ala Leu Asn Met Asn Gly Lys
        290                 295
```

<210> SEQ ID NO 4
<211> LENGTH: 900
<212> TYPE: DNA
<213> ORGANISM: Bacillus licheniformis

<400> SEQUENCE: 4

```
atgattcaaa aacgaaagcg gacagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg gatgagcgtt ttgcttttgc ttcgacgatt     240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca aagccttcg agcctttgct      600
cttgaagata aacttccaag tgaaaaacgc gagcttttaa tcgattggat gaaacgaaat     660
accactggag acgccttaat ccgtgccggt gtgccggacg gttgggaagt ggctgataaa     720
actggagcgg catcatatgg aaccccggaat gacattgcca tcatttggcc gccaaaagga     780
gatcctgtcg ttcttgcagt attatccagc agggataaaa aggacgccaa gtatgatgat     840
aaacttattg cagaggcaac aaaggtggta atgaaagcct aaacatgaa cggcaaataa      900
```

<210> SEQ ID NO 5
<211> LENGTH: 262
<212> TYPE: PRT
<213> ORGANISM: Artificial Sequence
<220> FEATURE:
<223> OTHER INFORMATION: Synthetic

<400> SEQUENCE: 5

```
Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Thr Arg Asp Asp Leu Val Asn Tyr Asn Pro Ile Thr Glu Lys
65                  70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110
```

-continued

```
Gly Pro Glu Ser Leu Lys Lys Glu Leu Arg Lys Ile Gly Asp Glu Val
            115                 120                 125

Thr Asn Pro Glu Arg Phe Glu Pro Glu Leu Asn Glu Val Asn Pro Gly
130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Val Pro Asp Gly Trp Glu Val Gly Asp Lys Thr Gly Ser Gly Asp
        195                 200                 205

Tyr Gly Thr Arg Asn Asp Ile Ala Ile Ile Trp Pro Pro Lys Gly Asp
    210                 215                 220

Pro Val Leu Ala Val Leu Ser Ser Arg Asp Lys Lys Asp Ala Lys
225                 230                 235                 240

Tyr Asp Asn Lys Leu Ile Ala Glu Ala Thr Lys Val Val Met Lys Ala
                245                 250                 255

Leu Asn Met Asn Gly Lys
            260
```

<210> SEQ ID NO 6
<211> LENGTH: 299
<212> TYPE: PRT
<213> ORGANISM: Artificial Sequence
<220> FEATURE:
<223> OTHER INFORMATION: Synthetic

<400> SEQUENCE: 6

```
Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
65                  70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
        195                 200                 205
```

```
Lys Arg Glu Leu Leu Ile Asp Trp Met Lys Arg Asn Thr Thr Gly Asp
    210                 215                 220

Ala Leu Ile Arg Ala Gly Val Pro Asp Gly Trp Glu Val Gly Asp Lys
225                 230                 235                 240

Thr Gly Ser Gly Asp Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
                260                 265                 270

Lys Lys Asp Ala Lys Tyr Asp Asn Lys Leu Ile Ala Glu Ala Thr Lys
                275                 280                 285

Val Val Met Lys Ala Leu Asn Met Asn Gly Lys
    290                 295

<210> SEQ ID NO 7
<211> LENGTH: 900
<212> TYPE: DNA
<213> ORGANISM: Artificial Sequence
<220> FEATURE:
<223> OTHER INFORMATION: Synthetic

<400> SEQUENCE: 7
atgattcaaa aacgaaagcg gacagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg gatgagcgtt ttgcttttgc ttcgacgatt     240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca caagccttcg agcctttgct     600
cttgaagata aacttccaag tgaaaaacgc gagcttttaa tcgattggat gaaacgaaat     660
accactggag acgccttaat ccgtgccggt gtgccggacg gttgggaagt gggtgataaa     720
actggaagcg gagattatgg aacccggaat gacattgcca tcatttggcc gccaaaagga     780
gatcctgtcg ttcttgcagt attatccagc agggataaaa aggacgccaa gtatgataat     840
aaacttattg cagaggcaac aaaggtggta atgaaagcct taaacatgaa cggcaaataa     900
```

BETA-LACTAMASES WITH IMPROVED PROPERTIES FOR THERAPY

RELATED APPLICATIONS

This application is a continuation of U.S. patent application Ser. No. 16/112,283 (now U.S. Pat. No. 10,336,995), which is a continuation of U.S. patent application Ser. No. 15/993,159 (now U.S. Pat. No. 10,087,433), which is a continuation of U.S. patent application Ser. No. 15/674,177, filed on Aug. 10, 2017 (now U.S. Pat. No. 10,011,824), which is a continuation of U.S. patent application Ser. No. 15/611,881, filed Jun. 2, 2017 (now U.S. Pat. No. 9,783,797), which is a continuation of U.S. patent application Ser. No. 15/245,517, filed Aug. 24, 2016 (now U.S. Pat. No. 9,695,409), which is a continuation of U.S. patent application Ser. No. 15/200,508, filed Jul. 1, 2016 (now U.S. Pat. No. 9,464,280), which is a continuation of U.S. patent application Ser. No. 15/160,669 (now U.S. Pat. No. 9,404,103), filed May 20, 2016, which is a continuation of U.S. patent application Ser. No. 15/019,474, filed Feb. 9, 2016 (now U.S. Pat. No. 9,376,673), which is a continuation of U.S. patent application Ser. No. 14/689,877, filed Apr. 17, 2015 (now U.S. Pat. No. 9,290,754), which claims the benefit of U.S. Provisional Patent Application No. 61/980,844, filed Apr. 17, 2014, and U.S. Provisional Patent Application No. 62/046,627, filed Sep. 5, 2014, all of which are hereby incorporated by reference in their entirety.

FIELD OF THE INVENTION

This invention relates to, in part, compositions of beta-lactamases and methods for using these enzymes in, for example, gastrointestinal tract (GI tract) disorders such as *C. difficile* infection (CDI).

BACKGROUND

Humans may be considered to be a "superorganism" which is a conglomerate of mammalian and microbial cells, with the latter estimated to outnumber the former by ten to one. This microbial component, and its microbial genetic repertoire, the microbiome, is roughly 100-times greater than that of the human host. Strikingly, despite this enormous diversity of foreign organisms, the human immune system generally maintains a state of synergy. This is particularly true of the distal GI tract, which houses up to 1000 distinct bacterial species and an estimated excess of $1 \times 10^{14}$ microorganisms, and appears to be central in defining human host health status. Loss of the careful balance in the microbiome, especially in the GI tract, can lead to various diseases.

However, antibiotic medical treatments, which are needed to treat certain aspects of disease, can induce disruption in the microbiome, including in the GI tract, and lead to further disease. For instance, certain parentally administered beta-lactams like ampicillin, ceftriaxone, cefoperazone, and piperacillin are, in part, eliminated via biliary excretion into the proximal part of the small intestine (duodenum). Residual unabsorbed beta-lactams in the intestinal tract may cause an undesirable effect on the ecological balance of normal intestinal microbiota resulting in, for example, CDI, antibiotic-associated diarrhea, overgrowth of pathogenic bacteria such as vancomycin resistant enterococci (VRE), extended-spectrum beta-lactamase producing Gram-negative bacilli (ESBL), and fungi, and selection of antibiotic-resistance strains among both normal intestinal microbiota and potential pathogen bacteria.

One approach for avoiding or rebalancing the ecological balance of normal intestinal microbiota is the therapeutic use of beta-lactamases, for example, by inactivating excreted or unabsorbed antibiotics in the GI tract, thereby maintaining a normal intestinal microbiota and preventing its overgrowth with potentially pathogenic micro-organisms.

There remains a need for agents and medicaments for the treatment of gastrointestinal tract (GI tract) disorders such as *C. difficile* infection (CDI) which have enzymatic properties that are best suited for these uses.

SUMMARY OF THE INVENTION

Accordingly, the present invention provides for beta-lactamases comprising an amino acid sequence that is based on the P1A beta-lactamase but containing advantageous mutations that, for example, change substrate specificity and/or activity and provide for therapeutic advantages. For example, such mutants can have at least 70% sequence identity with SEQ ID NO: 1 and have one or more mutations at the following Ambler classification positions F33, Q135, G156, A232, A237, A238, S240, T243, R244, S266, and D276. Such beta-lactamases have the ability to hydrolyze both penicillins and cephalosporins and do so with enzymatically desirable characteristics, such as low $K_M$s and/or high $V_{max}$s for select antibiotic substrates.

These improved beta-lactamases find uses in a number of therapies, including the prevention or treatment of CDI and/or a *C. difficile*-associated disease or other antibiotic-induced adverse effects in the GI tract. For example, the beta-lactamases find use in allowing a patient to undergo antibiotic therapy while being protected against disease that could result from excess antibiotics negatively affecting the microbiome. Such use does not interfere with the systemic utility of the antibiotic. Rather, the beta-lactamases clear out excess antibiotic that may populate parts of the GI tract and, in doing so, prevent the disruption of the microbiota that is linked to the various disease states described herein.

SEQ ID NO: 1

Figure 1:
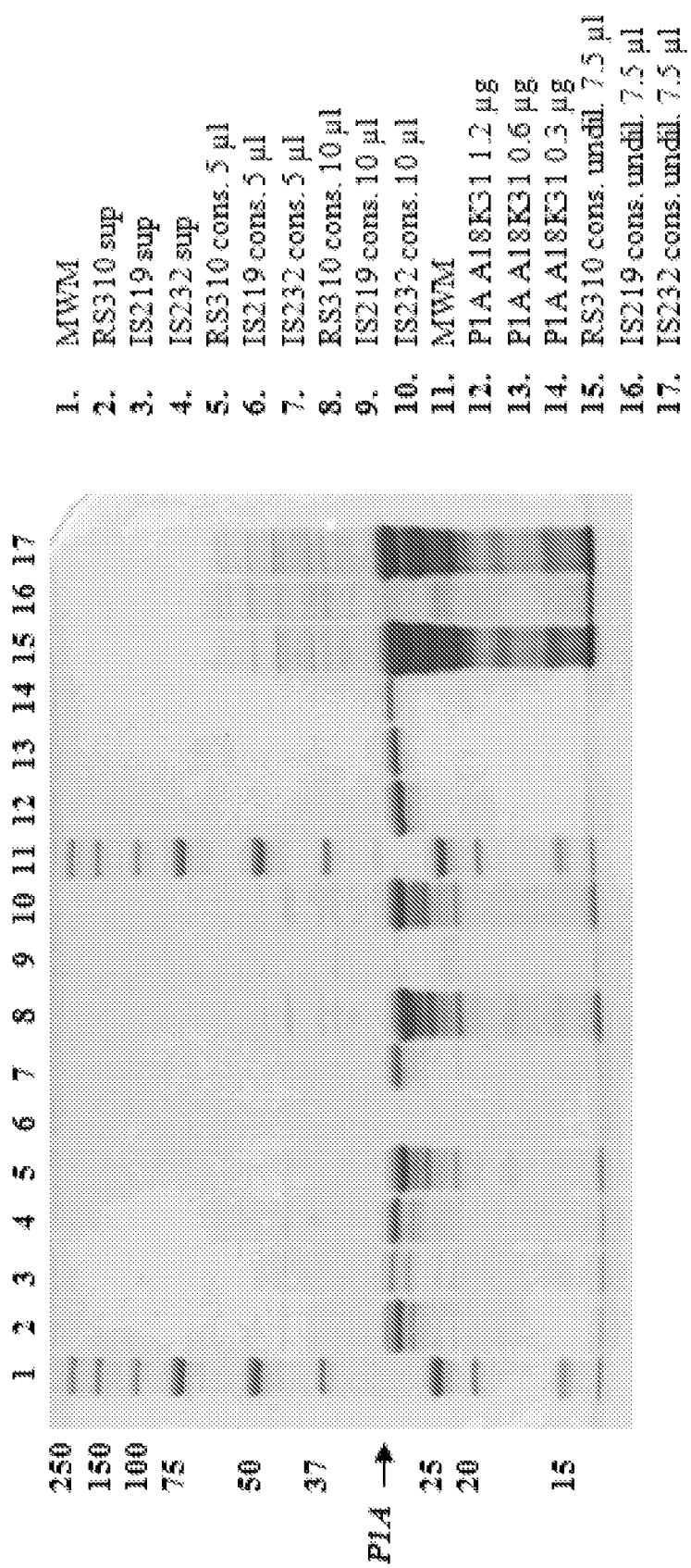
FIG. 1 shows a 12% Bis-Tris Criterion XT SDS-PAGE (BioRad) gel with concentrated samples (see labels of the samples to the right of the gel) from a 10 g/l glucose *B. subtilis* growth. MWM=molecular weight marker Precision Plus (BioRad), RS310=P1A *B. subtilis* strain and P1A A18K31=P1A reference material. "P1A→" denotes the right size of P1A and the mutant proteins.

Glu Met Lys Asp Asp Phe Ala Lys Leu Glu Glu Gln Phe
Asp Ala Lys Leu Gly Ile Phe Ala Leu Asp Thr Gly Thr
Asn Arg Thr Val Ala Tyr Arg Pro Asp Glu Arg Phe Ala
Phe Ala Ser Thr Ile Lys Ala Leu Thr Val Gly Val Leu
Leu Gln Gln Lys Ser Ile Glu Asp Leu Asn Gln Arg Ile
Thr Tyr Thr Arg Asp Asp Leu Val Asn Tyr Asn Pro Ile
Thr Glu Lys His Val Asp Thr Gly Met Thr Leu Lys Glu
Leu Ala Asp Ala Ser Leu Arg Tyr Ser Asp Asn Ala Ala
Gln Asn Leu Ile Leu Lys Gln Ile Gly Gly Pro Glu Ser
Leu Lys Lys Glu Leu Arg Lys Ile Gly Asp Glu Val Thr
Asn Pro Glu Arg Phe Glu Pro Glu Leu Asn Glu Val Asn
Pro Gly Glu Thr Gln Asp Thr Ser Thr Ala Arg Ala Leu
Val Thr Ser Leu Arg Ala Phe Ala Leu Glu Asp Lys Leu
Pro Ser Glu Lys Arg Glu Leu Leu Ile Asp Trp Met Lys
Arg Asn Thr Thr Gly Asp Ala Leu Ile Arg Ala Gly Val
Pro Asp Gly Trp Glu Val Ala Asp Lys Thr Gly Ala Ala
Ser Tyr Gly Thr Arg Asn Asp Ile Ala Ile Ile Trp Pro
Pro Lys Gly Asp Pro Val Val Leu Ala Val Leu Ser Ser
Arg Asp Lys Lys Asp Ala Lys Tyr Asp Asp Lys Leu Ile
Ala Glu Ala Thr Lys Val Val Met Lys Ala Leu Asn Met
Asn Gly Lys.

In some embodiments, SEQ ID NO: 1 may have a Met and/or Thr preceeding the first residue of the sequence. In various embodiments, the Met may be cleaved. As described herein, mutations may be made to the sequence comprising the Met and/or Thr preceeding the first residue to generate the inventive beta-lactamases.

Also provided herein is the 299 amino acid sequence of the P1A enzyme before removal of a 31 amino acid signal sequence and the QASKT (Gln-Ala-Ser-Lys-Thr) pentapeptide at the N terminus as SEQ ID NO: 3:

SEQ ID NO: 3

Met Ile Gln Lys Arg Lys Arg Thr Val Ser Phe Arg Leu
Val Leu Met Cys Thr Leu Leu Phe Val Ser Leu Pro Ile
Thr Lys Thr Ser Ala Gln Ala Ser Lys Thr Glu Met Lys
Asp Asp Phe Ala Lys Leu Glu Glu Gln Phe Asp Ala Lys
Leu Gly Ile Phe Ala Leu Asp Thr Gly Thr Asn Arg Thr
Val Ala Tyr Arg Pro Asp Glu Arg Phe Ala Phe Ala Ser
Thr Ile Lys Ala Leu Thr Val Gly Val Leu Leu Gln Gln
Lys Ser Ile Glu Asp Leu Asn Gln Arg Ile Thr Tyr Thr
Arg Asp Asp Leu Val Asn Tyr Asn Pro Ile Thr Glu Lys
His Val Asp Thr Gly Met Thr Leu Lys Glu Leu Ala Asp
Ala Ser Leu Arg Tyr Ser Asp Asn Ala Ala Gln Asn Leu
Ile Leu Lys Gln Ile Gly Gly Pro Glu Ser Leu Lys Lys
Glu Leu Arg Lys Ile Gly Asp Glu Val Thr Asn Pro Glu
Arg Phe Glu Pro Glu Leu Asn Glu Val Asn Pro Gly Glu
Thr Gln Asp Thr Ser Thr Ala Arg Ala Leu Val Thr Ser
Leu Arg Ala Phe Ala Leu Glu Asp Lys Leu Pro Ser Glu
Lys Arg Glu Leu Leu Ile Asp Trp Met Lys Arg Asn Thr
Thr Gly Asp Ala Leu Ile Arg Ala Gly Val Pro Asp Gly
Trp Glu Val Ala Asp Lys Thr Gly Ala Ala Ser Tyr Gly
Thr Arg Asn Asp Ile Ala Ile Ile Trp Pro Pro Lys Gly
Asp Pro Val Val Leu Ala Val Leu Ser Ser Arg Asp Lys
Lys Asp Ala Lys Tyr Asp Asp Lys Leu Ile Ala Glu Ala
Thr Lys Val Val Met Lys Ala Leu Asn Met Asn Gly Lys

Further, the present invention also provides for additional upstream residues from the first residue of SEQ ID NO: 1 (see, e.g., *JBC* 258 (18): 11211, 1983, the contents of which are hereby incorporated by reference-including the exo-large and exo-small versions of penP and penP1). Further, the present invention also provides for additional downstream residues from the last residue of SEQ ID NO: 1.

The polynucleotide sequence of P1A (after removal of a 31 amino acid signal sequence and the QAKST pentapeptide at the N terminus) is also provided as SEQ ID NO: 2. As described herein, mutations may be made to this sequence to generate the inventive beta-lactamases (including, taking into account degeneracy of the genetic code).

SEQ ID NO: 2

```
gagatgaaagatgattttgcaaaacttgaggaacaatttgatgcaaaactc
gggatctttgcattggatacaggtacaaaccggacggtagcgtatcggccg
gatgagcgttttgcttttgcttcgacgattaaggctttaactgtaggcgtg
cttttgcaacagaaatcaatagaagatctgaaccagagaataacatataca
cgtgatgatcttgtaaactacaacccgattacggaaaagcacgttgatacg
ggaatgacgctcaaagagcttgcggatgcttcgcttcgatatagtgacaat
gcggcacagaatctcattcttaaacaaattggcggacctgaaagtttgaaa
aaggaactgaggaagattggtgatgaggttacaaatcccgaacgattcgaa
ccagagttaaatgaagtgaatccgggtgaaactcaggataccagtacagca
agagcacttgtcacaagccttcgagcctttgctcttgaagataaacttcca
agtgaaaaacgcgagcttttaatcgattggatgaaacgaaataccactgga
gacgccttaatccgtgccggtgtgccggacggttgggaagtggctgataaa
actggagcggcatcatatggaacccggaatgacattgccatcatttggccg
ccaaaaggagatcctgtcgttcttgcagtattatccagcagggataaaaag
gacgccaagtatgatgataaacttattgcagaggcaacaaaggtggtaatg
aaagcctttaaacatgaacggcaaataa
```

Also provided is the polynucleotide sequence of P1A before the removal of a 31 amino acid signal sequence and the QASKT pentapeptide at the N terminus as SEQ ID NO:

4. As described herein, mutations may be made to this sequence to generate the inventive beta-lactamases (including, taking into account degeneracy of the genetic code).

SEQ ID NO: 4
atgattcaaaaacgaaagcggacagtttcgttcagacttgtgcttatgtgc acgctgttatttgtcagtttgccgattacaaaaacatcagcgcaagcttcc aagacggagatgaaagatgattttgcaaaacttgaggaacaatttgatgca aaactcgggatctttgcattggatacaggtacaaaccggacggtagcgtat cggccggatgagcgttttgcttttgcttcgacgattaaggctttaactgta ggcgtgcttttgcaacagaaatcaatagaagatctgaaccagagaataaca tatacacgtgatgatcttgtaaactacaacccgttacggaaaagcacgttg atacgggaatgacgctcaaagagcttgcggatgcttcgcttcgatatagtg acaatgcggcacagaatctcattcttaaacaaattggcggacctgaaagtt tgaaaaaggaactgaggaagattggtgatgaggttacaaatcccgaacgat tcgaaccagagttaaatgaagtgaatccgggtgaaactcaggataccagta cagcaagagcacttgtcacaagccttcgagcctttgctcttgaagataaac ttccaagtgaaaaacgcgagcttttaatcgattggatgaaacgaaatacca ctggagacgccttaatccgtgccggtgtgccggacggttgggaagtggctg ataaaactggagcggcatcatatggaacccggaatgacattgccatcattt ggccgccaaaaggagatcctgtcgttcttgcagtattatccagcagggata aaaaggacgccaagtatgatgataaacttattgcagaggcaacaaaggtgg taatgaaagccttaaacatgaacggcaaataa In some embodiments, the invention pertains to mutagenesis of a beta-lactamase (e.g. a class A beta-lactamase) to derive advantageous enzymes (e.g. those that can target a broad spectra of antibiotics). In some embodiments, the invention includes site-directed mutagenesis, random mutagenesis, and/or directed evolution approaches. In some embodiments, mutation design is based on, inter alia, structural data (e.g. crystal structure data, homolog models, etc.) of the following: P1A crystal structure (Knox and Moews, J. Mol Biol., 220, 435-455 (1991)), CTX-M-44 (1BZA (Ibuka et al. *Journal of Molecular Biology Volume* 285, Issue 5 2079-2087 (1999), 1 IYS (Ibuka et al. *Biochemistry,* 2003, 42 (36): 10634-43), 1IYO, 1IYP and 1IYQ (Shimamura et al. 2002 *J. Biol. Chem.* 277:46601-08), *Proteus vulgaris* K1 (1HZO, Nugaka et al. *J Mol Biol.* 2002 Mar. 15; 317(1): 109-17) and *Proteus penneri* HugA (Liassine et al. *Antimicrob Agents Chemother.* 2002 January; 46(1):216-9. 2002), and reviewed in Bonnet, *Antimicrob. Agents Chemother* 48(1): 1-14 (2004) (for CTM-X), the contents of all of these documents are hereby incorporated by reference in their entirety). In some embodiments, the present mutations are informed by analysis of structural data (e.g. crystal structure data, homolog models, etc.) of any one of the following beta-lactamases: P1A (see, e.g. U.S. Pat. No. 5,607,671, the contents of which are hereby incorporated by reference), P2A (see, e.g., WO 2007/147945, the contents of which are hereby incorporated by reference), P3A (see, e.g., WO 2011/148041, the contents of which are hereby incorporated by reference), CTX-M-3, CTX-M-4, CTX-M-5, CTX-M-9, CTX-M-10, CTX-M-14, CTX-M-15, CTX-M-16, CTX-M-18, CTX-M-19, CTX-M-25, CTX-M-26, CTX-M-27, CTX-M-32, CTX-M-44, CTX-M-45, and CTX-M-54. Such information is available to one skilled in the art at known databases, for example, Swiss-Prot Protein Sequence Data Bank, NCBI, and PDB.

In some embodiments, the invention pertains to one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations to SEQ ID NO: 1 or SEQ ID NO: 3 or a sequence with at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 1 or SEQ ID NO: 3 (or about 70%, or about 75%, or about 80%, or about 85%, or about 90%, or about 95%, or about 96%, or about 97%, or about 98%, or about 99% identity to SEQ ID NO: 1 or SEQ ID NO: 3). In various embodiments, one or more amino acid of SEQ ID NO: 1 or SEQ ID NO: 3 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and δ-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as P methyl amino acids, Cα-methyl amino acids, Nα-methyl amino acids, and amino acid analogs in general).

In illustrative embodiments, inventive mutations include, but are not limited to one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) of the following mutations to SEQ ID NO: 1 or SEQ ID NO: 3 or a sequence with at least 30, 35, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.8, 99.9% identity to SEQ ID NO: 1 or SEQ ID NO: 3 (or about 70%, or about 75%, or about 80%, or about 85%, or about 90%, or about 95%, or about 96%, or about 97%, or about 98%, or about 99% identity to SEQ ID NO: 1 or SEQ ID NO: 3): Glu1Ala; Glu1Cys; Glu1Asp; Glu1Phe; Glu1Gly; Glu1His; Glu1Ile; Met1Lys; Glu1Leu; Glu1Met; Glu1Asn; Glu1Pro; Glu1Gln; Glu1Arg; Glu1Ser; Glu1Thr; Glu1Val; Glu1Trp; Glu1Tyr; Met2Ala; Met2Cys; Met2Asp; Met2Glu; Met2Phe; Met2Gly; Met2His; Met2Ile; Met1Lys; Met2Leu;

Met2Asn; Met2Pro; Met2Gln; Met2Arg; Met2Ser; Met2Thr; Met2Val; Met2Trp; Met2Tyr; Lys3Ala; Lys3Cys; Lys3Asp; Lys3Glu; Lys3Phe; Lys3Gly; Lys3His; Lys3Ile; Lys3Leu; Lys3Met; Lys3Asn; Lys3Pro; Lys3Gln; Lys3Arg; Lys3Ser; Lys3Thr; Lys3Val; Lys3Trp; Lys3Tyr; Asp4Ala; Asp4Cys; Asp4Glu; Asp4Phe; Asp4Gly; Asp4His; Asp4Ile; Asp4Lys; Asp4Leu; Asp4Met; Asp4Asn; Asp4Pro; Asp4Gln; Asp4Arg; Asp4Ser; Asp4Thr; Asp4Val; Asp4Trp; Asp4Tyr; Asp5Ala; Asp5Cys; Asp5Glu; Asp5Phe; Asp5Gly; Asp5His; Asp5Ile; Asp5Lys; Asp5Leu; Asp5Met; Asp5Asn; Asp5Pro; Asp5Gln; Asp5Arg; Asp5Ser; Asp5Thr; Asp5Val; Asp5Trp; Asp5Tyr; Phe6Ala; Phe6Cys; Phe6Asp; Phe6Glu; Phe6Gly; Phe6His; Phe6Ile; Phe6Lys; Phe6Leu; Phe6Met; Phe6Asn; Phe6Pro; Phe6Gln; Phe6Arg; Phe6Ser; Phe6Thr; Phe6Val; Phe6Trp; Phe6Tyr; Ala7Cys; Ala7Asp; Ala7Glu; Ala7Phe; Ala7Gly; Ala7His; Ala7Ile; Ala7Lys; Ala7Leu; Ala7Met; Ala7Asn; Ala7Pro; Ala7Gln; Ala7Arg; Ala7Ser; Ala7Thr; Ala7Val; Ala7Trp; Ala7Tyr; Lys8Ala; Lys8Cys; Lys8Asp; Lys8Glu; Lys8Phe; Lys8Gly; Lys8His; Lys8Ile; Lys8Leu; Lys8Met; Lys8Asn; Lys8Pro; Lys8Gln; Lys8Arg; Lys8Ser; Lys8Thr; Lys8Val; Lys8Trp; Lys8Tyr; Leu9Ala; Leu9Cys; Leu9Asp; Leu9Glu; Leu9Phe; Leu9Gly; Leu9His; Leu9Ile; Leu9Lys; Leu9Met; Leu9Asn; Leu9Pro; Leu9Gln; Leu9Arg; Leu9Ser; Leu9Thr; Leu9Val; Leu9Trp; Leu9Tyr; Glu10Ala; Glu10Cys; Glu10Asp; Glu10Phe; Glu10Gly; Glu10His; Glu10Ile; Glu10Lys; Glu10Leu; Glu10Met; Glu10Asn; Glu10Pro; Glu10Gln; Glu10Arg; Glu10Ser; Glu10Thr; Glu10Val; Glu10Trp; Glu10Tyr; Glu11Ala; Glu11Cys; Glu11Asp; Glu11Phe; Glu11Gly; Glu11His; Glu11Ile; Glu11Lys; Glu11Leu; Glu11Met; Glu11Asn; Glu11Pro; Glu1111Gln; Glu11Arg; Glu1111Ser; Glu11Thr; Glu11Val; Glu1111Trp; Glu11Tyr; Gln12Ala; Gln12Cys; Gln12Asp; Gln12Glu; Gln12Phe; Gln12Gly; Gln12His; Gln12Ile; Gln12Lys; Gln12Leu; Gln12Met; Gln12Asn; Gln12Pro; Gln12Arg; Gln12Ser; Gln12Thr; Gln12Val; Gln12Trp; Gln12Tyr; Phe13Ala; Phe13Cys; Phe13Asp; Phe13Glu; Phe13Gly; Phe13His; Phe13Ile; Phe13Lys; Phe13Leu; Phe13Met; Phe13Asn; Phe13Pro; Phe13Gln; Phe13Arg; Phe13Ser; Phe13Thr; Phe13Val; Phe13Trp; Phe13Tyr; Asp14Ala; Asp14Cys; Asp14Glu; Asp14Phe; Asp14Gly; Asp14His; Asp41Ile; Asp14Lys; Asp14Leu; Asp14Met; Asp14Asn; Asp14Pro; Asp14Gln; Asp14Arg; Asp14Ser; Asp14Thr; Asp14Val; Asp14Trp; Asp14Tyr; Ala15Cys; Ala15Asp; Ala15Glu; Ala15Phe; Ala15Gly; Ala15His; Ala15Ile; Ala15Lys; Ala15Leu; Ala15Met; Ala15Asn; Ala15Pro; Ala15Gln; Ala15Arg; Ala15Ser; Ala15Thr; Ala15Val; Ala15Trp; Ala15Tyr; Lys16Ala; Lys16Cys; Lys16Asp; Lys16Glu; Lys16Phe; Lys16Gly; Lys16His; Lys61Ile; Lys16Leu; Lys16Met; Lys16Asn; Lys16Pro; Lys16Gln; Lys16Arg; Lys16Ser; Lys16Thr; Lys16Val; Lys16Trp; Lys16Tyr; Leu17Ala; Leu17Cys; Leu17Asp; Leu17Glu; Leu17Phe; Leu17Gly; Leu17His; Leu17Ile; Leu17Lys; Leu17Met; Leu17Asn; Leu17Pro; Leu17Gln; Leu17Arg; Leu17Ser; Leu17Thr; Leu17Val; Leu17Trp; Leu17Tyr; Gly18Ala; Gly18Cys; Gly18Asp; Gly18Glu; Gly18Phe; Gly18His; Gly181Ile; Gly18Lys; Gly18Leu; Gly18Met; Gly18Asn; Gly18Pro; Gly18Gln; Gly18Arg; Gly18Ser; Gly18Thr; Gly18Val; Gly18Trp; Gly18Tyr; Ile19Ala; Ile19Cys; Ile19Asp; Ile19Glu; Ile19Phe; Ile19Gly; Ile19His; Ile19Lys; Ile19Leu; Ile19Met; Ile19Asn; Ile19Pro; Ile19Gln; Ile19Arg; Ile19Ser; Ile19Thr; Ile19Val; Ile19Trp; Ile19Tyr; Phe20Ala; Phe20Cys; Phe20Asp; Phe20Glu; Phe20Gly; Phe20His; Phe20Ile; Phe20Lys; Phe20Leu; Phe20Met; Phe20Asn; Phe20Pro; Phe20Gln; Phe20Arg; Phe20Ser; Phe20Thr; Phe20Val; Phe20Trp; Phe20Tyr; Ala21Cys; Ala21Asp; Ala21Glu; Ala21Phe; Ala21Gly; Ala21His; Ala21Ile; Ala21Lys; Ala21Leu; Ala21Met; Ala21Asn; Ala21Pro; Ala21Gln; Ala21Arg; Ala21Ser; Ala21Thr; Ala21Val; Ala21Trp; Ala21Tyr; Leu22Ala; Leu22Cys; Leu22Asp; Leu22Glu; Leu22Phe; Leu22Gly; Leu22His; Leu22Ile; Leu22Lys; Leu22Met; Leu22Asn; Leu22Pro; Leu22Gln; Leu22Arg; Leu22Ser; Leu22Thr; Leu22Val; Leu22Trp; Leu22Tyr; Asp23Ala; Asp23Cys; Asp23Glu; Asp23Phe; Asp23Gly; Asp23His; Asp23Ile; Asp23Lys; Asp23Leu; Asp23Met; Asp23Asn; Asp23Pro; Asp23Gln; Asp23Arg; Asp23Ser; Asp23Thr; Asp23Val; Asp23Trp; Asp23Tyr; Thr24Ala; Thr24Cys; Thr24Asp; Thr24Glu; Thr24Phe; Thr24Gly; Thr24His; Thr24Ile; Thr24Lys; Thr24Leu; Thr24Met; Thr24Asn; Thr24Pro; Thr24Gln; Thr24Arg; Thr24Ser; Thr24Val; Thr24Trp; Thr24Tyr; Gly25Ala; Gly25Cys; Gly25Asp; Gly25Glu; Gly25Phe; Gly25His; Gly25Ile; Gly25Lys; Gly25Leu; Gly25Met; Gly25Asn; Gly25Pro; Gly25Gln; Gly25Arg; Gly25Ser; Gly25Thr; Gly25Val; Gly25Trp; Gly25Tyr; Thr26Ala; Thr26Cys; Thr26Asp; Thr26Glu; Thr26Phe; Thr26Gly; Thr26His; Thr26Ile; Thr26Lys; Thr26Leu; Thr26Met; Thr26Asn; Thr26Pro; Thr26Gln; Thr26Arg; Thr26Ser; Thr26Val; Thr26Trp; Thr26Tyr; Asn27Ala; Asn27Cys; Asn27Asp; Asn27Glu; Asn27Phe; Asn27Gly; Asn27His; Asn27Ile; Asn27Lys; Asn27Met; Asn27Asn; Asn27Pro; Asn27Gln; Asn27Arg; Asn27Ser; Asn27Thr; Asn27Val; Asn27Trp; Asn27Tyr; Arg28Ala; Arg28Cys; Arg28Asp; Arg28Glu; Arg28Phe; Arg28Gly; Arg28His; Arg28Ile; Arg28Lys; Arg28Leu; Arg28Met; Arg28Asn; Arg28Pro; Arg28Gln; Arg28Ser; Arg28Thr; Arg28Val; Arg28Trp; Arg28Tyr; Thr29Ala; Thr29Cys; Thr29Asp; Thr29Glu; Thr29Phe; Thr29Gly; Thr29His; Thr29Ile; Thr29Lys; Thr29Leu; Thr29Met; Thr29Asn; Thr29Pro; Thr29Gln; Thr29Arg; Thr29Ser; Thr29Val; Thr29Trp; Thr29Tyr; Val30Ala; Val30Cys; Val30Asp; Val30Glu; Val30Phe; Val30Gly; Val30His; Val30Ile; Val30Lys; Val30Leu; Val30Met; Val30Asn; Val30Pro; Val30Gln; Val30Arg; Val30Ser; Val30Thr; Val30Trp; Val30Tyr; Ala31Ala; Ala31Cys; Ala31Asp; Ala31Glu; Ala31Phe; Ala31Gly; Ala31His; Ala31Ile; Ala31Lys; Ala31Leu; Ala31Met; Ala31Asn; Ala31Pro; Ala31Gln; Ala31Arg; Ala31Ser; Ala31Thr; Ala31Val; Ala31Trp; Ala31Tyr; Tyr32Ala; Tyr32Cys; Tyr32Asp; Tyr32Glu; Tyr32Phe; Tyr32Gly; Tyr32His; Tyr32Ile; Tyr32Lys; Tyr32Leu; Tyr32Met; Tyr32Asn; Tyr32Pro; Tyr32Gln; Tyr32Arg; Tyr32Ser; Tyr32Thr; Tyr32Val; Tyr32Trp; Arg33Ala; Arg33Cys; Arg33Asp; Arg33Glu; Arg33Phe; Arg33Gly; Arg33His; Arg331Ile; Arg33Lys; Arg33Leu; Arg33Met; Arg33Asn; Arg33Pro; Arg33Gln; Arg33Ser; Arg33Thr; Arg33Val; Arg33Trp; Arg33Tyr; Pro34Ala; Pro34Cys; Pro34Asp; Pro34Glu; Pro34Phe; Pro34Gly; Pro34His; Pro34Ile; Pro34Lys; Pro34Leu; Pro34Met; Pro34Asn; Pro34Gln; Pro34Arg; Pro34Ser; Pro34Thr; Pro34Val; Pro34Trp; Pro34Tyr; Asp35Ala; Asp35Cys; Asp35Glu; Asp35Phe; Asp35Gly; Asp35His; Asp35Ile; Asp35Lys; Asp35Leu; Asp35Met; Asp35Asn; Asp35Pro; Asp35Gln; Asp35Arg; Asp35Ser; Asp35Thr; Asp35Val; Asp35Trp; Asp35Tyr; Glu36Ala; Glu36Cys; Glu36Asp; Glu36Phe; Glu36Gly; Glu36His; Glu36Ile; Glu36Lys; Glu36Leu; Glu36Met; Glu36Asn; Glu36Pro; Glu36Gln; Glu36Arg; Glu36Ser; Glu36Thr; Glu36Val; Glu36Trp; Glu36Tyr; Arg37Ala; Arg37Cys; Arg37Asp; Arg37Glu; Arg37Phe; Arg37Gly; Arg37His; Arg37Ile; Arg37Lys; Arg37Leu; Arg37Met; Arg37Asn; Arg37Pro; Arg37Gln; Arg37Ser; Arg37Thr; Arg37Val; Arg37Trp; Arg37Tyr; Phe38Ala; Phe38Cys; Phe38Asp; Phe38Glu; Phe38Gly; Phe38His; Phe38Ile; Phe38Lys; Phe38Leu; Phe38Met; Phe38Asn; Phe38Pro; Phe38Gln; Phe38Arg; Phe38Ser; Phe38Thr; Phe38Val; Phe38Trp;

Phe38Tyr; Ala39Cys; Ala39Asp; Ala39Glu; Ala39Phe; Ala39Gly; Ala39His; Ala39Ile; Ala39Lys; Ala39Leu; Ala39Met; Ala39Asn; Ala39Pro; Ala39Gln; Ala39Arg; Ala39Ser; Ala39Thr; Ala39Val; Ala39Trp; Ala39Tyr; Phe40Ala; Phe40Cys; Phe40Asp; Phe40Glu; Phe40Gly; Phe40His; Phe40Ile; Phe40Lys; Phe40Leu; Phe40Met; Phe40Asn; Phe40Pro; Phe40Gln; Phe40Arg; Phe40Ser; Phe40Thr; Phe40Val; Phe40Trp; Phe40Tyr; Ala41Cys; Ala41Asp; Ala41Glu; Ala41Phe; Ala41Gly; Ala41His; Ala41Ile; Ala41Lys; Ala41Leu; Ala41Met; Ala41Asn; Ala41Pro; Ala41Gln; Ala41Arg; Ala41Ser; Ala41Thr; Ala41Val; Ala41Trp; Ala41Tyr; Ser42Ala; Ser42Cys; Ser42Asp; Ser42Glu; Ser42Phe; Ser42Gly; Ser42His; Ser42Ile; Ser42Lys; Ser42Leu; Ser42Met; Ser42Asn; Ser42Pro; Ser42Gln; Ser42Arg; Ser42Thr; Ser42Val; Ser42Trp; Ser42Tyr; Thr43Ala; Thr43Cys; Thr43Asp; Thr43Glu; Thr43Phe; Thr43Gly; Thr43His; Thr43Ile; Thr43Lys; Thr43Leu; Thr43Met; Thr43Asn; Thr43Pro; Thr43Gln; Thr43Arg; Thr43Ser; Thr43Val; Thr43Trp; Thr43Tyr; Ile44Ala; Ile44Cys; Ile44Asp; Ile44Glu; Ile44Phe; Ile44Gly; Ile44His; Ile44Lys; Ile44Leu; Ile44Met; Ile44Asn; Ile44Pro; Ile44Gln; Ile44Arg; Ile44Ser; Ile44Thr; Ile44Val; Ile44Trp; Ile44Tyr; Lys45Ala; Lys45Cys; Lys45Asp; Lys45Glu; Lys45Phe; Lys45Gly; Lys45His; Lys45Ile; Lys45Leu; Lys45Met; Lys45Asn; Lys45Pro; Lys45Gln; Lys45Arg; Lys45Ser; Lys45Thr; Lys45Val; Lys45Trp; Lys45Tyr; Ala46Cys; Ala46Asp; Ala46Glu; Ala46Phe; Ala46Gly; Ala46His; Ala46Ile; Ala46Lys; Ala46Leu; Ala46Met; Ala46Asn; Ala46Pro; Ala46Gln; Ala46Arg; Ala46Ser; Ala46Thr; Ala46Val; Ala46Trp; Ala46Tyr; Leu47Ala; Leu47Cys; Leu47Asp; Leu47Glu; Leu47Phe; Leu47Gly; Leu47His; Leu47Ile; Leu47Lys; Leu47Met; Leu47Asn; Leu47Pro; Leu47Gln; Leu47Arg; Leu47Ser; Leu47Thr; Leu47Val; Leu47Trp; Leu47Tyr; Thr48Ala; Thr48Cys; Thr48Asp; Thr48Glu; Thr48Phe; Thr48Gly; Thr48His; Thr48Ile; Thr48Lys; Thr48Leu; Thr48Met; Thr48Asn; Thr48Pro; Thr48Gln; Thr48Arg; Thr48Ser; Thr48Val; Thr48Trp; Thr48Tyr; Val49Ala; Val49Cys; Val49Asp; Val49Glu; Val49Phe; Val49Gly; Val49His; Val49Ile; Val49Lys; Val49Leu; Val49Met; Val49Asn; Val49Pro; Val49Gln; Val49Arg; Val49Ser; Val49Thr; Val49Trp; Val49Tyr; Gly50Ala; Gly50Cys; Gly50Asp; Gly50Glu; Gly50Phe; Gly50His; Gly50Ile; Gly50Lys; Gly50Leu; Gly50Met; Gly50Asn; Gly50Pro; Gly50Gln; Gly50Arg; Gly50Ser; Gly50Thr; Gly50Val; Gly50Trp; Gly50Tyr; Val51Ala; Val51Cys; Val51Asp; Val51Glu; Val51Phe; Val51Gly; Val51His; Val51Ile; Val51Lys; Val51Leu; Val51Met; Val51Asn; Val51Pro; Val51Gln; Val51Arg; Val51Ser; Val51Thr; Val51Trp; Val51Tyr; Leu52Ala; Leu52Cys; Leu52Asp; Leu52Glu; Leu52Phe; Leu52Gly; Leu52His; Leu52Ile; Leu52Lys; Leu52Met; Leu52Asn; Leu52Pro; Leu52Gln; Leu52Arg; Leu52Ser; Leu52Thr; Leu52Val; Leu52Trp; Leu52Tyr; Leu53Ala; Leu53Cys; Leu53Asp; Leu53Glu; Leu53Phe; Leu53Gly; Leu53His; Leu53Ile; Leu53Lys; Leu53Met; Leu53Asn; Leu53Pro; Leu53Gln; Leu53Arg; Leu53Ser; Leu53Thr; Leu53Val; Leu53Trp; Leu53Tyr; Gln54Ala; Gln54Cys; Gln54Asp; Gln54Glu; Gln54Phe; Gln54Gly; Gln54His; Gln54Ile; Gln54Lys; Gln54Leu; Gln54Met; Gln54Asn; Gln54Pro; Gln54Arg; Gln54Ser; Gln54Thr; Gln54Val; Gln54Trp; Gln54Tyr; Gln55Ala; Gln55Cys; Gln55Asp; Gln55Glu; Gln55Phe; Gln55Gly; Gln55His; Gln55Ile; Gln55Lys; Gln55Leu; Gln55Met; Gln55Asn; Gln55Pro; Gln55Arg; Gln55Ser; Gln55Thr; Gln55Val; Gln55Trp; Gln55Tyr; Lys56Ala; Lys56Cys; Lys56Asp; Lys56Glu; Lys56Phe; Lys56Gly; Lys56His; Lys56Ile; Lys56Leu; Lys56Met; Lys56Asn; Lys56Pro; Lys56Gln; Lys56Arg; Lys56Ser; Lys56Thr; Lys56Val; Lys56Trp; Lys56Tyr; Ser57Ala; Ser57Cys; Ser57Asp; Ser57Glu; Ser57Phe; Ser57Gly; Ser57His; Ser57Ile; Ser57Lys; Ser57Leu; Ser57Met; Ser57Asn; Ser57Pro; Ser57Gln; Ser57Arg; Ser57Thr; Ser57Val; Ser57Trp; Ser57Tyr; Ile58Ala; Ile58Cys; Ile58Asp; Ile58Glu; Ile58Phe; Ile58Gly; Ile58His; Ile58Lys; Ile58Leu; Ile58Met; Ile58Asn; Ile58Pro; Ile58Gln; Ile58Arg; Ile58Ser; Ile58Thr; Ile58Val; Ile58Trp; Ile58Tyr; Glu59Ala; Glu59Cys; Glu59Asp; Glu59Phe; Glu59Gly; Glu59His; Glu59Ile; Glu59Lys; Glu59Leu; Glu59Met; Glu59Asn; Glu59Pro; Glu59Gln; Glu59Arg; Glu59Ser; Glu59Thr; Glu59Val; Glu59Trp; Glu59Tyr; Asp60Ala; Asp60Cys; Asp60Glu; Asp60Phe; Asp60Gly; Asp60His; Asp60Ile; Asp60Lys; Asp60Leu; Asp60Met; Asp60Asn; Asp60Pro; Asp60Gln; Asp60Arg; Asp60Ser; Asp60Thr; Asp60Val; Asp60Trp; Asp60Tyr; Leu61Ala; Leu61Cys; Leu61Asp; Leu61Glu; Leu61Phe; Leu61Gly; Leu61His; Leu61Ile; Leu61Lys; Leu61Met; Leu61Asn; Leu61Pro; Leu61Gln; Leu61Arg; Leu61Ser; Leu61Thr; Leu61Val; Leu61Trp; Leu61Tyr; Asn62Ala; Asn62Cys; Asn62Asp; Asn62Glu; Asn62Phe; Asn62Gly; Asn62His; Asn62Ile; Asn62Lys; Asn62Leu; Asn62Met; Asn62Pro; Asn62Gln; Asn62Arg; Asn62Ser; Asn62Thr; Asn62Val; Asn62Trp; Asn62Tyr; Gln63Ala; Gln63Cys; Gln63Asp; Gln63Glu; Gln63Phe; Gln63Gly; Gln63His; Gln63Ile; Gln63Lys; Gln63Leu; Gln63Met; Gln63Asn; Gln63Pro; Gln63Arg; Gln63Ser; Gln63Thr; Gln63Val; Gln63Trp; Gln63Tyr; Arg64Ala; Arg64Cys; Arg64Asp; Arg64Glu; Arg64Phe; Arg64Gly; Arg64His; Arg64Ile; Arg64Lys; Arg64Leu; Arg64Met; Arg64Asn; Arg64Pro; Arg64Gln; Arg64Ser; Arg64Thr; Arg64Val; Arg64Trp; Arg64Tyr; Ile65Ala; Ile65Cys; Ile65Asp; Ile65Glu; Ile65Phe; Ile65Gly; Ile65His; Ile65Lys; Ile65Leu; Ile65Met; Ile65Asn; Ile65Pro; Ile65Gln; Ile65Arg; Ile65Ser; Ile65Thr; Ile65Val; Ile65Trp; Ile65Tyr; Thr66Ala; Thr66Cys; Thr66Asp; Thr66Glu; Thr66Phe; Thr66Gly; Thr66His; Thr66Ile; Thr66Lys; Thr66Leu; Thr66Met; Thr66Asn; Thr66Pro; Thr66Gln; Thr66Arg; Thr66Ser; Thr66Val; Thr66Trp; Thr66Tyr; Tyr67Ala; Tyr67Cys; Tyr67Asp; Tyr67Glu; Tyr67Phe; Tyr67Gly; Tyr67His; Tyr67Ile; Tyr67Lys; Tyr67Leu; Tyr67Met; Tyr67Asn; Tyr67Pro; Tyr67Gln; Tyr67Arg; Tyr67Ser; Tyr67Thr; Tyr67Val; Tyr67Trp; Thr68Ala; Thr68Cys; Thr68Asp; Thr68Glu; Thr68Phe; Thr68Gly; Thr68His; Thr68Ile; Thr68Lys; Thr68Leu; Thr68Met; Thr68Asn; Thr68Pro; Thr68Gln; Thr68Arg; Thr68Ser; Thr68Val; Thr68Trp; Thr68Tyr; Arg69Ala; Arg69Cys; Arg69Asp; Arg69Glu; Arg69Phe; Arg69Gly; Arg69His; Arg69Ile; Arg69Lys; Arg69Leu; Arg69Met; Arg69Asn; Arg69Pro; Arg69Gln; Arg69Ser; Arg69Thr; Arg69Val; Arg69Trp; Arg69Tyr; Asp70Ala; Asp70Cys; Asp70Glu; Asp70Phe; Asp70Gly; Asp70His; Asp70Ile; Asp70Lys; Asp70Leu; Asp70Met; Asp70Asn; Asp70Pro; Asp70Gln; Asp70Arg; Asp70Ser; Asp70Thr; Asp70Val; Asp70Trp; Asp70Tyr; Asp71Ala; Asp71Cys; Asp71Glu; Asp71Phe; Asp71Gly; Asp71His; Asp71Ile; Asp71Lys; Asp71Leu; Asp71Met; Asp71Asn; Asp71Pro; Asp71Gln; Asp71Arg; Asp71Ser; Asp71Thr; Asp71Val; Asp71Trp; Asp71Tyr; Leu72Ala; Leu72Cys; Leu72Asp; Leu72Glu; Leu72Phe; Leu72Gly; Leu72His; Leu72Ile; Leu72Lys; Leu72Met; Leu72Asn; Leu72Pro; Leu72Gln; Leu72Arg; Leu72Ser; Leu72Thr; Leu72Val; Leu72Trp; Leu72Tyr; Val73Ala; Val73Cys; Val73Asp; Val73Glu; Val73Phe; Val73Gly; Val73His; Val73Ile; Val73Lys; Val73Leu; Val73Met; Val73Asn; Val73Pro; Val73Gln; Val73Arg; Val73Ser; Val73Thr; Val73Trp; Val73Tyr; Asn74Ala; Asn74Cys; Asn74Asp; Asn74Glu; Asn74Phe; Asn74Gly; Asn74His; Asn74Ile; Asn74Lys;

Asn74Leu; Asn74Met; Asn74Pro; Asn74Gln; Asn74Arg; Asn74Ser; Asn74Thr; Asn74Val; Asn74Trp; Asn74Tyr; Tyr75Ala; Tyr75Cys; Tyr75Asp; Tyr75Glu; Tyr75Phe; Tyr75Gly; Tyr75His; Tyr75Ile; Tyr75Leu; Tyr75Lys; Tyr75Met; Tyr75Pro; Tyr75Asn; Tyr75Gln; Tyr75Arg; Tyr75Ser; Tyr75Thr; Tyr75Val; Tyr75Trp; Asn76Ala; Asn76Cys; Asn76Asp; Asn76Glu; Asn76Phe; Asn76Gly; Asn76His; Asn76Ile; Asn76Lys; Asn76Leu; Asn76Met; Asn76Pro; Asn76Gln; Asn76Arg; Asn76Ser; Asn76Thr; Asn76Val; Asn76Trp; Asn76Tyr; Pro77Ala; Pro77Cys; Pro77Asp; Pro77Glu; Pro77Phe; Pro77Gly; Pro77His; Pro77Ile; Pro77Lys; Pro77Leu; Pro77Met; Pro77Asn; Pro77Gln; Pro77Arg; Pro77Ser; Pro77Thr; Pro77Val; Pro77Trp; Pro77Tyr; Ile78Ala; Ile78Cys; Ile78Asp; Ile78Glu; Ile78Phe; Ile78Gly; Ile78His; Ile78Lys; Ile78Leu; Ile78Met; Ile78Asn; Ile78Pro; Ile78Gln; Ile78Arg; Ile78Ser; Ile78Thr; Ile78Val; Ile78Trp; Ile78Tyr; Thr79Ala; Thr79Cys; Thr79Asp; Thr79Glu; Thr79Phe; Thr79Gly; Thr79His; Thr79Ile; Thr79Lys; Thr79Leu; Thr79Met; Thr79Asn; Thr79Pro; Thr79Gln; Thr79Arg; Thr79Ser; Thr79Val; Thr79Trp; Thr79Tyr; Glu80Ala; Glu80Cys; Glu80Asp; Glu80Phe; Glu80Gly; Glu80His; Glu80Ile; Glu80Lys; Glu80Leu; Glu80Met; Glu80Asn; Glu80Pro; Glu80Gln; Glu80Arg; Glu80Ser; Glu80Thr; Glu80Val; Glu80Trp; Glu80Tyr; Lys81Ala; Lys81Cys; Lys81Asp; Lys81Glu; Lys81Phe; Lys81Gly; Lys81His; Lys81Ile; Lys81Leu; Lys81Met; Lys81Asn; Lys81Pro; Lys81Gln; Lys81Arg; Lys81Ser; Lys81Thr; Lys81Val; Lys81Trp; Lys81Tyr; His82Ala; His82Cys; His82Asp; His82Glu; His82Phe; His82Gly; His82Ile; His82Lys; His82Leu; His82Met; His82Asn; His82Pro; His82Gln; His82Arg; His82Ser; His82Thr; His82Val; His82Trp; His82Tyr; Val83Ala; Val83Cys; Val83Asp; Val83Glu; Val83Phe; Val83Gly; Val83His; Val83Ile; Val83Lys; Val83Leu; Val83Met; Val83Asn; Val83Pro; Val83Gln; Val83Arg; Val83Ser; Val83Thr; Val83Trp; Val83Tyr; Asp84Ala; Asp84Cys; Asp84Glu; Asp84Phe; Asp84Gly; Asp84His; Asp84Ile; Asp84Lys; Asp84Leu; Asp84Met; Asp84Asn; Asp84Pro; Asp84Gln; Asp84Arg; Asp84Ser; Asp84Thr; Asp84Val; Asp84Trp; Asp84Tyr; Thr85Ala; Thr85Cys; Thr85Asp; Thr85Glu; Thr85Phe; Thr85Gly; Thr85His; Thr85Ile; Thr85Lys; Thr85Leu; Thr85Met; Thr85Asn; Thr85Pro; Thr85Gln; Thr85Arg; Thr85Ser; Thr85Val; Thr85Trp; Thr85Tyr; Gly86Ala; Gly86Cys; Gly86Asp; Gly86Glu; Gly86Phe; Gly86His; Gly86Ile; Gly86Lys; Gly86Leu; Gly86Met; Gly86Asn; Gly86Pro; Gly86Gln; Gly86Arg; Gly86Ser; Gly86Thr; Gly86Val; Gly86Trp; Gly86Tyr; Met87Ala; Met87Cys; Met87Asp; Met87Glu; Met87Phe; Met87Gly; Met87His; Met87Ile; Met87Lys; Met87Leu; Met87Asn; Met87Pro; Met87Gln; Met87Arg; Met87Ser; Met87Thr; Met87Val; Met87Trp; Met87Tyr; Thr88Ala; Thr88Cys; Thr88Asp; Thr88Glu; Thr88Phe; Thr88Gly; Thr88His; Thr88Ile; Thr88Lys; Thr88Leu; Thr88Met; Thr88Asn; Thr88Pro; Thr88Gln; Thr88Arg; Thr88Ser; Thr88Val; Thr88Trp; Thr88Tyr; Leu89Ala; Leu89Cys; Leu89Asp; Leu89Glu; Leu89Phe; Leu89Gly; Leu89His; Leu89Ile; Leu89Lys; Leu89Met; Leu89Asn; Leu89Pro; Leu89Gln; Leu89Arg; Leu89Ser; Leu89Thr; Leu89Val; Leu89Trp; Leu89Tyr; Lys90Ala; Lys90Cys; Lys90Asp; Lys90Glu; Lys90Phe; Lys90Gly; Lys90His; Lys90Ile; Lys90Leu; Lys90Met; Lys90Asn; Lys90Pro; Lys90Gln; Lys90Arg; Lys90Ser; Lys90Thr; Lys90Val; Lys90Trp; Lys90Tyr; Glu91Ala; Glu91Cys; Glu91Asp; Glu91Phe; Glu91Gly; Glu91His; Glu91Ile; Glu91Lys; Glu91Leu; Glu91Met; Glu91Asn; Glu91Pro; Glu91Gln; Glu91Arg; Glu91Ser; Glu91Thr; Glu91Val; Glu91Trp; Glu91Tyr; Leu92Ala; Leu92Cys; Leu92Asp; Leu92Glu; Leu92Phe; Leu92Gly; Leu92His; Leu92Ile; Leu92Lys; Leu92Met; Leu92Asn; Leu92Pro; Leu92Gln; Leu92Arg; Leu92Ser; Leu92Thr; Leu92Val; Leu92Trp; Leu92Tyr; Ala93Cys; Ala93Asp; Ala93Glu; Ala93Phe; Ala93Gly; Ala93His; Ala93Ile; Ala93Lys; Ala93Leu; Ala93Met; Ala93Asn; Ala93Pro; Ala93Gln; Ala93Arg; Ala93Ser; Ala93Thr; Ala93Val; Ala93Trp; Ala93Tyr; Asp94Ala; Asp94Cys; Asp94Glu; Asp94Phe; Asp94Gly; Asp94His; Asp94Ile; Asp94Lys; Asp94Leu; Asp94Met; Asp94Asn; Asp94Pro; Asp94Gln; Asp94Arg; Asp94Ser; Asp94Thr; Asp94Val; Asp94Trp; Asp94Tyr; Ala95Cys; Ala95Asp; Ala95Glu; Ala95Phe; Ala95Gly; Ala95His; Ala95Ile; Ala95Lys; Ala95Leu; Ala95Met; Ala95Asn; Ala95Pro; Ala95Gln; Ala95Arg; Ala95Ser; Ala95Thr; Ala95Val; Ala95Trp; Ala95Tyr; Ser96Ala; Ser96Cys; Ser96Asp; Ser96Glu; Ser96Phe; Ser96Gly; Ser96His; Ser96Ile; Ser96Lys; Ser96Leu; Ser96Met; Ser96Asn; Ser96Pro; Ser96Gln; Ser96Arg; Ser96Thr; Ser96Val; Ser96Trp; Ser96Tyr; Leu97Ala; Leu97Cys; Leu97Asp; Leu97Glu; Leu97Phe; Leu97Gly; Leu97His; Leu97Ile; Leu97Lys; Leu97Met; Leu97Asn; Leu97Pro; Leu97Gln; Leu97Arg; Leu97Ser; Leu97Thr; Leu97Val; Leu97Trp; Leu97Tyr; Arg98Ala; Arg98Cys; Arg98Asp; Arg98Glu; Arg98Phe; Arg98Gly; Arg98His; Arg98Ile; Arg98Lys; Arg98Leu; Arg98Met; Arg98Asn; Arg98Pro; Arg98Gln; Arg98Ser; Arg98Thr; Arg98Val; Arg98Trp; Arg98Tyr; Tyr99Ala; Tyr99Cys; Tyr99Asp; Tyr99Glu; Tyr99Phe; Tyr99Gly; Tyr99His; Tyr99Ile; Tyr99Lys; Tyr99Leu; Tyr99Met; Tyr99Asn; Tyr99Pro; Tyr99Gln; Tyr99Arg; Tyr99Ser; Tyr99Thr; Tyr99Val; Tyr99Trp; Ser100Ala; Ser100Cys; Ser100Asp; Ser100Glu; Ser100Phe; Ser100Gly; Ser100His; Ser100Ile; Ser100Lys; Ser100Leu; Ser100Met; Ser100Asn; Ser100Pro; Ser100Gln; Ser100Arg; Ser100Thr; Ser100Val; Ser100Trp; Ser100Tyr; Asp101Ala; Asp101Cys; Asp101Glu; Asp101Phe; Asp101Gly; Asp101His; Asp101Ile; Asp101Lys; Asp101Leu; Asp101Met; Asp101Asn; Asp101Pro; Asp101Gln; Asp101Arg; Asp101Ser; Asp101Thr; Asp101Val; Asp101Trp; Asp101Tyr; Asn102Ala; Asn102Cys; Asn102Asp; Asn102Glu; Asn102Phe; Asn102Gly; Asn102His; Asn102Ile; Asn102Lys; Asn102Leu; Asn102Met; Asn102Pro; Asn102Gln; Asn102Arg; Asn102Ser; Asn102Thr; Asn102Val; Asn102Trp; Asn102Tyr; Ala103Cys; Ala103Asp; Ala103Glu; Ala103Phe; Ala103Gly; Ala103His; Ala103Ile; Ala103Lys; Ala103Leu; Ala103Met; Ala103Asn; Ala103Pro; Ala103Gln; Ala103Arg; Ala103Ser; Ala103Thr; Ala103Val; Ala103Trp; Ala103Tyr; Ala104Cys; Ala104Asp; Ala104Glu; Ala104Phe; Ala104Gly; Ala104His; Ala104Ile; Ala104Lys; Ala104Leu; Ala104Met; Ala104Asn; Ala104Pro; Ala104Gln; Ala104Arg; Ala104Ser; Ala104Thr; Ala104Val; Ala104Trp; Ala104Tyr; Gln105Ala; Gln105Cys; Gln105Asp; Gln105Glu; Gln105Phe; Gln105Gly; Gln105His; Gln105Ile; Gln105Lys; Gln105Leu; Gln105Met; Gln105Asn; Gln105Pro; Gln105Arg; Gln105Ser; Gln105Thr; Gln105Val; Gln105Trp; Gln105Tyr; Asn106Ala; Asn106Cys; Asn106Asp; Asn106Glu; Asn106Phe; Asn106Gly; Asn106His; Asn1061Ile; Asn106Lys; Asn106Leu; Asn106Met; Asn106Pro; Asn106Gln; Asn106Arg; Asn106Ser; Asn106Thr; Asn106Val; Asn106Trp; Asn106Tyr; Leu107Ala; Leu107Cys; Leu107Asp; Leu107Glu; Leu107Phe; Leu107Gly; Leu107His; Leu1071Ile; Leu107Lys; Leu107Met; Leu107Asn; Leu107Pro; Leu107Gln; Leu107Arg; Leu107Ser; Leu107Thr; Leu107Val; Leu107Trp; Leu107Tyr; Ile108Ala; Ile108Cys; Ile108Asp; Ile108Glu; Ile108Phe; Ile108Gly; Ile108His;

Ile108Lys; Ile108Leu; Ile108Met; Ile108Asn; Ile108Pro; Ile108Gln; Ile108Arg; Ile108Ser; Ile108Thr; Ile108Val; Ile108Trp; Ile108Tyr; Leu109Ala; Leu109Cys; Leu109Asp; Leu109Glu; Leu109Phe; Leu109Gly; Leu109His; Leu109Ile; Leu109Lys; Leu109Met; Leu109Asn; Leu109Pro; Leu109Gln; Leu109Arg; Leu109Ser; Leu109Thr; Leu109Val; Leu109Trp; Leu109Tyr; Lys110Ala; Lys110Cys; Lys110Asp; Lys110Glu; Lys110Phe; Lys110Gly; Lys110His; Lys110Ile; Lys110Leu; Lys110Met; Lys110Asn; Lys110Pro; Lys110Gln; Lys110Arg; Lys110Ser; Lys110Thr; Lys110Val; Lys110Trp; Lys110Tyr; Gln111Ala; Gln111Cys; Gln111Asp; Gln111Glu; Gln111Phe; Gln111Gly; Gln111His; Gln111Ile; Gln111Lys; Gln111Leu; Gln111Met; Gln111Asn; Gln111Pro; Gln111Arg; Gln111Ser; Gln111Thr; Gln111Val; Gln111Trp; Gln111Tyr; Ile112Ala; Ile112Cys; Ile112Asp; Ile112Glu; Ile112Phe; Ile112Gly; Ile112His; Ile112Lys; Ile112Leu; Ile112Met; Ile112Asn; Ile112Pro; Ile112Gln; Ile112Arg; Ile112Ser; Ile112Thr; Ile112Val; Ile112Trp; Ile112Tyr; Gly113Ala; Gly113Cys; Gly113Asp; Gly113Glu; Gly113Phe; Gly113His; Gly113Ile; Gly113Lys; Gly113Leu; Gly113Met; Gly113Asn; Gly113Pro; Gly113Gln; Gly113Arg; Gly113Ser; Gly113Thr; Gly113Val; Gly113Trp; Gly113Tyr; Gly114Ala; Gly114Cys; Gly114Asp; Gly114Glu; Gly114Phe; Gly114His; Gly114Ile; Gly114Lys; Gly114Leu; Gly114Met; Gly114Asn; Gly114Pro; Gly114Gln; Gly114Arg; Gly114Ser; Gly114Thr; Gly114Val; Gly114Trp; Gly114Tyr; Pro115Ala; Pro115Cys; Pro115Asp; Pro115Glu; Pro115Phe; Pro115Gly; Pro115His; Pro115Ile; Pro115Lys; Pro115Leu; Pro115Met; Pro115Asn; Pro115Gln; Pro115Arg; Pro115Ser; Pro115Thr; Pro115Val; Pro115Trp; Pro115Tyr; Glu116Ala; Glu116Cys; Glu116Asp; Glu116Phe; Glu116Gly; Glu116His; Glu116Ile; Glu116Lys; Glu116Leu; Glu116Met; Glu116Asn; Glu116Pro; Glu116Gln; Glu116Arg; Glu116Ser; Glu116Thr; Glu116Val; Glu116Trp; Glu116Tyr; Ser117Ala; Ser117Cys; Ser117Asp; Ser117Glu; Ser117Phe; Ser117Gly; Ser117His; Ser117Ile; Ser117Lys; Ser117Leu; Ser117Met; Ser117Asn; Ser117Pro; Ser117Gln; Ser117Arg; Ser117Thr; Ser117Val; Ser117Trp; Ser117Tyr; Leu118Ala; Leu118Cys; Leu118Asp; Leu118Glu; Leu118Phe; Leu118Gly; Leu118His; Leu118Ile; Leu118Lys; Leu118Met; Leu118Asn; Leu118Pro; Leu118Gln; Leu118Arg; Leu118Ser; Leu118Thr; Leu118Val; Leu118Trp; Leu118Tyr; Lys119Ala; Lys119Cys; Lys119Asp; Lys119Glu; Lys119Phe; Lys119Gly; Lys119His; Lys119Ile; Lys119Leu; Lys119Met; Lys119Asn; Lys119Pro; Lys119Gln; Lys119Arg; Lys119Ser; Lys119Thr; Lys119Val; Lys119Trp; Lys119Tyr; Lys120Ala; Lys120Cys; Lys120Asp; Lys120Glu; Lys120Phe; Lys120Gly; Lys120His; Lys120Ile; Lys120Leu; Lys120Met; Lys120Asn; Lys120Pro; Lys120Gln; Lys120Arg; Lys120Ser; Lys120Thr; Lys120Val; Lys120Trp; Lys120Tyr; Glu121Ala; Glu121Cys; Glu121Asp; Glu121Phe; Glu121Gly; Glu121His; Glu121Ile; Glu121Lys; Glu121Leu; Glu121Met; Glu121Asn; Glu121Pro; Glu121Gln; Glu121Arg; Glu121Ser; Glu121Thr; Glu121Val; Glu121Trp; Glu121Tyr; Leu122Ala; Leu122Cys; Leu122Asp; Leu122Glu; Leu122Phe; Leu122Gly; Leu122His; Leu122Ile; Leu122Lys; Leu122Met; Leu122Asn; Leu122Pro; Leu122Gln; Leu122Arg; Leu122Ser; Leu122Thr; Leu122Val; Leu122Trp; Leu122Tyr; Arg123Ala; Arg123Cys; Arg123Asp; Arg123Glu; Arg123Phe; Arg123Gly; Arg123His; Arg123Ile; Arg123Lys; Arg123Leu; Arg123Met; Arg123Asn; Arg123Pro; Arg123Gln; Arg123Ser; Arg123Thr; Arg123Val; Arg123Trp; Arg123Tyr; Lys124Ala; Lys124Cys; Lys124Asp; Lys124Glu; Lys124Phe; Lys124Gly; Lys124His; Lys124Ile; Lys124Leu; Lys124Met; Lys124Asn; Lys124Pro; Lys124Gln; Lys124Arg; Lys124Ser; Lys124Thr; Lys124Val; Lys124Trp; Lys124Tyr; Ile125Ala; Ile125Cys; Ile125Asp; Ile125Glu; Ile125Phe; Ile125Gly; Ile125His; Ile125Lys; Ile125Leu; Ile125Met; Ile125Asn; Ile125Pro; Ile125Gln; Ile125Arg; Ile125Ser; Ile125Thr; Ile125Val; Ile125Trp; Ile125Tyr; Gly126Ala; Gly126Cys; Gly126Asp; Gly126Glu; Gly126Phe; Gly126His; Gly126Ile; Gly126Lys; Gly126Leu; Gly126Met; Gly126Asn; Gly126Pro; Gly126Gln; Gly126Arg; Gly126Ser; Gly126Thr; Gly126Val; Gly126Trp; Gly126Tyr; Asp127Ala; Asp127Cys; Asp127Glu; Asp127Phe; Asp127Gly; Asp127His; Asp127Ile; Asp127Lys; Asp127Leu; Asp127Met; Asp127Asn; Asp127Pro; Asp127Gln; Asp127Arg; Asp127Ser; Asp127Thr; Asp127Val; Asp127Trp; Asp127Tyr; Glu128Ala; Glu128Cys; Glu128Asp; Glu128Phe; Glu128Gly; Glu128His; Glu128Ile; Glu128Lys; Glu128Leu; Glu128Met; Glu128Asn; Glu128Pro; Glu128Gln; Glu128Arg; Glu128Ser; Glu128Thr; Glu128Val; Glu128Trp; Glu128Tyr; Val129Ala; Val129Cys; Val129Asp; Val129Glu; Val129Phe; Val129Gly; Val129His; Val129Ile; Val129Lys; Val129Leu; Val129Met; Val129Asn; Val129Pro; Val129Gln; Val129Arg; Val129Ser; Val129Thr; Val129Trp; Val129Tyr; Thr130Ala; Thr130Cys; Thr130Asp; Thr130Glu; Thr130Phe; Thr130Gly; Thr130His; Thr130Ile; Thr130Lys; Thr130Leu; Thr130Met; Thr130Asn; Thr130Pro; Thr130Gln; Thr130Arg; Thr130Ser; Thr130Val; Thr130Trp; Thr130Tyr; Asn131Ala; Asn131Cys; Asn131Asp; Asn131Glu; Asn131Phe; Asn131Gly; Asn131His; Asn131Ile; Asn131Lys; Asn131Leu; Asn131Met; Asn131Pro; Asn131Gln; Asn131Arg; Asn131Ser; Asn131Thr; Asn131Val; Asn131Trp; Asn131Tyr; Pro132Ala; Pro132Cys; Pro132Asp; Pro132Glu; Pro132Phe; Pro132Gly; Pro132His; Pro132Ile; Pro132Lys; Pro132Leu; Pro132Met; Pro132Asn; Pro132Gln; Pro132Arg; Pro132Ser; Pro132Thr; Pro132Val; Pro132Trp; Pro132Tyr; Glu133Ala; Glu133Cys; Glu133Asp; Glu133Phe; Glu133Gly; Glu133His; Glu133Ile; Glu133Lys; Glu133Leu; Glu133Met; Glu133Asn; Glu133Pro; Glu133Gln; Glu133Arg; Glu133Ser; Glu133Thr; Glu133Val; Glu133Trp; Glu133Tyr; Arg134Ala; Arg134Cys; Arg134Asp; Arg134Glu; Arg134Phe; Arg134Gly; Arg134His; Arg134Ile; Arg134Lys; Arg134Leu; Arg134Met; Arg134Asn; Arg134Pro; Arg134Gln; Arg134Ser; Arg134Thr; Arg134Val; Arg134Trp; Arg134Tyr; Phe135Ala; Phe135Cys; Phe135Asp; Phe135Glu; Phe135Gly; Phe135His; Phe135Ile; Phe135Lys; Phe135Leu; Phe135Met; Phe135Asn; Phe135Pro; Phe135Gln; Phe135Arg; Phe135Ser; Phe135Thr; Phe135Val; Phe135Trp; Phe135Tyr; Glu136Ala; Glu136Cys; Glu136Asp; Glu136Phe; Glu136Gly; Glu136His; Glu136Ile; Glu136Lys; Glu136Leu; Glu136Met; Glu136Asn; Glu136Pro; Glu136Gln; Glu136Arg; Glu136Ser; Glu136Thr; Glu136Val; Glu136Trp; Glu136Tyr; Pro137Ala; Pro137Cys; Pro137Asp; Pro137Glu; Pro137Phe; Pro137Gly; Pro137His; Pro137Ile; Pro137Lys; Pro137Leu; Pro137Met; Pro137Asn; Pro137Gln; Pro137Arg; Pro137Ser; Pro137Thr; Pro137Val; Pro137Trp; Pro137Tyr; Glu138Ala; Glu138Cys; Glu138Asp; Glu138Phe; Glu138Gly; Glu138His; Glu138Ile; Glu138Lys; Glu138Leu;

Glu138Met; Glu138Asn; Glu138Pro; Glu138Gln; Glu138Arg; Glu138Ser; Glu138Thr; Glu138Val; Glu138Trp; Glu138Tyr; Leu139Ala; Leu139Cys; Leu139Asp; Leu139Glu; Leu139Phe; Leu139Gly; Leu139His; Leu139Ile; Leu139Lys; Leu139Met; Leu139Asn; Leu139Pro; Leu139Gln; Leu139Arg; Leu139Ser; Leu139Thr; Leu139Val; Leu139Trp; Leu139Tyr; Asn140Ala; Asn140Cys; Asn140Asp; Asn140Glu; Asn140Phe; Asn140Gly; Asn140His; Asn140Ile; Asn140Lys; Asn140Leu; Asn140Met; Asn140Pro; Asn140Gln; Asn140Arg; Asn140Ser; Asn140Thr; Asn140Val; Asn140Trp; Asn140Tyr; Glu141Ala; Glu141Cys; Glu141Asp; Glu141Phe; Glu141Gly; Glu141His; Glu14Ile; Glu141Lys; Glu141Leu; Glu141Met; Glu141Asn; Glu141Pro; Glu141Gln; Glu141Arg; Glu141Ser; Glu141Thr; Glu141Val; Glu141Trp; Glu141Tyr; Val142Ala; Val1142Cys; Val1142Asp; Val142Glu; Val142Phe; Val142Gly; Val 142His; Val 142Ile; Val 142Lys; Val 142Leu; Val 142Met; Val 142Asn; Val 142Pro; Val 142Gln; Val 142Arg; Val 142Ser; Val142Thr; Val142Trp; Val142Tyr; Asn143Ala; Asn143Cys; Asn143Asp; Asn143Glu; Asn143Phe; Asn143Gly; Asn143His; Asn143Ile; Asn143Lys; Asn143Leu; Asn143Met; Asn143Pro; Asn143Gln; Asn143Arg; Asn143Ser; Asn143Thr; Asn143Val; Asn143Trp; Asn143Tyr; Pro144Ala; Pro144Cys; Pro144Asp; Pro144Glu; Pro144Phe; Pro144Gly; Pro144His; Pro144Ile; Pro144Lys; Pro144Leu; Pro144Met; Pro144Asn; Pro144Gln; Pro144Arg; Pro144Ser; Pro144Thr; Pro144Val; Pro144Trp; Pro144Tyr; Gly145Ala; Gly145Cys; Gly145Asp; Gly145Glu; Gly145Phe; Gly145His; Gly145Ile; Gly145Lys; Gly145Leu; Gly145Met; Gly145Asn; Gly145Pro; Gly145Gln; Gly145Arg; Gly145Ser; Gly145Thr; Gly145Val; Gly145Trp; Gly145Tyr; Glu146Ala; Glu146Cys; Glu146Asp; Glu146Phe; Glu146Gly; Glu146His; Glu146Ile; Glu146Lys; Glu146Leu; Glu146Met; Glu146Asn; Glu146Pro; Glu146Gln; Glu146Arg; Glu146Ser; Glu146Thr; Glu146Val; Glu146Trp; Glu146Tyr; Thr147Ala; Thr147Cys; Thr147Asp; Thr147Glu; Thr147Phe; Thr147Gly; Thr147His; Thr147Ile; Thr147Lys; Thr147Leu; Thr147Met; Thr147Asn; Thr147Pro; Thr147Gln; Thr147Arg; Thr147Ser; Thr147Val; Thr147Trp; Thr147Tyr; Gln148Ala; Gln148Cys; Gln148Asp; Gln148Glu; Gln148Phe; Gln148Gly; Gln148His; Gln148Ile; Gln148Lys; Gln148Leu; Gln148Met; Gln148Asn; Gln148Pro; Gln148Arg; Gln148Ser; Gln148Thr; Gln148Val; Gln148Trp; Gln148Tyr; Asp149Ala; Asp149Cys; Asp149Glu; Asp149Phe; Asp149Gly; Asp149His; Asp149Ile; Asp149Lys; Asp149Leu; Asp149Met; Asp149Asn; Asp149Pro; Asp149Gln; Asp149Arg; Asp149Ser; Asp149Thr; Asp149Val; Asp149Trp; Asp149Tyr; Thr150Ala; Thr150Cys; Thr150Asp; Thr150Glu; Thr150Phe; Thr150Gly; Thr150His; Thr150Ile; Thr150Lys; Thr150Leu; Thr150Met; Thr150Asn; Thr150Pro; Thr150Gln; Thr150Arg; Thr150Ser; Thr150Val; Thr150Trp; Thr150Tyr; Ser151Ala; Ser151Cys; Ser151Asp; Ser151Glu; Ser151Phe; Ser151Gly; Ser151His; Ser151Ile; Ser151Lys; Ser151Leu; Ser151Met; Ser151Asn; Ser151Pro; Ser151Gln; Ser151Arg; Ser151Thr; Ser151Val; Ser151Trp; Ser151Tyr; Thr152Ala; Thr152Cys; Thr152Asp; Thr152Glu; Thr152Phe; Thr152Gly; Thr152His; Thr152Ile; Thr152Lys; Thr152Leu; Thr152Met; Thr152Asn; Thr152Pro; Thr152Gln; Thr152Arg; Thr152Ser; Thr152Val; Thr152Trp; Thr152Tyr; Ala153Cys; Ala153Asp; Ala153Glu; Ala153Phe; Ala153Gly; Ala153His; Ala153Ile; Ala153Lys; Ala153Leu; Ala153Met; Ala153Asn; Ala153Pro; Ala153Gln; Ala153Arg; Ala153Ser; Ala153Thr; Ala153Val; Ala153Trp; Ala153Tyr; Arg154Ala; Arg154Cys; Arg154Asp; Arg154Glu; Arg154Phe; Arg154Gly; Arg154His; Arg154Ile; Arg154Lys; Arg154Leu; Arg154Met; Arg154Asn; Arg154Pro; Arg154Gln; Arg154Ser; Arg154Thr; Arg154Val; Arg154Trp; Arg154Tyr; Ala155Cys; Ala155Asp; Ala155Glu; Ala155Phe; Ala155Gly; Ala155His; Ala155Ile; Ala155Lys; Ala155Leu; Ala155Met; Ala155Asn; Ala155Pro; Ala155Gln; Ala155Arg; Ala155Ser; Ala155Thr; Ala155Val; Ala155Trp; Ala155Tyr; Leu156Ala; Leu156Cys; Leu156Asp; Leu156Glu; Leu156Phe; Leu156Gly; Leu156His; Leu156Ile; Leu156Lys; Leu156Met; Leu156Asn; Leu156Pro; Leu156Gln; Leu156Arg; Leu156Ser; Leu156Thr; Leu156Val; Leu156Trp; Leu156Tyr; Val157Ala; Val1157Cys; Val1157Asp; Val157Glu; Val157Phe; Val157Gly; Val157His; Val157Ile; Val157Lys; Val157Leu; Val157Met; Val157Asn; Val157Pro; Val157Gln; Val157Arg; Val157Ser; Val157Thr; Val157Trp; Val157Tyr; Thr158Ala; Thr158Cys; Thr158Asp; Thr158Glu; Thr158Phe; Thr158Gly; Thr158His; Thr158Ile; Thr158Lys; Thr158Leu; Thr158Met; Thr158Asn; Thr158Pro; Thr158Gln; Thr158Arg; Thr158Ser; Thr158Val; Thr158Trp; Thr158Tyr; Ser159Ala; Ser159Cys; Ser159Asp; Ser159Glu; Ser159Phe; Ser159Gly; Ser159His; Ser159Ile; Ser159Lys; Ser159Leu; Ser159Met; Ser159Asn; Ser159Pro; Ser159Gln; Ser159Arg; Ser159Thr; Ser159Val; Ser159Trp; Ser159Tyr; Leu160Ala; Leu160Cys; Leu160Asp; Leu160Glu; Leu160Phe; Leu160Gly; Leu160His; Leu160Ile; Leu160Lys; Leu160Met; Leu160Asn; Leu160Pro; Leu160Gln; Leu160Arg; Leu160Ser; Leu160Thr; Leu160Val; Leu160Trp; Leu160Tyr; Arg161Ala; Arg161Cys; Arg161Asp; Arg161Glu; Arg161Phe; Arg161Gly; Arg161His; Arg161Ile; Arg161Lys; Arg161Leu; Arg161Met; Arg161Asn; Arg161Pro; Arg161Gln; Arg161Ser; Arg161Thr; Arg161Val; Arg161Trp; Arg161Tyr; Ala162Cys; Ala162Asp; Ala162Glu; Ala162Phe; Ala162Gly; Ala162His; Ala162Ile; Ala162Lys; Ala162Leu; Ala162Met; Ala162Asn; Ala162Pro; Ala162Gln; Ala162Arg; Ala162Ser; Ala162Thr; Ala162Val; Ala162Trp; Ala162Tyr; Phe163Ala; Phe163Cys; Phe163Asp; Phe163Glu; Phe163Gly; Phe163His; Phe163Ile; Phe163Lys; Phe163Leu; Phe163Met; Phe163Asn; Phe163Pro; Phe163Gln; Phe163Arg; Phe163Ser; Phe163Thr; Phe163Val; Phe163Trp; Phe163Tyr; Ala164Cys; Ala164Asp; Ala164Glu; Ala164Phe; Ala164Gly; Ala164His; Ala164Ile; Ala164Lys; Ala164Leu; Ala164Met; Ala164Asn; Ala164Pro; Ala164Gln; Ala164Arg; Ala164Ser; Ala164Thr; Ala164Val; Ala164Trp; Ala164Tyr; Leu165Ala; Leu165Cys; Leu165Asp; Leu165Glu; Leu165Phe; Leu165Gly; Leu165His; Leu165Ile; Leu165Lys; Leu165Met; Leu165Asn; Leu165Pro; Leu165Gln; Leu165Arg; Leu165Ser; Leu165Thr; Leu165Val; Leu165Trp; Leu165Tyr; Glu166Ala; Glu166Cys; Glu166Asp; Glu166Phe; Glu166Gly; Glu166His; Glu166Ile; Glu166Lys; Glu166Leu; Glu166Met; Glu166Asn; Glu166Pro; Glu166Gln; Glu166Arg; Glu166Ser; Glu166Thr; Glu166Val; Glu166Trp; Glu166Tyr; Asp167Ala; Asp167Cys; Asp167Glu; Asp167Phe; Asp167Gly; Asp167His; Asp167Ile; Asp167Lys; Asp167Leu; Asp167Met; Asp167Asn; Asp167Pro; Asp167Gln; Asp167Arg; Asp167Ser; Asp167Thr; Asp167Val; Asp167Trp; Asp167Tyr; Lys168Ala; Lys168Cys; Lys168Asp; Lys168Glu; Lys168Phe; Lys168Gly; Lys168His; Lys168Ile;

Lys168Leu; Lys168Met; Lys168Asn; Lys168Pro; Lys168Gln; Lys168Arg; Lys168Ser; Lys168Thr; Lys168Val; Lys168Trp; Lys168Tyr; Leu169Ala; Leu169Cys; Leu169Asp; Leu169Glu; Leu169Phe; Leu169Gly; Leu169His; Leu169Ile; Leu169Lys; Leu169Met; Leu169Asn; Leu169Pro; Leu169Gln; Leu169Arg; Leu169Ser; Leu169Thr; Leu169Val; Leu169Trp; Leu169Tyr; Pro170Ala; Pro170Cys; Pro170Asp; Pro170Glu; Pro170Phe; Pro170Gly; Pro170His; Pro170Ile; Pro170Lys; Pro170Leu; Pro170Met; Pro170Asn; Pro170Gln; Pro170Arg; Pro170Ser; Pro170Thr; Pro170Val; Pro170Trp; Pro170Tyr; Ser171Ala; Ser171Cys; Ser171Asp; Ser171Glu; Ser171Phe; Ser171Gly; Ser171His; Ser171Ile; Ser171Lys; Ser171Leu; Ser171Met; Ser171Asn; Ser171Pro; Ser171Gln; Ser171Arg; Ser171Thr; Ser171Val; Ser171Trp; Ser171Tyr; Glu172Ala; Glu172Cys; Glu172Asp; Glu172Phe; Glu172Gly; Glu172His; Glu172Ile; Glu172Lys; Glu172Leu; Glu172Met; Glu172Asn; Glu172Pro; Glu172Gln; Glu172Arg; Glu172Ser; Glu172Thr; Glu172Val; Glu172Trp; Glu172Tyr; Lys173Ala; Lys173Cys; Lys173Asp; Lys173Glu; Lys173Phe; Lys173Gly; Lys173His; Lys173Ile; Lys173Leu; Lys173Met; Lys173Asn; Lys173Pro; Lys173Gln; Lys173Arg; Lys173Ser; Lys173Thr; Lys173Val; Lys173Trp; Lys173Tyr; Arg174Ala; Arg174Cys; Arg174Asp; Arg174Glu; Arg174Phe; Arg174Gly; Arg174His; Arg174Ile; Arg174Lys; Arg174Leu; Arg174Met; Arg174Asn; Arg174Pro; Arg174Gln; Arg174Ser; Arg174Thr; Arg174Val; Arg174Trp; Arg174Tyr; Glu175Ala; Glu175Cys; Glu175Asp; Glu175Phe; Glu175Gly; Glu175His; Glu175Ile; Glu175Lys; Glu175Leu; Glu175Met; Glu175Asn; Glu175Pro; Glu175Gln; Glu175Arg; Glu175Ser; Glu175Thr; Glu175Val; Glu175Trp; Glu175Tyr; Leu176Ala; Leu176Cys; Leu176Asp; Leu176Glu; Leu176Phe; Leu176Gly; Leu176His; Leu176Ile; Leu176Lys; Leu176Met; Leu176Asn; Leu176Pro; Leu176Gln; Leu176Arg; Leu176Ser; Leu176Thr; Leu176Val; Leu176Trp; Leu176Tyr; Leu177Ala; Leu177Cys; Leu177Asp; Leu177Glu; Leu177Phe; Leu177Gly; Leu177His; Leu177Ile; Leu177Lys; Leu177Met; Leu177Asn; Leu177Pro; Leu177Gln; Leu177Arg; Leu177Ser; Leu177Thr; Leu177Val; Leu177Trp; Leu177Tyr; Ile178Ala; Ile178Cys; Ile178Asp; Ile178Glu; Ile178Phe; Ile178Gly; Ile178His; Ile178Lys; Ile178Leu; Ile178Met; Ile178Asn; Ile178Pro; Ile178Gln; Ile178Arg; Ile178Ser; Ile178Thr; Ile178Val; Ile178Trp; Ile178Tyr; Asp179Ala; Asp179Cys; Asp179Glu; Asp179Phe; Asp179Gly; Asp179His; Asp179Ile; Asp179Lys; Asp179Leu; Asp179Met; Asp179Asn; Asp179Pro; Asp179Gln; Asp179Arg; Asp179Ser; Asp179Thr; Asp179Val; Asp179Trp; Asp179Tyr; Trp180Ala; Trp180Cys; Trp180Asp; Trp180Glu; Trp180Phe; Trp180Gly; Trp180His; Trp180Ile; Trp180Lys; Trp180Leu; Trp180Met; Trp180Asn; Trp180Pro; Trp180Gln; Trp180Arg; Trp180Ser; Trp180Thr; Trp180Val; Trp180Tyr; Met181Ala; Met181Cys; Met181Asp; Met181Glu; Met181Phe; Met181Gly; Met181His; Met18Ile; Met181Lys; Met181Leu; Met181Asn; Met181Pro; Met181Gln; Met181Arg; Met181Ser; Met181Thr; Met181Val; Met181Trp; Met181Tyr; Lys182Ala; Lys182Cys; Lys182Asp; Lys182Glu; Lys182Phe; Lys182Gly; Lys182His; Lys182Ile; Lys182Leu; Lys182Met; Lys182Asn; Lys182Pro; Lys182Gln; Lys182Arg; Lys182Ser; Lys182Thr; Lys182Val; Lys182Tyr; Lys182Trp; Arg183Ala; Arg183Cys; Arg183Asp; Arg183Glu; Arg183Phe; Arg183Gly; Arg183His; Arg183Ile; Arg183Lys; Arg183Leu; Arg183Met; Arg183Asn; Arg183Pro; Arg183Gln; Arg183Ser; Arg183Thr; Arg183Val; Arg183Trp; Arg183Tyr; Asn184Ala; Asn184Cys; Asn184Asp; Asn184Glu; Asn184Phe; Asn184Gly; Asn184His; Asn184Ile; Asn184Lys; Asn184Leu; Asn184Met; Asn184Pro; Asn184Gln; Asn184Arg; Asn184Ser; Asn184Thr; Asn184Val; Asn184Trp; Asn184Tyr; Thr185Ala; Thr185Cys; Thr185Asp; Thr185Glu; Thr185Phe; Thr185Gly; Thr185His; Thr185Ile; Thr185Lys; Thr185Leu; Thr185Met; Thr185Asn; Thr185Pro; Thr185Gln; Thr185Arg; Thr185Ser; Thr185Val; Thr185Trp; Thr185Tyr; Thr186Ala; Thr186Cys; Thr186Asp; Thr186Glu; Thr186Phe; Thr186Gly; Thr186His; Thr186Ile; Thr186Lys; Thr186Leu; Thr186Met; Thr186Asn; Thr186Pro; Thr186Gln; Thr186Arg; Thr186Ser; Thr186Val; Thr186Trp; Thr186Tyr; Gly187Ala; Gly187Cys; Gly187Asp; Gly187Glu; Gly187Phe; Gly187His; Gly187Ile; Gly187Lys; Gly187Leu; Gly187Met; Gly187Asn; Gly187Pro; Gly187Gln; Gly187Arg; Gly187Ser; Gly187Thr; Gly187Val; Gly187Trp; Gly187Tyr; Asp188Ala; Asp188Cys; Asp188Glu; Asp188Phe; Asp188Gly; Asp188His; Asp188Ile; Asp188Lys; Asp188Leu; Asp188Met; Asp188Asn; Asp188Pro; Asp188Gln; Asp188Arg; Asp188Ser; Asp188Thr; Asp188Val; Asp188Trp; Asp188Tyr; Ala189Cys; Ala189Asp; Ala189Glu; Ala189Phe; Ala189Gly; Ala189His; Ala189Ile; Ala189Lys; Ala189Leu; Ala189Met; Ala189Asn; Ala189Pro; Ala189Gln; Ala189Arg; Ala189Ser; Ala189Thr; Ala189Val; Ala189Trp; Ala189Tyr; Leu190Ala; Leu190Cys; Leu190Asp; Leu190Glu; Leu190Phe; Leu190Gly; Leu190His; Leu190Ile; Leu190Lys; Leu190Met; Leu190Asn; Leu190Pro; Leu190Gln; Leu190Arg; Leu190Ser; Leu190Thr; Leu190Val; Leu190Trp; Leu190Tyr; Ile191Ala; Ile191Cys; Ile191Asp; Ile191Glu; Ile191Phe; Ile191Gly; Ile191His; Ile191Lys; Ile191Leu; Ile191Met; Ile191Asn; Ile191Pro; Ile191Gln; Ile191Arg; Ile191Ser; Ile191Thr; Ile191Val; Ile191Trp; Ile191Tyr; Arg192Ala; Arg192Cys; Arg192Asp; Arg192Glu; Arg192Phe; Arg192Gly; Arg192His; Arg192Ile; Arg192Lys; Arg192Leu; Arg192Met; Arg192Asn; Arg192Pro; Arg192Gln; Arg192Ser; Arg192Thr; Arg192Val; Arg192Trp; Arg192Tyr; Ala193Cys; Ala193Asp; Ala193Glu; Ala193Phe; Ala193Gly; Ala193His; Ala193Ile; Ala193Lys; Ala193Leu; Ala193Met; Ala193Asn; Ala193Pro; Ala193Gln; Ala193Arg; Ala193Ser; Ala193Thr; Ala193Val; Ala193Trp; Ala193Tyr; Gly194Ala; Gly194Cys; Gly194Asp; Gly194Glu; Gly194Phe; Gly194His; Gly194Ile; Gly194Lys; Gly194Leu; Gly194Met; Gly194Asn; Gly194Pro; Gly194Gln; Gly194Arg; Gly194Ser; Gly194Thr; Gly194Val; Gly194Trp; Gly194Tyr; Val195Ala; Val195Cys; Val195Asp; Val195Glu; Val195Phe; Val195Gly; Val195His; Vail95Ile; Val 195Lys; Val 195Leu; Val 195Met; Val 195Asn; Val 195Pro; Val 195Gln; Val 195Arg; Val 195Ser; Val195Thr; Val195Trp; Val195Tyr; Pro196Ala; Pro196Cys; Pro196Asp; Pro196Glu; Pro196Phe; Pro196Gly; Pro196His; Pro196Ile; Pro196Lys; Pro196Leu; Pro196Met; Pro196Asn; Pro196Gln; Pro196Arg; Pro196Ser; Pro196Thr; Pro196Val; Pro196Trp; Pro196Tyr; Asp197Ala; Asp197Cys; Asp197Glu; Asp197Phe; Asp197Gly; Asp197His; Asp197Ile; Asp197Lys; Asp197Leu; Asp197Met; Asp197Asn; Asp197Pro; Asp197Gln; Asp197Arg; Asp197Ser; Asp197Thr; Asp197Val; Asp197Trp; Asp197Tyr; Gly198Ala; Gly198Cys; Gly198Asp; Gly198Glu; Gly198Phe; Gly198His;

Gly198Ile; Gly198Lys; Gly198Leu; Gly198Met; Gly198Asn; Gly198Pro; Gly198Gln; Gly198Arg; Gly198Ser; Gly198Thr; Gly198Val; Gly198Trp; Gly198Tyr; Trp199Ala; Trp199Cys; Trp199Asp; Trp199Glu; Trp199Phe; Trp199Gly; Trp199His; Trp199Ile; Trp199Lys; Trp199Leu; Trp199Met; Trp199Asn; Trp199Pro; Trp199Gln; Trp199Arg; Trp199Ser; Trp199Thr; Trp199Val; Trp199Tyr; Glu200Ala; Glu200Cys; Glu200Asp; Glu200Phe; Glu200Gly; Glu200His; Glu200Ile; Glu200Lys; Glu200Leu; Glu200Met; Glu200Asn; Glu200Pro; Glu200Gln; Glu200Arg; Glu200Ser; Glu200Thr; Glu200Val; Glu200Trp; Glu200Tyr; Val201Ala; Val201Cys; Val201Asp; Val201Glu; Val201Phe; Val201Gly; Val201His; Val20Ile; Val201Lys; Val201Leu; Val201Met; Val201Asn; Val201Pro; Val201Gln; Val201Arg; Val201Ser; Val201Thr; Val201Trp; Val201Tyr; Ala202Cys; Ala202Asp; Ala202Glu; Ala202Phe; Ala202Gly; Ala202His; Ala202Ile; Ala202Lys; Ala202Leu; Ala202Met; Ala202Asn; Ala202Pro; Ala202Gln; Ala202Arg; Ala202Ser; Ala202Thr; Ala202Val; Ala202Trp; Ala202Tyr; Asp203Ala; Asp203Cys; Asp203Glu; Asp203Phe; Asp203Gly; Asp203His; Asp203Ile; Asp203Lys; Asp203Leu; Asp203Met; Asp203Asn; Asp203Pro; Asp203Gln; Asp203Arg; Asp203Ser; Asp203Thr; Asp203Val; Asp203Trp; Asp203Tyr; Lys204Ala; Lys204Cys; Lys204Asp; Lys204Glu; Lys204Phe; Lys204Gly; Lys204His; Lys204Ile; Lys204Leu; Lys204Met; Lys204Asn; Lys204Pro; Lys204Gln; Lys204Arg; Lys204Ser; Lys204Thr; Lys204Val; Lys204Trp; Lys204Tyr; Thr205Ala; Thr205Cys; Thr205Asp; Thr205Glu; Thr205Phe; Thr205Gly; Thr205His; Thr205Ile; Thr205Lys; Thr205Leu; Thr205Met; Thr205Asn; Thr205Pro; Thr205Gln; Thr205Arg; Thr205Ser; Thr205Val; Thr205Trp; Thr205Tyr; Gly206Ala; Gly206Cys; Gly206Asp; Gly206Glu; Gly206Phe; Gly206His; Gly206Ile; Gly206Lys; Gly206Leu; Gly206Met; Gly206Asn; Gly206Pro; Gly206Gln; Gly206Arg; Gly206Ser; Gly206Thr; Gly206Val; Gly206Trp; Gly206Tyr; Ala207Cys; Ala207Asp; Ala207Glu; Ala207Phe; Ala207Gly; Ala207His; Ala207Ile; Ala207Lys; Ala207Leu; Ala207Met; Ala207Asn; Ala207Pro; Ala207Gln; Ala207Arg; Ala207Ser; Ala207Thr; Ala207Val; Ala207Trp; Ala207Tyr; Ala208Cys; Ala208Asp; Ala208Glu; Ala208Phe; Ala208Gly; Ala208His; Ala208Ile; Ala208Lys; Ala208Leu; Ala208Met; Ala208Asn; Ala208Pro; Ala208Gln; Ala208Arg; Ala208Ser; Ala208Thr; Ala208Val; Ala208Trp; Ala208Tyr; Ser209Ala; Ser209Cys; Ser209Asp; Ser209Glu; Ser209Phe; Ser209Gly; Ser209His; Ser209Ile; Ser209Lys; Ser209Leu; Ser209Met; Ser209Asn; Ser209Pro; Ser209Gln; Ser209Arg; Ser209Thr; Ser209Val; Ser209Trp; Ser209Tyr; Tyr210Ala; Tyr210Cys; Tyr210Asp; Tyr210Glu; Tyr210Phe; Tyr210Gly; Tyr210His; Tyr210Ile; Tyr210Lys; Tyr210Leu; Tyr210Met; Tyr210Asn; Tyr210Pro; Tyr210Gln; Tyr210Arg; Tyr210Ser; Tyr210Thr; Tyr210Val; Tyr210Trp; Gly211Ala; Gly211Cys; Gly211Asp; Gly211Glu; Gly211Phe; Gly211His; Gly211Ile; Gly211Lys; Gly211Leu; Gly211Met; Gly211Asn; Gly211Pro; Gly211Gln; Gly211Arg; Gly211Ser; Gly211Thr; Gly211Val; Gly211Trp; Gly211Tyr; Thr212Ala; Thr212Cys; Thr212Asp; Thr212Glu; Thr212Phe; Thr212Gly; Thr212His; Thr212Ile; Thr212Lys; Thr212Leu; Thr212Met; Thr212Asn; Thr212Pro; Thr212Gln; Thr212Arg; Thr212Ser; Thr212Val; Thr212Trp; Thr212Tyr; Arg213Ala; Arg213Cys; Arg213Asp; Arg213Glu; Arg213Phe; Arg213Gly; Arg213His; Arg213Ile; Arg213Lys; Arg213Leu; Arg213Met; Arg213Asn; Arg213Pro; Arg213Gln; Arg213Ser; Arg213Thr; Arg213Val; Arg213Trp; Arg213Tyr; Asn214Ala; Asn214Cys; Asn214Asp; Asn214Glu; Asn214Phe; Asn214Gly; Asn214His; Asn214Ile; Asn214Lys; Asn214Leu; Asn214Met; Asn214Pro; Asn214Gln; Asn214Arg; Asn214Ser; Asn214Thr; Asn214Val; Asn214Trp; Asn214Tyr; Asp215Ala; Asp215Cys; Asp215Glu; Asp215Phe; Asp215Gly; Asp215His; Asp215Ile; Asp215Lys; Asp215Leu; Asp215Met; Asp215Asn; Asp215Pro; Asp215Gln; Asp215Arg; Asp215Ser; Asp215Thr; Asp215Val; Asp215Trp; Asp215Tyr; Ile216Ala; Ile216Cys; Ile216Asp; Ile216Glu; Ile216Phe; Ile216Gly; Ile216His; Ile216Lys; Ile216Leu; Ile216Met; Ile216Asn; Ile216Pro; Ile216Gln; Ile216Arg; Ile216Ser; Ile216Thr; Ile216Val; Ile216Trp; Ile216Tyr; Ala217Cys; Ala217Asp; Ala217Glu; Ala217Phe; Ala217Gly; Ala217His; Ala217Ile; Ala217Lys; Ala217Leu; Ala217Met; Ala217Asn; Ala217Pro; Ala217Gln; Ala217Arg; Ala217Ser; Ala217Thr; Ala217Val; Ala217Trp; Ala217Tyr; Ile218Ala; Ile218Cys; Ile218Asp; Ile218Glu; Ile218Phe; Ile218Gly; Ile218His; Ile218Lys; Ile218Leu; Ile218Met; Ile218Asn; Ile218Pro; Ile218Gln; Ile218Arg; Ile218Ser; Ile218Thr; Ile218Val; Ile218Trp; Ile218Tyr; Ile219Ala; Ile219Cys; Ile219Asp; Ile219Glu; Ile219Phe; Ile219Gly; Ile219His; Ile219Lys; Ile219Leu; Ile219Met; Ile219Asn; Ile219Pro; Ile219Gln; Ile219Arg; Ile219Ser; Ile219Thr; Ile219Val; Ile219Trp; Ile219Tyr; Trp220Ala; Trp220Cys; Trp220Asp; Trp220Glu; Trp220Phe; Trp220Gly; Trp220His; Trp220Ile; Trp220Lys; Trp220Leu; Trp220Met; Trp220Asn; Trp220Pro; Trp220Gln; Trp220Arg; Trp220Ser; Trp220Thr; Trp220Val; Trp220Tyr; Pro221Ala; Pro221Cys; Pro221Asp; Pro221Glu; Pro221Phe; Pro221Gly; Pro221His; Pro221Ile; Pro221Lys; Pro221Leu; Pro221Met; Pro221Asn; Pro221Gln; Pro221Arg; Pro221Ser; Pro221Thr; Pro221Val; Pro221Trp; Pro221Tyr; Pro222Ala; Pro222Cys; Pro222Asp; Pro222Glu; Pro222Phe; Pro222Gly; Pro222His; Pro222Ile; Pro222Lys; Pro222Leu; Pro222Met; Pro222Asn; Pro222Gln; Pro222Arg; Pro222Ser; Pro222Thr; Pro222Val; Pro222Trp; Pro222Tyr; Lys223Ala; Lys223Cys; Lys223Asp; Lys223Glu; Lys223Phe; Lys223Gly; Lys223His; Lys223Ile; Lys223Leu; Lys223Met; Lys223Asn; Lys223Pro; Lys223Gln; Lys223Arg; Lys223Ser; Lys223Thr; Lys223Val; Lys223Trp; Lys223Tyr; Gly224Ala; Gly224Cys; Gly224Asp; Gly224Glu; Gly224Phe; Gly224His; Gly224Ile; Gly224Lys; Gly224Leu; Gly224Met; Gly224Asn; Gly224Pro; Gly224Gln; Gly224Arg; Gly224Ser; Gly224Thr; Gly224Val; Gly224Trp; Gly224Tyr; Asp225Ala; Asp225Cys; Asp225Glu; Asp225Phe; Asp225Gly; Asp225His; Asp225Ile; Asp225Lys; Asp225Leu; Asp225Met; Asp225Asn; Asp225Pro; Asp225Gln; Asp225Arg; Asp225Ser; Asp225Thr; Asp225Val; Asp225Trp; Asp225Tyr; Pro226Ala; Pro226Cys; Pro226Asp; Pro226Glu; Pro226Phe; Pro226Gly; Pro226His; Pro226Ile; Pro226Lys; Pro226Leu; Pro226Met; Pro226Asn; Pro226Gln; Pro226Arg; Pro226Ser; Pro226Thr; Pro226Val; Pro226Trp; Pro226Tyr; Val227Ala; Val227Cys; Val227Asp; Val227Glu; Val227Phe; Val227Gly; Val227His; Val227Ile; Val227Lys; Val227Leu; Val227Met; Val227Asn; Val227Pro; Val227Gln; Val227Arg; Val227Ser; Val227Thr; Val227Trp; Val227Tyr; Val228Ala; Val228Cys; Val228Asp; Val228Glu; Val228Phe; Val228Gly; Val228His; Val228Ile; Val228Lys; Val228Leu; Val228Met; Val228Asn; Val228Pro; Val228Gln; Val228Arg; Val228Ser; Val228Thr; Val228Trp; Val228Tyr; Leu229Ala; Leu229Cys; Leu229Asp; Leu229Glu; Leu229Phe; Leu229Gly; Leu229His; Leu229Ile; Leu229Lys; Leu229Met;

Leu229Asn; Leu229Pro; Leu229Gln; Leu229Arg; Leu229Ser; Leu229Thr; Leu229Val; Leu229Trp; Leu229Tyr; Ala230Cys; Ala230Asp; Ala230Glu; Ala230Phe; Ala230Gly; Ala230His; Ala230Ile; Ala230Lys; Ala230Leu; Ala230Met; Ala230Asn; Ala230Pro; Ala230Gln; Ala230Arg; Ala230Ser; Ala230Thr; Ala230Val; Ala230Trp; Ala230Tyr; Val231Ala; Val231Cys; Val231Asp; Val231Glu; Val231Phe; Val231Gly; Val231His; Val231Ile; Val231Lys; Val231Leu; Val231Met; Val231Asn; Val231Pro; Val231Gln; Val231Arg; Val231Ser; Val231Thr; Val231Trp; Val231Tyr; Leu232Ala; Leu232Cys; Leu232Asp; Leu232Glu; Leu232Phe; Leu232Gly; Leu232His; Leu232Ile; Leu232Lys; Leu232Met; Leu232Asn; Leu232Pro; Leu232Gln; Leu232Arg; Leu232Ser; Leu232Thr; Leu232Val; Leu232Trp; Leu232Tyr; Ser233Ala; Ser233Cys; Ser233Asp; Ser233Glu; Ser233Phe; Ser233Gly; Ser233His; Ser233Ile; Ser233Lys; Ser233Leu; Ser233Met; Ser233Asn; Ser233Pro; Ser233Gln; Ser233Arg; Ser233Thr; Ser233Val; Ser233Trp; Ser233Tyr; Ser234Ala; Ser234Cys; Ser234Asp; Ser234Glu; Ser234Phe; Ser234Gly; Ser234His; Ser234Ile; Ser234Lys; Ser234Leu; Ser234Met; Ser234Asn; Ser234Pro; Ser234Gln; Ser234Arg; Ser234Thr; Ser234Val; Ser234Trp; Ser234Tyr; Arg235Ala; Arg235Cys; Arg235Asp; Arg235Glu; Arg235Phe; Arg235Gly; Arg235His; Arg235Ile; Arg235Lys; Arg235Leu; Arg235Met; Arg235Asn; Arg235Pro; Arg235Gln; Arg235Ser; Arg235Thr; Arg235Val; Arg235Trp; Arg235Tyr; Asp236Ala; Asp236Cys; Asp236Glu; Asp236Phe; Asp236Gly; Asp236His; Asp236Ile; Asp236Lys; Asp236Leu; Asp236Met; Asp236Asn; Asp236Pro; Asp236Gln; Asp236Arg; Asp236Ser; Asp236Thr; Asp236Val; Asp236Trp; Asp236Tyr; Lys237Ala; Lys237Cys; Lys237Asp; Lys237Glu; Lys237Phe; Lys237Gly; Lys237His; Lys237Ile; Lys237Leu; Lys237Met; Lys237Asn; Lys237Pro; Lys237Gln; Lys237Arg; Lys237Ser; Lys237Thr; Lys237Val; Lys237Trp; Lys237Tyr; Lys238Ala; Lys238Cys; Lys238Asp; Lys238Glu; Lys238Phe; Lys238Gly; Lys238His; Lys238Ile; Lys238Leu; Lys238Met; Lys238Asn; Lys238Pro; Lys238Gln; Lys238Arg; Lys238Ser; Lys238Thr; Lys238Val; Lys238Trp; Lys238Tyr; Asp239Ala; Asp239Cys; Asp239Glu; Asp239Phe; Asp239Gly; Asp239His; Asp239Ile; Asp239Lys; Asp239Leu; Asp239Met; Asp239Asn; Asp239Pro; Asp239Gln; Asp239Arg; Asp239Ser; Asp239Thr; Asp239Val; Asp239Trp; Asp239Tyr; Ala240Cys; Ala240Asp; Ala240Glu; Ala240Phe; Ala240Gly; Ala240His; Ala240Ile; Ala240Lys; Ala240Leu; Ala240Met; Ala240Asn; Ala240Pro; Ala240Gln; Ala240Arg; Ala240Ser; Ala240Thr; Ala240Val; Ala240Trp; Ala240Tyr; Lys241Ala; Lys241Cys; Lys241Asp; Lys241Glu; Lys241Phe; Lys241Gly; Lys241His; Lys241Ile; Lys241Leu; Lys241Met; Lys241Asn; Lys241Pro; Lys241Gln; Lys241Arg; Lys241Ser; Lys241Thr; Lys241Val; Lys241Trp; Lys241Tyr; Tyr242Ala; Tyr242Cys; Tyr242Asp; Tyr242Glu; Tyr242Phe; Tyr242Gly; Tyr242His; Tyr242Ile; Tyr242Lys; Tyr242Leu; Tyr242Met; Tyr242Asn; Tyr242Pro; Tyr242Gln; Tyr242Arg; Tyr242Ser; Tyr242Thr; Tyr242Val; Tyr242Trp; Asp243Ala; Asp243Cys; Asp243Glu; Asp243Phe; Asp243Gly; Asp243His; Asp243Ile; Asp243Lys; Asp243Leu; Asp243Met; Asp243Asn; Asp243Pro; Asp243Gln; Asp243Arg; Asp243Ser; Asp243Thr; Asp243Val; Asp243Trp; Asp243Tyr; Asp244Ala; Asp244Cys; Asp244Glu; Asp244Phe; Asp244Gly; Asp244His; Asp244Ile; Asp244Lys; Asp244Leu; Asp244Met; Asp244Asn; Asp244Pro; Asp244Gln; Asp244Arg; Asp244Ser; Asp244Thr; Asp244Val; Asp244Trp; Asp244Tyr; Lys245Ala; Lys245Cys; Lys245Asp; Lys245Glu; Lys245Phe; Lys245Gly; Lys245His; Lys245Ile; Lys245Leu; Lys245Met; Lys245Asn; Lys245Pro; Lys245Gln; Lys245Arg; Lys245Ser; Lys245Thr; Lys245Val; Lys245Trp; Lys245Tyr; Leu246Ala; Leu246Cys; Leu246Asp; Leu246Glu; Leu246Phe; Leu246Gly; Leu246His; Leu246Ile; Leu246Lys; Leu246Met; Leu246Asn; Leu246Pro; Leu246Gln; Leu246Arg; Leu246Ser; Leu246Thr; Leu246Val; Leu246Trp; Leu246Tyr; Ile247Ala; Ile247Cys; Ile247Asp; Ile247Glu; Ile247Phe; Ile247Gly; Ile247His; Ile247Lys; Ile247Leu; Ile247Met; Ile247Asn; Ile247Pro; Ile247Gln; Ile247Arg; Ile247Ser; Ile247Thr; Ile247Val; Ile247Trp; Ile247Tyr; Ala248Cys; Ala248Asp; Ala248Glu; Ala248Phe; Ala248Gly; Ala248His; Ala248Ile; Ala248Lys; Ala248Leu; Ala248Met; Ala248Asn; Ala248Pro; Ala248Gln; Ala248Arg; Ala248Ser; Ala248Thr; Ala248Val; Ala248Trp; Ala248Tyr; Glu249Ala; Glu249Cys; Glu249Asp; Glu249Phe; Glu249Gly; Glu249His; Glu249Ile; Glu249Lys; Glu249Leu; Glu249Met; Glu249Asn; Glu249Pro; Glu249Gln; Glu249Arg; Glu249Ser; Glu249Thr; Glu249Val; Glu249Trp; Glu249Tyr; Ala250Cys; Ala250Asp; Ala250Glu; Ala250Phe; Ala250Gly; Ala250His; Ala250Ile; Ala250Lys; Ala250Leu; Ala250Met; Ala250Asn; Ala250Pro; Ala250Gln; Ala250Arg; Ala250Ser; Ala250Thr; Ala250Val; Ala250Trp; Ala250Tyr; Thr251Ala; Thr251Cys; Thr251Asp; Thr251Glu; Thr251Phe; Thr251Gly; Thr251His; Thr251Ile; Thr251Lys; Thr251Leu; Thr251Met; Thr251Asn; Thr251Pro; Thr251Gln; Thr251Arg; Thr251Ser; Thr251Val; Thr251Trp; Thr251Tyr; Lys252Ala; Lys252Cys; Lys252Asp; Lys252Glu; Lys252Phe; Lys252Gly; Lys252His; Lys252Ile; Lys252Leu; Lys252Met; Lys252Asn; Lys252Pro; Lys252Gln; Lys252Arg; Lys252Ser; Lys252Thr; Lys252Val; Lys252Trp; Lys252Tyr; Val253Ala; Val253Cys; Val253Asp; Val253Glu; Val253Phe; Val253Gly; Val253His; Val253Ile; Val253Lys; Val253Leu; Val253Met; Val253Asn; Val253Pro; Val253Gln; Val253Arg; Val253Ser; Val253Thr; Val253Trp; Val253Tyr; Val254Ala; Val254Cys; Val254Asp; Val254Glu; Val254Phe; Val254Gly; Val254His; Val254Ile; Val254Lys; Val254Leu; Val254Met; Val254Asn; Val254Pro; Val254Gln; Val254Arg; Val254Ser; Val254Thr; Val254Trp; Val254Tyr; Met255Ala; Met255Cys; Met255Asp; Met255Glu; Met255Phe; Met255Gly; Met255His; Met255Ile; Met255Lys; Met255Leu; Met255Asn; Met255Pro; Met255Gln; Met255Arg; Met255Ser; Met255Thr; Met255Val; Met255Trp; Met255Tyr; Lys256Ala; Lys256Cys; Lys256Asp; Lys256Glu; Lys256Phe; Lys256Gly; Lys256His; Lys256Ile; Lys256Leu; Lys256Met; Lys256Asn; Lys256Pro; Lys256Gln; Lys256Arg; Lys256Ser; Lys256Thr; Lys256Val; Lys256Trp; Lys256Tyr; Ala257Cys; Ala257Asp; Ala257Glu; Ala257Phe; Ala257Gly; Ala257His; Ala257Ile; Ala257Lys; Ala257Leu; Ala257Met; Ala257Asn; Ala257Pro; Ala257Gln; Ala257Arg; Ala257Ser; Ala257Thr; Ala257Val; Ala257Trp; Ala257Tyr; Leu258Ala; Leu258Cys; Leu258Asp; Leu258Glu; Leu258Phe; Leu258Gly; Leu258His; Leu258Ile; Leu258Lys; Leu258Met; Leu258Asn; Leu258Pro; Leu258Gln; Leu258Arg; Leu258Ser; Leu258Thr; Leu258Val; Leu258Trp; Leu258Tyr; Asn259Ala; Asn259Cys; Asn259Asp; Asn259Glu; Asn259Phe; Asn259Gly; Asn259His; Asn259Ile; Asn259Lys; Asn259Leu; Asn259Met; Asn259Pro; Asn259Gln; Asn259Arg; Asn259Ser; Asn259Thr; Asn259Val; Asn259Trp; Asn259Tyr;

Met260Ala; Met260Cys; Met260Asp; Met260Glu; Met260Phe; Met260Gly; Met260His; Met260Ile; Met260Lys; Met260Leu; Met260Asn; Met260Pro; Met260Gln; Met260Arg; Met260Ser; Met260Thr; Met260Val; Met260Trp; Met260Tyr; Asn261Ala; Asn261Cys; Asn261Asp; Asn261Glu; Asn261Phe; Asn261Gly; Asn261His; Asn261Ile; Asn261Lys; Asn261Leu; Asn261Met; Asn261Pro; Asn261Gln; Asn261Arg; Asn261Ser; Asn261Thr; Asn261Val; Asn261Trp; Asn261Tyr; Gly262Ala; Gly262Cys; Gly262Asp; Gly262Glu; Gly262Phe; Gly262His; Gly262Ile; Gly262Lys; Gly262Leu; Gly262Met; Gly262Asn; Gly262Pro; Gly262Gln; Gly262Arg; Gly262Ser; Gly262Thr; Gly262Val; Gly262Trp; Gly262Tyr; Lys263Ala; Lys263Cys; Lys263Asp; Lys263Glu; Lys263Phe; Lys263Gly; Lys263His; Lys263Ile; Lys263Leu; Lys263Met; Lys263Asn; Lys263Pro; Lys263Gln; Lys263Arg; Lys263Ser; Lys263Thr; Lys263Val; Lys263Trp; Lys263Tyr; Met 264Ala; Met 264Cys; Met 264Asp; Met 264Glu; Met 264Phe; Met 264Gly; Met 264His; Met 264Ile; Met 264Lys; Met 264Leu; Met 264Asn; Met 264Pro; Met 264Gln; Met 264Arg; Met 264Ser; Met 264Thr; Met 264Val; Met 264Trp; Met 264Tyr; Asn 265Ala; Asn 265Cys; Asn 265Asp; Asn 265Glu; Asn 265Phe; Asn 265Gly; Asn 265His; Asn 265Ile; Asn 265Lys; Asn 265Leu; Asn 265Met; Asn 265Pro; Asn 265Gln; Asn 265Arg; Asn 265Ser; Asn 265Thr; Asn 265Val; Asn 265Trp; Asn 265Tyr; Gly 266Ala; Gly 266Cys; Gly 266Asp; Gly 266Glu; Gly 266Phe; Gly 266His; Gly 266Ile; Gly 266Lys; Gly 266Leu; Gly 266Met; Gly 266Asn; Gly 266Pro; Gly 266Gln; Gly 266Arg; Gly 266Ser; Gly 266Thr; Gly 266Val; Gly 266Trp; Gly 266Tyr; Lys267Ala; Lys267Cys; Lys267Asp; Lys267Glu; Lys267Phe; Lys267Gly; Lys267His; Lys267Ile; Lys267Leu; Lys267Met; Lys267Asn; Lys267Pro; Lys267Gln; Lys267Arg; Lys267Ser; Lys267Thr; Lys267Val; Lys267Trp; and Lys267Tyr. In some embodiments, SEQ ID NO: 1 may have a Met and/or Thr preceeding the first residue of the sequence. These residues may be similarly mutated as above.

In all of these mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All). For example, residue 244 corresponds to Ambler 276. For example, the following conversions may be used:

| Ambler Classification No. | SEQ ID NO: 1 Residue |
|---|---|
| F33 | F6 |
| I72 | I44 |
| Q135 | Q105 |
| G156 | G126 |
| T160 | T130 |
| A232 | A202 |
| A237 | A207 |
| A238 | A208 |
| S240 | S209 |
| T243 | T212 |
| R244 | R213 |
| S266 | S234 |
| D276 | D244 |

Furthermore, percent identity may also be assessed with these conventional bioinformatic methods.

In one aspect, the present invention pertains to beta-lactamases and/or pharmaceutical compositions comprising an amino acid sequence having at least 70% (e.g. about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 3 and one or more of the following mutations of Ambler classification: F33X, Q135X, G156X, A232X, A237X, A238X, S240X, T243X, R244X, S266X, and D276X, wherein X is any naturally-occurring amino acid and with the proviso that D276X is not present in the context of a single mutant. In some embodiments, X is a naturally occurring hydrophilic or hydrophobic amino acid residue or a non-classical amino acid.

In another aspect, the present invention pertains to beta-lactamases and/or pharmaceutical compositions comprising an amino acid sequence having at least 70% sequence identity with SEQ ID NO: 1 or SEQ ID NO: 3 and one or more of the following mutations of Ambler classification: a hydrophobic residue other than phenylalanine (F) at position 33; a hydrophobic residue other than glutamine (Q) at position 135; a hydrophilic residue other than glycine (G) at position 156; a hydrophobic residue other than alanine (A) at position 232; a hydrophilic residue other than alanine (A) at position 237; a hydrophobic or hydrophilic residue other than alanine (A) at position 238; a hydrophilic residue other than serine (S) at position 240; a hydrophobic residue other than threonine (T) at position 243; a hydrophobic residue other than arginine (R) at position 244; a hydrophilic residue other than serine (S) at position 266; and a hydrophilic residue other than aspartate (D) at position 276, with the proviso that hydrophilic amino acid residue other than aspartic acid (D) at a position corresponding to position 276 is not present in the context of a single mutant.

As used throughout, a hydrophilic amino acid residue may include a polar and positively charged hydrophilic residue selected from arginine (R) and lysine (K), a polar and neutral of charge hydrophilic residue selected from asparagine (N), glutamine (Q), serine (S), threonine (T), proline (P), and cysteine (C), a polar and negatively charged hydrophilic residue selected from aspartate (D) and glutamate (E), or an aromatic, polar and positively charged hydrophilic including histidine (H). As used throughout, a hydrophobic amino acid residue may include a hydrophobic, aliphatic amino acid selected from glycine (G), alanine (A), leucine (L), isoleucine (I), methionine (M), or valine (V) or a hydrophobic, aromatic amino acid selected from phenylalanine (F), tryptophan (W), or tyrosine (Y). Mutations may be made to the gene sequence of a beta-lactamase (e.g. SEQ ID NOs: 3 and 4) by reference to the genetic code, including taking into account codon degeneracy.

In some embodiments, the beta-lactamases and/or pharmaceutical compositions comprise one or more of the following mutations at positions of Ambler classification: F33Y, Q135M, G156R, A232G, A237S, A238G or T, S240P or D, T243I, R244T, S266N, D276N or R or K, provided that D276N or R or K is not in the context of a single mutant. In one embodiment, the beta-lactamases and/or pharmaceutical compositions comprise Q135M. In another embodiment, the beta-lactamases and/or pharmaceutical compositions comprise G156R and A238T. In another embodiment, the beta-lactamases and/or pharmaceutical compositions comprise F33Y and D276N. In still another embodiment, the beta-lactamases and/or pharmaceutical compositions comprise F33Y, S240P, and D276N. In one embodiment, the beta-lactamases and/or pharmaceutical compositions comprise F33Y, A238T, and D276N. In another embodiment, the beta-lactamases and/or pharmaceutical compositions comprise A232G, A237S, A238G, and S240D. In a further embodiment, the beta-lactamases and/or pharmaceutical compositions comprise A232G, A237S, A238G, S240D, and R244T. In another embodiment, the beta-lactamases and/or pharmaceutical compositions comprise A232G, A237S, A238G, S240D, and D276R. In one embodiment, the beta-lactamases and/or pharmaceutical compositions comprise A232G, A237S, A238G, S240D, and D276K. In one embodiment, the beta-lactamases and/or pharmaceutical compositions comprise A232G, A237S, A238G, S240D, and Q135M. In one embodiment, the beta-lactamases and/or pharmaceutical compositions comprise A238T. In one embodiment, the beta-lactamases and/or pharmaceutical compositions comprise T2431, S266N, and D276N. In one embodiment, the beta-lactamases and/or pharmaceutical compositions comprise A232G, A237S, A238G, S240D, and D276N.

In other embodiments, the beta-lactamases and/or pharmaceutical compositions comprise an amino acid sequence having at least 70% sequence identity with SEQ ID NO: 2 and the following of Ambler classification: a hydrophobic residue other than alanine (A) at position 232; a hydrophilic residue other than alanine (A) at position 237; a hydrophobic residue other than alanine (A) at position 238; a hydrophilic residue other than serine (S) at position 240; and a hydrophilic residue other than aspartate (D) at position 276. In some embodiments, the hydrophobic residue other than alanine (A) at position 232 is glycine (G). In some embodiments, the hydrophilic residue other than alanine (A) at position 237 is serine (S). In some embodiments, the hydrophobic residue other than alanine (A) at position 238 is glycine (G). In some embodiments, the hydrophilic residue other than serine (S) at position 240 is aspartate (D). In some embodiments, the other than aspartate (D) at position 276 is asparagine (N). In some embodiments, the beta-lactamase and/or pharmaceutical composition comprises one or more of A232G, A237S, A238G, S240D, and D276N. In some embodiments, the beta-lactamase and/or pharmaceutical composition comprises all of A232G, A237S, A238G, S240D, and D276N, the sequence of which may be SEQ ID NO:5:

SEQ ID NO: 5
EMKDDFAKLEEQFDAKLGIFALDTGTNRTVAYRPDERFAFASTIKALTVGV

LLQQKSIEDLNQRITTRDDLVNYNPITEKHVDTGMTLKELADASLRYSDNA

AQNLILKQIGGPESLKKELRKIGDEVTNPERFEPELNEVNPGETQDTSTAR

ALVTSLRAFALEDKLPSEKRELLIDWMKRNTTGDALIRAGVPDGWEVGDKT

GSGDYGTRNDIAIIWPPKGDPVVLAVLSSRDKKDAKYDNKLIAEATKVVMK

ALNMNGK
or

SEQ ID NO: 6: SEQ ID NO: 5, including the signal and the addition of the QASKT amino acids (the coding region is underlined):

-continued
MIQKRKRTVSFRLVLMCTLLFVSLPI

TKTSAQASKT<u>EMKDDFAKLEEQFDAK</u>

<u>LGIFALDTGTNRTVAYRPDERFAFAS</u>

<u>TIKALTVGVLLQQKSIEDLNQRITYT</u>

<u>RDDLVNYNPITEKHVDTGMTLKELAD</u>

<u>ASLRYSDNAAQNLILKQIGGPESLKK</u>

<u>ELRKIGDEVTNPERFEPELNEVNPGE</u>

<u>TQDTSTARALVTSLRAFALEDKLPSE</u>

<u>KRELLIDWMKRNTTGDALIRAGVPDG</u>

<u>WEVGDKTGSGDYGTRNDIAIIWPPKG</u>

<u>DPVVLAVLSSRDKKDAKYDNKLIAEA</u>

<u>TKVVMKALNMNGK</u>

The invention also provides for polynucleotides encoding any of the beta-lactamases of the invention, including, for example, vectors, comprising such polynucleotides. Such polynucleotides may further comprise, in addition to sequences encoding the beta-lactamases of the invention, one or more expression control elements. For example, the polynucleotide, may comprise one or more promoters or transcriptional enhancers, ribosomal binding sites, transcription termination signals, and polyadenylation signals, as expression control elements. The polynucleotide may be inserted within any suitable vector, which may be contained within any suitable host cell for expression. An illustrative polynucleotide of the invention is SEQ ID NO: 7:

SEQ ID NO: 7

Full nucleotide sequence of A232G, A237S, A238G, S240D, and D276N mutant, Hind III site (AAGCTT-in bold) and additional K and T amino acids. The leader and additional nucleotides (Hind III site and K and T amino acids-for the addition of the amino acid sequence QASKT) are underlined.

<u>atgattcaaaaacgaaagcggacagtttcgttcagacttgtgcttatgtgc</u>

<u>acgctgttatttgtcagtttgccgattacaaaaacatcagcgc</u>aagcttcc aagacggagatgaaagatgattttgcaaaacttgaggaacaatttgatgca aaactcgggatctttgcattggatacaggtacaaaccggacggtagcgtat cggccggatgagcgttttgcttttgcttcgacgattaaggctttaactgta ggcgtgcttttgcaacagaaatcaatagaagatctgaaccagagaataaca tatacacgtgatgatcttgtaaactacaacccgattacggaaaagcacgtt gatacgggaatgacgctcaaagagcttgcggatgcttcgcttcgatatagt gacaatgcggcacagaatctcattcttaaacaaattggcggacctgaaagt ttgaaaaaggaactgaggaagattggtgatgaggttacaaatcccgaacga ttcgaaccagagttaaatgaagtgaatccgggtgaaactcaggataccagt acagcaagagcacttgtcacaagccttcgagcctttgctcttgaagataaa cttccaagtgaaaaacgcgagcttttaatcgattggatgaaacgaaatacc actggagacgccttaatccgtgccggtgtgccggacggttgggaagtgggt

```
-continued
gataaaactggaagcggagattatggaacccggaatgacattgccatcatt tggccgccaaaaggagatcctgtcgttcttgcagtattatccagcagggat aaaaaggacgccaagtatgataataaacttattgcagaggcaacaaaggtg gtaatgaaagccttaaacatgaacggcaaataa
```

In some embodiments, the vector can remain episomal or become chromosomally integrated, as long as the insert encoding the therapeutic agent can be transcribed. Vectors can be constructed by standard recombinant DNA technology. Vectors can be, for example, plasmids, phages, cosmids, phagemids, viruses, or any other types known in the art, which are used for replication and expression in prokaryotic or eukaryotic cells (e.g. an adenovirus; a retrovirus; a lentivirus; an scAAV; pGEX vector; pET vector; and pHT vector). It will be appreciated by one of skill in the art that a wide variety of components known in the art (such as expression control elements) may be included in such vectors, including a wide variety of transcription signals, such as promoters and other sequences that regulate the binding of RNA polymerase onto the promoter. Any promoter known to be effective in the cells in which the vector will be expressed can be used to initiate expression of the therapeutic agent. Suitable promoters may be inducible or constitutive. Examples of suitable promoters include the pET system (INVITROGEN), lac promoter, tac, trc, T7, T7A3 promoter, PhoA, plux, and Phage lambda pR, lambda pL promoter (see, e.g. *J Ind Microbiol Biotechnol* (2012) 39:383-399; *Curr Opin Biotech* 2001, 12: 195, the contents of which are hereby incorporated by reference). The promoter may be inducible (e.g. via IPTG, metabolites, temperature). Examples of suitable promoters include the SV40 early promoter region, the promoter contained in the 3' long terminal repeat of Rous sarcoma virus, the HSV-1 thymidine kinase promoter, the regulatory sequences of the metallothionein gene, etc., as well as the following animal transcriptional control regions, which exhibit tissue specificity and have been utilized in transgenic animals: elastase I gene control region which is active in pancreatic acinar cells; insulin gene control region which is active in pancreatic beta cells, immunoglobulin gene control region which is active in lymphoid cells, mouse mammary tumor virus control region which is active in testicular, breast, lymphoid and mast cells, albumin gene control region which is active in liver, alpha-fetoprotein gene control region which is active in liver, alpha 1-antitrypsin gene control region which is active in the liver, beta-globin gene control region which is active in erythroid cells, myelin basic protein gene control region which is active in oligodendrocyte cells in the brain, myosin light chain-2 gene control region which is active in skeletal muscle, and gonadotropin releasing hormone gene control region which is active in the hypothalamus.

The invention provides polynucleotides, such polynucleotides comprising a nucleotide sequence encoding a beta-lactamase of the invention. For example, the nucleotide sequence that encodes a beta-lactamase of the invention. Such polynucleotides may further comprise additional control element(s) operably linked to the nucleotide sequence, such as promoter elements and/or other transcription or expression-related signals. The polynucleotide may be inserted into various vectors, which may be useful for production of the therapeutic agent in host cells, including, for example, bacterial and eukaryotic host cells. The beta-lactamase of the invention can be prepared by known recombinant expression techniques. For example, to recombinantly produce the beta-lactamase of the invention, a nucleic acid sequence encoding the respective gene is operatively linked to a suitable promoter sequence such that the nucleic acid sequence encoding such beta-lactamase of the invention will be transcribed and/or translated in the host cells. Illustrative promoters are those useful for expression in various systems such as the T7 promoter, Pspac, PgroES, Pgsi and Plux and amyQ promoter and/or amyQ signal peptide from *Bacillus amyloliquefaciens* (by way of non-limiting example Gen Bank ID No. J01542.1, the contents of which are hereby incorporated by reference). Any commonly used expression system may be used, including eukaryotic or prokaryotic systems. Specific examples include yeast (e.g., *Saccharomyces* spp., *Pichia* spp.), baculovirus, mammalian, and bacterial systems, such as *E. coli*, *B. subtillis*, and *Caulobacter*.

Host cells of the present invention include, for example, prokaryotic, eukaryotic, bacterial, yeast, algal, plant, insect, and/or mammalian cells. In some embodiments, the invention encompasses any type of cell that recombinantly expresses genes associated with the invention, including prokaryotic and eukaryotic cells. In some embodiments the cell is a bacterial cell, such as, for example, *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as, for example, a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. The yeast strain may be a *S. cerevisiae* strain or a *Yarrowia* spp. strain. Other examples of fungi include, for example, *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell or a plant cell (e.g., *A. thaliana, C. reinhardtii, Arthrospira, P. tricomutum, T. suecica, P. carterae, P. tricomutum, Chlorella* spp., such as *Chlorella vulgaris*). Target cells can include transgenic and recombinant cell lines. In addition, heterologous cell lines can be used, such as Chinese Hamster Ovary cells (CHO). Host cells may be unicellular host cells or multicellular host cells.

In various embodiments, the beta-lactamases of the invention possess functional characteristics that make them desirable for a variety of uses, including therapeutic uses. Methods of characterizing beta-lactamases are known in the art (e.g. nitrocefin assay as described by O'Callaghan, et al. *Antimicrob. Agents Chemother,* 1:283-288; the various methods of Viswanatha et al. *Methods Mol Med.* 2008; 142:239-60).

In one embodiment, the inventive beta-lactamases hydrolyze one or more of penicillins and cephalosporins. As used throughout, penicillins include, for example, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillin G (e.g. PENTIDS or PFIZERPEN); Penicillin V (e.g. VEETIDS (PEN-VEE-K)); Piperacillin (e.g. PIPRACIL); Temocillin (e.g. NEGABAN); and Ticarcillin (e.g. TICAR). As used throughout, cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). In a specific embodiment, cephalosporins include, for example, cefoperazone, ceftriaxone or cefazolin. In a specific embodiment, the inventive beta-lactamases have improved catalytic efficiency against cephalosporins as compared to SEQ ID NO: 1.

In various embodiments, the inventive beta-lactamases possess desirable enzyme kinetic characteristics. For example, in some embodiments, the beta-lactamases possess a low $K_M$ for at least one cephalosporin, including, for example, a $K_M$ of less than about 500 µM, or about 100 µM, or about 10 µM, or about 1 µM, or about 0.1 µM (100 nM), or about 0.01 µM (10 nM), or about 1 nM. For example, in some embodiments, the beta-lactamases possess a low $K_M$ for at least one penicillin, including, for example, a $K_M$ of less than about 500 µM, or about 100 µM, or about 10 µM, or about 1 µM, or about 0.1 µM (100 nM), or about 0.01 µM (10 nM), or about 1 nM. In various embodiments, the inventive beta-lactamases possess a high $V_{max}$ for at least one cephalosporin, including, for example, $V_{max}$ which is greater than about 100 s-1, or about 1000 s-1, or about 10000 s-1, or about 100000 s-1, or about 1000000 s-1. In various embodiments, the inventive beta-lactamases possess a high $V_{max}$ for at least one penicillin, including, for example, $V_{max}$ which is greater than about 100 s-1, or about 1000 s-1, or about 10000 s-1, or about 100000 s-1, or about 1000000 s-1. In various embodiments, the inventive beta-lactamases possess catalytic efficiency is greater than about $10^6$ $M^{-1}$ $s^{-1}$ for at least one cephalosporin. In various embodiments, the inventive beta-lactamases possess catalytic efficiency is greater than about $10^6$ $M^{-1}$ $s^{-1}$ for at least one penicillin. In various embodiments, the inventive beta-lactamases possess the desirable enzyme kinetic characteristics for at least one of either or both of cephalosporins and penicillins.

In various embodiments, the inventive beta-lactamases are stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the beta-lactamase is stable in the large intestine, optionally selected from one or more of colon transversum, colon descendens, colon ascendens, colon sigmoidenum and cecum. In a specific embodiment, the beta-lactamase is stable in the small intestine, optionally selected from one or more of duodenum, jejunum, and ileum. In some embodiments, the beta-lactamase is resistant to proteases in the GI tract, including for example, the small intestine. In some embodiments, the beta-lactamase is substantially active at a pH of about 6.0 to about 7.5, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5 (including, for example, via formulation, as described herein). In various embodiments, the beta-lactamases of the present invention are resistant to one or more beta-lactamase inhibitors, optionally selected from avibactam, tazobactam, sulbactam, and clavulanic acid. In some embodiments, stable refers to an enzyme that has a long enough half life and maintains enough activity for therapeutic effectiveness.

In various embodiments, the present invention pertains to pharmaceutical compositions comprising a beta-lactamase described herein and one or more of and a pharmaceutically acceptable carrier or excipient as described herein. In a specific embodiment, the pharmaceutical composition is formulated for oral administration, e.g. as a tablet or multiparticulate sprinkle or a multi-particulate capsule. However, as described herein, other administration routes and formulations are also provided.

In some embodiments, the pharmaceutical compositions may be used in conjunction with or be co-formulations with an additional agent. In some embodiments, the additional agent is an additional antibiotic degradation enzyme, such as, for example, a beta-lactamase of class EC 3.5.2.6. In some embodiments, the antibiotic degradation enzyme is selected from a functional Group 1, Group 2, Group 3, or a Group 4 beta-lactamase (see, e.g., Bush et al., *Antimicrob. Agents Chemother*, 39: 1211, the contents of which are hereby incorporated by reference): without wishing to be bound by theory, Group 1 consists of cephalosporinases that are not well inhibited by clavulanic acid; Group 2 consists of penicillinases, cephalosporinases and broad-spectrum beta-lactamases that are generally inhibited by active site-directed beta-lactamase inhibitors; Group 3 consists of met-allo-beta-lactamases that hydrolyze penicillins, cephalosporins and carbapenems, and that are poorly inhibited by almost all beta-lactam-containing molecules; and Group 4 consists of penicillinases that are not well inhibited by clavulanic acid) and/or a molecular/Ambler class A, or class B, or class C, or class D beta-lactamase (see, e.g., Ambler 1980, *Philos Trans R Soc Lond B Biol Sci*. 289: 321 the contents of which are hereby incorporated by reference), without wishing to be bound by theory: Classes A, C, and D gather evolutionarily distinct groups of serine beta-lactamase enzymes, and class B the zinc-dependent ("EDTA-inhibited") beta-lactamase enzymes (see Ambler R. P. et al., 1991, *Biochem J*. 276: 269-270, the contents of which are hereby incorporated by reference). In some embodiments, the antibiotic degradation enzyme is a serine beta-lactamase or a zinc-dependent (EDTA-inhibited) beta-lactamase. For example, in some embodiments, the beta-lactamase is one or more of P1A, P2A, or P3A. Further, the beta-lactamase may be an extended-spectrum beta-lactamase (ESBL), optionally selected from a TEM, SHV, CTX-M, OXA, PER, VEB, GES, and IBC beta-lactamase. Further, the beta-lactamase may be an inhibitor-resistant β-lactamase, optionally selected from an AmpC-type β-lactamases, Carbapenemase, IMP-type carbapenemases (metallo-β-lactamases), VIM (Verona integron-encoded metallo-β-lactamase), OXA (oxacillinase) group of β-lactamases, KPC (*K. pneumonia* carbapenemase), CMY (Class C), SME, IMI, NMC and CcrA, and a NDM (New Delhi metallo-β-lactamase, e.g. NDM-1) beta-lactamase.

In some embodiments, the additional agent is an adjunctive therapy that is used in, for example, the treatment of CDI as described herein. In some embodiments, the additional agent is metronidazole (e.g. FLAGYL), fidaxomicin (e.g. DIFICID), or vancomycin (e.g. Vancocin), rifaximin, fecal bacteriotherapy, charcoal-based binders (e.g. DAV132), probiotic therapy (see, e.g., *Intnat'l J Inf Dis*, 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin. In some embodiments, any of the penicillins and cephalosporins described herein may be the additional agent.

For all additional agent compositions and methods, targeting to various parts of the GI tract may be employed as described herein.

In some embodiments, the inventive beta-lactamases and/or pharmaceutical compositions (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids.

In still other embodiments, the inventive beta-lactamases and/or pharmaceutical compositions described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The inventive beta-lactamases and/or pharmaceutical compositions (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the compositions of the present invention having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any inventive beta-lactamases and/or pharmaceutical compositions (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

The present invention includes the described inventive beta-lactamases and/or pharmaceutical compositions (and/or additional agents) in various formulations. Any inventive beta-lactamase and/or pharmaceutical composition (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the inventive beta-lactamases and/or pharmaceutical compositions (and/or additional agents) can also include a solubilizing agent. Also, the agents can be delivered with a suitable vehicle or delivery device as known in the art. Compositions for administration can optionally include a local anesthetic such as, for example, lignocaine to lessen pain at the site of the injection. Combination therapies outlined herein can be co-delivered in a single delivery vehicle or delivery device.

The formulations comprising the inventive beta-lactamases and/or pharmaceutical compositions (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any inventive beta-lactamases and/or pharmaceutical compositions (and/or additional agents) described herein is formulated in accordance with routine procedures as a composition adapted for a mode of administration described herein.

In some embodiments, the administration of any inventive beta-lactamases and/or pharmaceutical compositions (and/or additional agents) is any one of oral, intravenous, and parenteral. In some embodiments, the administration of any inventive beta-lactamases and/or pharmaceutical compositions (and/or additional agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, particularly to the ears, nose, eyes, or skin. In some embodiments, the administering is effected orally or by parenteral injection. The mode of administration can be left to the discretion of the practitioner, and depends in-part upon the site of the medical condition. In most instances, administration results in the release of any agent described herein into the bloodstream.

Any inventive beta-lactamases and/or pharmaceutical compositions (and/or additional agents) described herein can be administered orally. Such inventive beta-lactamases and/or pharmaceutical compositions (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with an additional agent. Administration can be systemic or local. In some embodiments, administration is not at the site of infection to avoid, for example, hydrolysis of an antibiotic at the site of infection. Various delivery systems are known, e.g., encapsulation in liposomes, microparticles, microcapsules, capsules, etc., and can be used to administer.

In specific embodiments, it may be desirable to administer locally to the area in need of treatment.

In one embodiment, any inventive beta-lactamases and/or pharmaceutical compositions (and/or additional agents) described herein is formulated in accordance with routine procedures as a composition adapted for oral administration to humans. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any inventive beta-lactamases and/or pharmaceutical compositions (and/or additional agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

Inventive beta-lactamases and/or pharmaceutical compositions (and/or additional agents) may be administered to a subject, by, for example, directly or indirectly contacting the mucosal tissues of the gastrointestinal tract. The gastrointestinal tract a includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). Various methods may be used to formulate and/or deliver the agents descried herein to a location of interest. For example, the inventive beta-lactamases and/or pharmaceutical compositions (and/or additional agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract.

In some embodiments, the compositions of the invention are formulated for enteric delivery. For example, the compositions may be formulated as capsules or tablets for oral delivery, and may comprise a delayed-release coating containing one or more enteric agents. A delayed-release coating is substantially stable in gastric fluid and substantially unstable (e.g., dissolves rapidly or is physically unstable) in intestinal fluid, thus providing for substantial release of the active agent from the composition in the affected region of the small intestine, e.g., the duodenum, the jejunum, and/or the ileum or large intestine, e.g. the colon transversum, colon descendens, colon ascendens, colon sigmoidenum and cecum.

The inventive beta-lactamases and/or pharmaceutical compositions (and/or additional agents) are generally stable in gastric fluid or simulated intestinal fluid, that is, the compositions are stable in acidic environments. Thus, the compositions release less than 30% by weight of the active agent in gastric fluid with a pH of 5 or less, or simulated gastric fluid with a pH of 5 or less, in approximately 120 minutes. Compositions of the invention may release from about 0% to about 25%, or from about 0% to about 10% by weight of the active agent in gastric fluid with a pH of 5 or less, or simulated gastric fluid with a pH of 5 or less, in approximately 120 minutes. Compositions of the invention in certain embodiments release no more than about 1%, about 2%, about 3%, about 4%, about 5%, about 6%, about 7%, about 8%, about 9%, or about 10% by weight of the active agent in gastric fluid, or simulated gastric fluid with a pH of 5 or less, in approximately 120 minutes. The pharmaceutical compositions generally release active agent to act locally at regions of the small or large intestine. In certain embodiments, the composition of the invention release about 70% or more by weight of the active agent in the small or large intestine within about 120 minutes. In certain embodiments, the composition releases 80% or more, or 90% or more, of the active agent in small or large intestine, within about ninety minutes or within about 120 minutes. In certain embodiments this release in the small or large intestine is mediated by pH of gastric fluid or simulated gastric fluid—for example, a release when the pH of about 5 or greater (e.g. pH of about 5.5-6.5 for release in the duodenum, pH of about 6-7 for release in the colon ascendens or jejunum, pH of about 6.5-7 for release in the ileum, pH of about 7-7.5 for release in the colon descendens).

The pharmaceutical composition may control intestinal release of the active agent through one or more delayed-release coating(s), which remain essentially intact, and/or which may be essentially insoluble, in gastric fluid. The stability of the delayed-release coating can be pH dependent. Delayed-release coatings that are pH dependent will be substantially stable in acidic environments (pH 5 or less), and substantially unstable in near neutral to alkaline environments (pH greater than 5). For example, the delayed-release coating may essentially disintegrate or dissolve in near neutral to alkaline environments, such as are found in the small intestine or large intestine, to thereby release active agent locally to diseased or affected tissue.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Alternatively, the stability of the delayed-release coating may be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans.

In some embodiments, the target organ for the release of the active agent from the compositions of the invention, which include gastric resistant capsules or tablets, is the small intestine, such as the duodenum and the jejunum or the large intestine, e.g. the colon transversum, colon descendens, colon ascendens, colon sigmoidenum and cecum. See Remington's Pharmaceutical Sciences, 16th Ed., Eds. Osol, Mack Publishing Co., Chapter 89 (1980); Digenis et al., *J. Pharm. Sci.*, 83:915-921 (1994); Vantini et al., *Clinica Terapeutica*, 145:445-451 (1993); Yoshitomi et al., *Chem. Pharm. Bull.*, 40:1902-1905 (1992); Thoma et al., *Pharmazie*, 46:331-336 (1991); Morishita et al., *Drug Design and Delivery*, 7:309-319 (1991); and Lin et al., *Pharmaceutical Res.*, 8:919-924 (1991) for examples of the preparation of such tablets or capsules (the contents of the above are hereby incorporated by reference in their entireties).

In some embodiments, the compositions of the present invention may be formulated using the EUDRAGIT system, as known in the art and described in *Pharma Polymer* No. 7, October 2000, the contents of which are hereby incorporated by reference in their entirety.

The dosage of any inventive beta-lactamases and/or pharmaceutical compositions (and/or additional agents) described herein as well as the dosing schedule can depend on various parameters, including, but not limited to, the disease being treated, the subject's general health, and the administering physician's discretion. Any agent described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional therapeutic agent, to a subject in need thereof. In various embodiments any agent described herein is administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart.

The amount of any inventive beta-lactamases and/or pharmaceutical compositions (and/or additional agents) described herein that is admixed with the carrier materials to produce a single dosage can vary depending upon the subject being treated and the particular mode of administration. In vitro or in vivo assays can be employed to help identify optimal dosage ranges.

In general, the doses that are useful are known to those in the art. For example, doses may be determined with reference *Physicians' Desk Reference*, 66th Edition, PDR Network; 2012 Edition (Dec. 27, 2011), the contents of which are incorporated by reference in its entirety. In some embodiment, the present invention allows a patient to receive doses that exceed those determined with reference Physicians' Desk Reference.

The dosage of any inventive beta-lactamases and/or pharmaceutical compositions (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

In specific embodiments, the concentration of any inventive beta-lactamases and/or pharmaceutical compositions (and/or additional agents) is about 0.2 to about 20 g/L when administered orally or about 4 g/mL when administered intravenously.

In some embodiments, when orally administered to a mammal, the dosage of any inventive beta-lactamases and/or pharmaceutical compositions (and/or additional agents) described herein may be about 0.001 mg/kg/day to about 100 mg/kg/day, about 0.01 mg/kg/day to about 50 mg/kg/day, or about 0.1 mg/kg/day to about 10 mg/kg/day. When orally administered to a human, the dosage of any agent described herein is normally about 0.001 mg to 1000 mg per day, about 1 mg to about 600 mg per day, or about 5 mg to about 30 mg per day. In one embodiment, 100 mg per day of the inventive beta-lactamases and/or pharmaceutical compositions is administered orally to a human. For administration of any inventive beta-lactamases and/or pharmaceutical compositions (and/or additional agents) described herein by parenteral injection, the dosage is normally about 0.1 mg to about 250 mg per day, about 1 mg to about 20 mg per day, or about 3 mg to about 5 mg per day. Injections may be given up to four times daily. Generally, when orally or parenterally administered, the dosage of any agent described herein is normally about 0.1 mg to about 1500 mg per day, or about 0.5 mg to about 10 mg per day, or about 0.5 mg to about 5 mg per day. A dosage of up to about 3000 mg per day can be administered. In some embodiments, the dose may be about 1000 mg per day. In some embodiments, the following dose regiment can be used: 100 mg, four times a day.

In various embodiments, the dosage of any inventive beta-lactamases and/or pharmaceutical compositions (and/or additional agents) described herein is administered to achieve an intestinal concentration of from about 1 ng/ml to about 10,000 ng/ml, about 1 ng/ml to about 5,000 ng/ml, about 1 ng/ml to about 2,500 ng/ml, about 1 ng/ml to about 1,000 ng/ml, about 1 ng/ml to about 500 ng/ml, about 1 ng/ml to about 250 ng/ml, about 1 ng/ml to about 100 ng/ml, about 1 ng/ml to about 50 ng/ml, about 1 ng/ml to about 25 ng/ml, about 1 ng/ml to about 10 ng/ml, about 10 ng/ml to about 10,000 ng/ml, about 10 ng/ml to about 5,000 ng/ml, about 10 ng/ml to about 2,500 ng/ml, about 10 ng/ml to about 1,000 ng/ml, about 10 ng/ml to about 500 ng/ml, about 10 ng/ml to about 250 ng/ml, about 10 ng/ml to about 100 ng/ml, about 10 ng/ml to about 50 ng/ml, about 10 ng/ml to about 25 ng/ml, about 100 ng/ml to about 10,000 ng/ml, about 100 ng/ml to about 5,000 ng/ml, about 100 ng/ml to about 2,500 ng/ml, about 100 ng/ml to about 1,000 ng/ml, about 100 ng/ml to about 500 ng/ml, or about 100 ng/ml to about 250 ng/ml. In various embodiments, the intestinal concentration of any inventive beta-lactamases and/or pharmaceutical compositions (and/or additional agents) described herein is 10 ng/ml, 100 ng/ml, or 1,000 ng/ml.

In another embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989).

Any inventive beta-lactamases and/or pharmaceutical compositions (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropyl cellulose, hydropropylmethyl cellulose, polyvinylpyrrolidone, other polymer matrices, gels, permeable membranes, osmotic systems, multilayer coatings, microparticles, liposomes, microspheres, or a combination thereof to provide the desired release profile in varying proportions. Suitable controlled- or sustained-release formulations known to those skilled in the art, including those described herein, can be readily selected for use with the active ingredients of the agents described herein. The invention thus provides single unit dosage forms suitable for oral administration such as, but not limited to, tablets, capsules, gelcaps, and caplets that are adapted for controlled- or sustained-release.

Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any inventive beta-lactamases and/or pharmaceutical compositions (and/or additional agents) described herein can, independently, be one to six times daily (e.g. 1, or 2, or 3, or 4, or 5, or 6 times per day) or one to four times per month or one to six times per year or once every two, three, four or five years. Administration can be for the duration of one day or one month, two months, three months, six months, one year, two years, three years, and may even be for the life of the subject. Chronic, long-term administration will be indicated in many cases. The dosage may be administered as a single dose or divided into multiple doses. In general, the desired dosage should be administered at set intervals for a prolonged period, usually at least over several weeks or months, although longer periods of administration of several months or years or more may be needed.

The dosage regimen utilizing any inventive beta-lactamases and/or pharmaceutical compositions (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any inventive beta-lactamases and/or pharmaceutical compositions (and/or additional agents) described herein can be administered in a single daily dose, or the total daily dosage can be administered in divided doses of two, three or four times daily. Furthermore, any inventive beta-lactamases and/or pharmaceutical compositions (and/or additional agents) described herein can be administered continuously rather than intermittently throughout the dosage regimen.

In various aspects, the present invention provides methods for treating or preventing an antibiotic-induced adverse effect in the GI tract, comprising administering an effective amount of a beta-lactamase and/or pharmaceutical composition (and/or additional agent) described herein to a patient in need thereof. In one aspect, the present invention provides methods for preventing an antibiotic-induced adverse effect in the GI tract, comprising administering an effective amount of a beta-lactamase and/or pharmaceutical composition (and/or additional agent) described herein to a patient in need thereof (by way of non-limiting example, a patient that is being administered or will be administered an antibiotic, including those described herein). In various aspects, the present invention provides methods for treating or preventing *C. difficile* infection (CDI) and/or a *C. difficile*-associated disease, comprising administering an effective amount of a beta-lactamase and/or pharmaceutical composition (and/or additional agent) described herein to a patient in need thereof. In one aspect, the present invention provides methods for preventing *C. difficile* infection (CDI) and/or a *C. difficile*-associated disease, comprising administering an effective amount of a beta-lactamase and/or pharmaceutical composition (and/or additional agent) described herein to a patient in need thereof (by way of non-limiting example, a patient that is being administered or will be administered an antibiotic, including those described herein.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various aspects, the present invention provides methods for protecting a subject's gastrointestinal microbiome, comprising administering an effective amount of a beta-lactamase and/or pharmaceutical composition (and/or additional agent) described herein. In various embodiments, the subject is undergoing treatment or has recently undergone treatment with an antibiotic. In various embodiments, the beta-lactamase and/or pharmaceutical composition (and/or additional agent) described herein is capable of degrading or inactivating the antibiotic.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a women and/or is elderly (e.g. over about 65 years old) and/or is an elderly woman and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference. For example, the microbiome-mediated disorder may be selected from an antibiotic-induced adverse effect, a *C. difficile* infection (CDI), a *C. difficile*-associated disease, ulcerative colitis, Crohn's disease, and irritable bowel syndrome. In various embodiments, the microbiome-mediated disorder is an antibiotic-induced adverse effect, a *C. difficile* infection (CDI), or a *C. difficile*-associated disease. In an embodiment, the present invention provides methods for treating an antibiotic-induced adverse effect in the GI tract, comprising administering an effective amount of a beta-lactamase and/ or pharmaceutical composition (and/or additional agent) described herein to a subject who is undergoing treatment or has recently undergone treatment with an antibiotic. In another embodiment, the present invention provides methods for preventing an antibiotic-induced adverse effect in the GI tract, comprising administering an effective amount of a beta-lactamase and/or pharmaceutical composition (and/or additional agent) described herein to a subject who is undergoing treatment or has recently undergone treatment with an antibiotic.

In various embodiments, the present uses and methods pertain to co-treatment (simultaneously or sequentially) with the beta-lactamases and/or pharmaceutical compositions of the present invention and any additional agent described herein and/or any initial and/or adjunctive therapy, or treatment with a co-formulation of the beta-lactamases and/or pharmaceutical compositions of the present invention and any additional agent described herein and/or any initial and/or adjunctive therapy for treatment of the various diseases described herein, or methods of treating the various diseases described herein in a patient undergoing treatment with any additional agent described herein and/or any initial and/or adjunctive therapy described herein by administering a beta-lactamases and/or pharmaceutical compositions of the present invention to the patient.

In various embodiments, the CDI and/or C. difficile associated disease is treated or prevented in the context of initial onset or relapse/recurrence (e.g. due to continued or restarted antibiotic therapy). For example, in a patient that has previously suffered from CDI, the present beta-lactamases and/or pharmaceutical compositions (and/or additional agents) may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or C. difficile associated disease may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, CDI and/or C. difficile associated disease may also be diagnosed via enzyme immunoassays e.g. to detect the C. difficile toxin A or B antigen and/or glutamine dehydrogenase (GDH), which is produced by C. difficile organisms), polymerase chain reaction (e.g. to detect the C. difficile toxin A or B gene or a portion thereof (e.g. tcdA or tcdB), including the ILLUMIGENE LAMP assay), a cell cytotoxicity assay. For example, any one of the following tests may be used may be used: Meridian ImmunoCard Toxins A/B; Wampole Toxin A/B Quik Chek; Wampole C. diff Quik Chek Complete; Remel Xpect Clostridium difficile Toxin A/B; Meridian Premier Toxins A/B; Wampole C. difficile Tox A/B II; Remel Prospect Toxin A/B EIA; Biomerieux Vidas C. difficile Toxin A&B; BD Geneohm C. diff; Prodesse Progastro CD; and Cepheld Xpert C. diff. In various embodiments, the clinical sample is a patient stool sample.

Also a flexible sigmoidoscopy "scope" test and/or an abdominal X-ray and/or a computerized tomography (CT) scan, which provides images of your colon, may be used in assessing a patient (e.g. looking for characteristic creamy white or yellow plaques adherent to the wall of the colon). Further, biopsies (e.g. of any region of the GI tract) may be used to assess a potential CDI and/or C. difficile associated disease patient.

Furthermore, the patients of the invention include, but are not limited to, patients that are at a particular risk for CDI and/or C. difficile associated disease, such as those which have been taking an antibiotic during the past 30 or so days and/or have an immune system that is weak (e.g. from a chronic illness) and/or are women and/or are elderly (e.g. over about 65 years old) and/or are elderly woman and/or undergo treatment with for heartburn or stomach acid disorders (e.g. with agents such as PREVACID, TAGAMET, PRILOSEC, or NEXIUM and related drugs) and/or have recently been in the hospital, including in an intensive care unit, or live in a nursing home. Accordingly, in some embodiments, the methods and uses of the present invention treat or prevent a nosocomial infection and/or a secondary emergent infection and/or a hospital acquired infection (HAI).

In some embodiments, the methods of the invention treat or prevent a ceftriaxone-associated adverse effect (e.g. diarrhea, nausea, vomiting, dysgeusia, and pseudomembranous colitis disease and/or symptoms).

In some embodiments, the methods and uses of the present invention relate to a patient is undergoing treatment or has recently undergone treatment with one or more primary antibiotic. A "primary antibiotic" refers to an antibiotic that is administered to a patient and which may result in CDI and/or C. difficile associated disease. These include the antibiotics that most often lead to CDI and/or C. difficile associated disease: fluoroquinolones, cephalosporins, clindamycin and penicillins.

In some embodiments, the methods and uses of the present invention relate to the inventive beta-lactamases and/or pharmaceutical compositions (and/or additional agents) which hydrolyze a primary antibiotic before it enters the large intestine. In some embodiments, the methods and uses of the present invention relate to the inventive beta-lactamases and/or pharmaceutical compositions (and/or additional agents) which hydrolyze excess antibiotic residue in the GI tract. In some embodiments, methods and uses of the present invention relate to the inventive beta-lactamases and/or pharmaceutical compositions (and/or additional agents) which maintain a normal intestinal micrbiota and/or prevents the overgrowth of one or more pathogenic microorganisms in the GI tract of a patient. In various embodiments, the beta-lactamases and/or pharmaceutical compositions (and/or additional agents) do not substantially interfere with plasma levels of a primary antibiotic. For example, the beta-lactamases and/or pharmaceutical compositions (and/or additional agents) of the present invention allow for a patient to receive a primary antibiotic that might be required for an infection and do not interfere with the systemic utility of the antibiotic. Rather, the beta-lactamases and/or pharmaceutical compositions (and/or additional agents) inactivate excess antibiotic that may populate parts of the GI tract and in doing so, prevent the disruption of the microbiota that is linked to the various disease states described herein.

In various embodiments, the inventive beta-lactamases and/or pharmaceutical compositions (and/or additional agents) are not systemically absorbed. In various embodiments, the inventive beta-lactamases and/or pharmaceutical compositions (and/or additional agents) do not substantially interfere with the activity of systemically administered antibiotics. In various embodiments, the inventive beta-lactamases and/or pharmaceutical compositions (and/or additional agents) function to eliminate antibiotics from interfering with the microbiota of a microbiome (e.g. the gut, including the large intestine). In some embodiments, the inventive beta-lactamases and/or pharmaceutical compositions (and/or additional agents) do not interfere with the antibiotic absorption from the gut and/or enterohepatically sufficiently to alter the half-lives of antibiotic circulation. In some embodiments, the inventive beta-lactamases and/or pharmaceutical compositions (and/or additional agents) do not interfere with the antibiotic absorption from the gut and/or enterohepatically enough to be clinically important.

In some embodiments, the methods and uses of the present invention include those in which an initial and/or adjunctive therapy is administered to a patient. Initial and/or adjunctive therapy indicates therapy that is used to treat CDI and/or *C. difficile* associated disease upon detection of such disease. In some embodiments, the initial and/or adjunctive therapy is one or more of metronidazole, vancomycin, fidaxomicin, rifaximin, fecal bacteriotherapy, probiotic therapy, and antibody therapy, as described herein. In various embodiments, the methods and uses of the present invention include use of the inventive beta-lactamases as an adjuvant to any of these initial and/or adjunctive therapies (including co-administration or sequential administration). In various embodiments, the methods and uses of the present invention include use of the inventive beta-lactamases in a patient undergoing initial and/or adjunctive therapies.

In other aspects, the present invention provides the beta-lactamases and/or pharmaceutical compositions for use in treating an antibiotic-induced adverse effect in the GI tract and/or prevention or treatment of *C. difficile* infection (CDI) and/or a *C. difficile*-associated disease. In other aspects, there are provided uses of the beta-lactamases and/or pharmaceutical compositions for treating an antibiotic-induced adverse effect in the GI tract and/or preventing or treating a *C. difficile* infection (CDI) and/or a *C. difficile*-associated disease. Further, some aspects provide for the use of the disclosed beta-lactamases in the manufacture of a medicament for use in treating an antibiotic-induced adverse effect in the GI tract and/or prevention or treatment of *C. difficile* infection (CDI) and/or a *C. difficile*-associated disease.

In various embodiments, the present invention provides for compositions and methods that mitigate or prevent the overgrowth of various coliforms in a patient's gut (including coliforms that are virulent and/or antibiotic resistant). In various aspects, the methods and compositions described herein prevent or diminish secondary infections with resistant organisms and may, in some embodiments, diminish beta-lactam resistance development. Further, the methods and compositions described herein may allow for use of beta-lactam antibiotics which are currently avoided due to resistance concerns and/or reduce the need for co-administration or co-formulation with one or more beta-lactamase inhibitors (e.g. AUGMENTIN is a mixture of amoxicillin and clavulanic acid).

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In some embodiments, the subject and/or animal is a human. In some embodiments, the human is a pediatric human. In other embodiments, the human is an adult human. In other embodiments, the human is a geriatric human. In other embodiments, the human may be referred to as a patient.

In certain embodiments, the human has an age in a range of from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In other embodiments, the subject is a non-human animal, and therefore the invention pertains to veterinary use. In a specific embodiment, the non-human animal is a household pet. In another specific embodiment, the non-human animal is a livestock animal.

The invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

This invention is further illustrated by the following non-limiting examples.

Examples

The following abbreviations are used throughout:

| Mutations relative to P1A (based on the Ambler classification) | Name |
| --- | --- |
| Wild type | RS310 (or P1A) |
| D276N | IS118 (or P3A) |
| I72S | IS222 |
| T160F | IS203 |
| R244T | IS217 |
| R244T D276K | IS215 |
| Q135M | IS197 |
| G156R A238T | IS235 |
| F33Y D276N | IS158 |
| F33Y S240P D276N | IS230 (or IS181) |
| F33Y A238T D276N | IS232 (or IS180) |
| I72S Q135M T160F (Block 1 mutants) | IS227 |
| A232G A237S A238G S240D | IS191 |

-continued

| Mutations relative to P1A (based on the Ambler classification) | Name |
|---|---|
| (Block 2 mutants) | |
| A232G A237S A238G S240D R244T | IS229 |
| A232G A237S A238G S240D D276R | IS219 |
| A232G A237S A238G S240D D276K | IS221 |
| A232G A237S A238G S240D Q135M | IS224 |
| A238T | IS233 |
| T243I S266N D276N | IS234 (or IS176) |
| A232G A237S A238G S240D D276N | IS288 (or P4A) |

Example 1: Materials and Methods

Different P1A mutants were made either with site-directed mutagenesis using SOE or QUIKCHANGE Multi Site-Directed Mutagenesis Kit (Stratagene, Calif., USA) or with random mutagenesis using GeneMorph® II Random Mutagenesis Kit (Stratagene, Calif., USA). Mutated DNA was transformed into bacteria, either E. coli or B. subtilis, which were screened on cefotaxime (site-directed mutants) or ceftriaxone (random mutants). The presence of P3-lactamase in colonies was further confirmed with a nitrocefin test and the positive colonies were selected for further analysis. The DNA sequences of the mutant β-lactamases were confirmed by sequencing.

β-lactamase activity of the mutants was further characterised from *E. coli* cell lysates and *B. subtilis* growth supernatant with ampicillin, cefotaxime, ceftriaxone, cefuroxime, ceftazidime, meropenem and imipenem. The activities were determined using only one substrate concentration of each antibiotic tested. Selection of the antibiotic concentration was done with the antibiotic concentration as high as was practical, [S]>>Km. Based on these preliminary experiments, more accurate kinetic parameters were determined for a couple of mutants from both the site-directed and the random mutagenesis research lines. All the mutant enzymes selected for more detailed study were expressed in the *B. subtilis* host strain RS303. The cells carrying the mutated proteins were grown in minimal medium over-night after which the cells were harvested and the supernatant was concentrated in 1:10 with Amicon Ultra-4 centrifugal devices, MWCO 10000 (Amicon). Protein concentration in each culture supernatant was estimated from 12% SDS-PAGE (Criterion XT Bis-Tris, BioRad, Calif., USA) using the P1A reference material A18K31 as a standard. Kinetic parameters were measured for cefotaxime, ceftriaxone and cefuroxime for each selected mutant strain. The site-directed mutants were designed to hydrolyze cefotaxime and random mutants were screened with ceftriaxone, which made these antibiotics natural choices for determining kinetic parameters.

P1A Modifications

A series of mutations in P1A were made, including:

TABLE 1

| Mutations on P1A from structure-based design and construction of cefotaxime degrading P1A derivatives, | |
|---|---|
| Block 1 | I72S, Q135M, T160F |
| Block 2 | A232, A237S, A238G, S240D<br>R244T<br>D276R/K |
| Block 1 | I72S, Q135M, T160F<br>and different combinations of these |

Parallel to the site-directed mutagenesis, random mutagenesis was done on P1A and P3A with ceftriaxone as a screening antibiotic.

There are also two modification mutants of P1A that were made for the quality control studies: P1A-N293D (IS205, "the deamidation mutant") and P1A-AMNGK (IS206, "the deletion mutant"). Both of these strains grew equally well as P1A-strain RS310 and the protein production was about the same as well. These mutations did not affect the crystallizability of the protein either.

Sequences of selected CTX-M-enzymes were derived from Swiss-Prot protein sequence data bank and the 3D structures were derived from the Protein Data Bank (PDB). Accession codes for individual sequences and structures are represented below. In some instances, this data was used to predict structure functional activity.

Illustrative Swiss-Prot or TrEMBL, GenBank and Protein Data Bank (PDB) Accession Codes for Enzymes Used in the Study.

| | Swiss-Prot/TrEMBL | GenBank | PDB |
|---|---|---|---|
| CTX-M-9 | Q9L5C8_ECOLI (TrEMBL) | AF174129 | 1YLJ |
| CTX-M-14 | Q9L5C7_ECOLI (TrEMBL) | AF252622 | 1YLT |
| CTX-M-15 | Q9EXV5_ECOLI (TrEMBL) | AY044436 | — |
| CTX-M-16 | Q939K2_KLEPN (TrEMBL) | AY029068 | 1YLW |
| CTX-M-25 | Q8KSA6_ECOLI (TrEMBL) | AF518567 | — |
| CTX-M-44 | Q47066 (Swiss-Prot) | D37839 | 1IYO |

A Linux workstation and Fedora Core 5 operating system was used as the study platform. The sequence alignments and analysis as well as the modelling and 3D structure analysis were performed with Bodil molecular modelling environment.

Additionally, several other P1A mutants were designed and made. One of these mutants was IS288, which has following mutations: A232G, A237S, A238G, A240S and D276N. The four mutations A232G, A237S, A238G and A240S are a so-called "Block2"-mutation. The fifth mutant, D276N, is the "P3A"-mutation, which alone gives the protein's ability to degrade ceftriaxone. The P1A variant IS288 was a result of two rounds of mutagenesis on the P1A gene and preliminary activity assays of secreted P1A variants. Several P1A variants made by site-directed mutagenesis were cloned into the *B. subtilis* production host and produced in shaker flask cultivations. The growth supernatants of these mutant strains were concentrated and used to measure each of the strains' ability to degrade selected cephalosporins. IS288 was produced in larger scale and purified using ammonium sulphate precipitation, hydrophobic interaction chromatography and ultra filtration. The study was set up to characterize the selected P1A variant IS288 in more detail.

In addition to purifying with HIC, methods were developed to further desalt and characterize the amount and purity of protein in the eluted protein peak.

Hydrophobic interaction chromatography, i.e. HIC, is a method, where the separation of bio-molecules is based on interplay between the hydrophobicity of the medium, the nature and composition of the sample, the prevalence and distribution of surface-exposed hydrophobic amino acid residues, and the type and concentration of salt in the binding buffer. The adsorption of protein into the gel matrix is dependent on the concentration of anti-chaotropic salts such as $(NH_4)_2SO_4$ and $Na_2SO_4$; the higher the salt concentration the stronger the adsorption capacity of the HIC medium. The HIC matrix can have different types of hydrophobic substituents, like butyl, octyl, or phenyl groups. Butyl sepharose was selected as the HIC matrix as P1A binds tightly to octyl sepharose that it is not properly eluted.

IS288 Purification Procedure:

The first day, a small amount of a frozen IS288 *Bacillus subtilis* cell culture was streaked on a LB-agar plate containing 10 µg/ml kanamycin. The following morning single cultures were taken from this plate and inoculated into 10×3 ml of minimal growth medium for shaker flask cultivation. In the afternoon of the same day, a volume resulting in a 0.01 starting $OD_{600}$ in the 100 ml overnight (o/n) culture was taken from the 3 ml pre-culture. The 100 ml cultures were incubated in a shaker at +37° C. over night. From a couple of 3 ml pre-cultures $OD_{600}$=1 glycerol stocks (10% glycerol) were made. The glycerol stocks were stored at −70° C.

On the third day after ~16 hours of cultivation, the final $OD_{600}$ of the shaker flask cultivations were measured and cells were centrifuged (Sorvall RC6) with SLA-3000 rotor, 7000 rpm, 10 minutes at +4° C.). Culture supernatants were collected and combined and then filtrated with a 0.2 µm filter. The volume of the filtrate was measured to ~745 ml. 326.86 g of solid $(NH_4)_2SO_4$ resulting in 70% $(NH_4)_2SO_4$ saturation was weighed and added as ~33 g aliquots into the supernatant while continuously mixing. Once all salt had dissolved, the solution was transferred to a +4° C. refrigerator.

The following morning, the ammonium sulphate solution was centrifuged (Sorvall RC6) SLA-3000 rotor, 90 minutes, 10500 rpm, +4° C., acceleration 9 and deceleration 4). After centrifugation, the supernatants were combined and filtered through a 0.2 µm sterile filter. 72.5 ml of the filtrate was taken for hydrophobic interaction chromatography (HIC). The rest of the filtrate was divided into 17×50 ml aliquots and stored first at +4° C. and later transferred to −20° C. Moreover, two 1 ml samples of the filtrate were taken and stored at first at +4° C. and later transferred to −20° C.

The $(NH_4)_2SO_4$ concentration of the ammonium sulphate filtrate was estimated to be ~2.7 M and it was diluted so that the concentration of $(NH_4)_2SO_4$ decreased to ~2 M with 190 mM Na—H-Phosphate buffer, pH 6.8. The filtrate was subjected to HIC in a 5 ml HiTrap Butyl FF column equilibrated with 50 mM Na—H-Phosphate, pH 6.9, 2 M $(NH_4)_2SO_4$. A total of 50 ml of sample was pumped through the column and the flow-through was collected as 5 ml fractions. Unbound sample was washed out with 50 mM Na—H-Phosphate, pH 6.9, 2 M $(NH_4)_2SO_4$. Bound IS288 was eluted with decreasing $(NH_4)_2SO_4$ concentration using step gradient and 50 mM Na—H-Phosphate, pH 6.8. In the first run, elution fractions were 1 ml. Fractions containing the eluted protein were combined in three different sets; C3-C8, C9-D1 and D2-D8. Flow-through fractions and the rest of the elution fractions were stored at +4° C. Samples were taken from flow-through fractions B1 and B8 as well as the pooled protein fractions and stored at +4° C.

The HIC step was repeated two times for different sample volumes, namely 65 ml and 125 ml of equilibrated ammonium sulphate filtrate. These later HIC runs were somewhat modified from the first run. The wash volume for unbound sample was 3 and 4 CV, the volume of flow-through fractions was increased to 10 ml and the volume of the elution fractions was increased to 1.5 ml. No other modifications were made to the running conditions.

Pooled protein fractions as well as flow-through fractions of B1 and B8 of the first run were ultra filtrated and concentrated using Amicon Ultra-4 concentrators with 10000 NMWL. The samples were centrifuged six times and after each centrifugation, except the last one, the rest of the sample or buffer was added into the retentate so as to gain 4 ml volume. After the sixth concentration step, retentates were collected, measured and stored at +4° C. Samples from succeeding HIC runs, as well as one more flow through fraction from the first run were ultra filtrated and concentrated with Amicon Ultra-15 with 10000 NMWL and only four centrifugation rounds were needed. These samples were also stored at +4° C. Ammonium sulphate filtrates were ultra filtrated and concentrated, and flow through fractions were once more concentrated with MultiScreen filter plates with Ultracell-10 membrane, 10000 NMWL. Protein concentration of the flow through samples was measured before this last concentration step whereas no protein concentration was measured for ammonium sulphate filtrates.

The protein concentration of the samples was measured with BCA Protein Assay-kit. Based on the elution peak obtained from Åkta, eluted protein fractions were diluted ~1:20 and ~1:40 while the flow-through fractions were used as such (1:1 dilution) or diluted in half (1:2 dilution).

Finally, samples from all three purifications were run on a Criterion XT 12% Bis-Tris SDS-PAGE using MOPS running buffer to optimally separate proteins of 6-66 kDa in size. The maximum amount of sample was added for ammonium sulphate filtrates and all flow through fractions except for $B1_{121108}$ for which the protein content was determined to be 0.21 µg/µl in the 33× concentrated sample. The amount of protein peak fractions pipetted was calculated so that 0.5 µg of protein would be loaded on the gel.

A purified protein solution of IS288 was used to determine the activity of IS288 per mass unit. The stability of IS288 in storage conditions was examined to find out if the protein is degraded or by some other way modified during storage. The stability of the protein at the target site matrix was also determined. The results from the stability assay in target site matrix were combined with the results from the activity assay to estimate the time it takes for IS288 to eliminate antibiotic residues in the small intestine.

In addition to getting more detailed information on P1A variant IS288, the characterization scheme created during the study was used in the characterization of other subsequent P1A variants.

Method to Study Production Levels of P1A Variant IS288

During the *Bacillus subtilis* shaker flask cultivation, samples were taken at various time points to evaluate the production level of IS288. The $OD_{600}$ value was measured for each of the time points as well to see how the cells were growing. The amount of produced protein was estimated on SDS-PAGE.

Method to Study Enzyme Efficacy and Antibiotic Spectrum at Different pH Levels

The antibiotics used in this study were a selection of, e.g., intravenously administered cephalosporins. The concentrations of selected antibiotics were, without wishing to be bound by theory, set to as close to the in literature reported concentrations in bile or duodenum as possible. This experiment was also performed at varying pHs.

Method to Study Enzyme Stability in Human Ileal Chyme

Different amounts of purified enzyme were incubated in human ileal chyme at the appropriate temperature for a set period of time. Samples were taken at different time points. The degradation pattern of IS288 was analysed with SDS-PAGE and the activity of IS288 was analysed using nitrocefin as a substrate.

Compounds and Bacterial Strain: Ampicillin, Ceftriaxone, Ceftazidime, Meropenem, Cefepime, Cefazolin, Amp/Sulbactam, Cefoperazone, Cefotaxime, and Cefuroxime were purchased from commercial sources and stored as frozen stocks of 15 mg/mL and 10 mg/mL, respectively. P1A was supplied by Synthetic Biologics as a stock concentration of 32 mg/mL and stored at −80° C. *Escherichia coli* ATCC 25922 was obtained from American Type Culture Collection (ATCC, Manassas, Va.).

Determination of the Effective Inhibitory Concentration in the Absence and Presence of P1A (RS310), P3A (IS118), and P4A (IS288): The effective inhibitory concentrations (EC50, 90) of ampicillin, ceftriaxone, ceftazidime, meropenem, cefepime, cefazolin, amp/sulbactam, cefoperazone, cefotaxime, and cefuroxime were determined by microbroth dilution analysis according to the CLSI guidelines (M07-A9: Methods for Dilution Antimicrobial Susceptibility Tests for Bacteria That Grow Aerobically; Approved Standard—Ninth Edition). *Escherichia coli* strain 25922 was cultured from glycerol stocks to logarithmic growth in cation adjusted Mueller-Hinton broth at 37° C. in an atmospheric environment and diluted in cation adjusted Mueller-Hinton broth to achieve a starting in well concentration of 5×105 CFU/mL. Serial 2-fold dilution of antimicrobial compounds were prepared in cation adjusted Mueller-Hinton broth to achieve final in well concentration of 128 µg/mL to 0.13 µg/mL for ampicillin and 4 µg/mL 4 ng/mL in the absence or presence of serial 10-fold dilutions of P1A, P3A, or P4A β-lactamase standard, 5 µg/mL to 50 ng/mL for ampicillin and 50 µg/mL to 500 ng/mL for ceftriaxone, ceftazidime, meropenem, cefepime, cefazolin, amp/sulbactam, cefoperazone, cefotaxime, and cefuroxime. Antibiotics were either added to the P1A and incubated for 30 min at 37° C. (pre-incubation) prior to addition of bacteria, or added to the plates following the addition of P1A, P3A, P4A, and bacteria (simultaneous). All concentrations and combinations were evaluated in triplicate in a 96-well plate format that contained media only, compound plus media only (colorimetric control), and untreated bacterial controls. Following overnight incubation, the OD625 of the plates was measured in a Spectramax 384 plate reader and the data were imported into a customized Excel spreadsheet for the determination of the effective concentration that inhibited bacterial growth by 50%, 90% and 99% (EC50, 90, 99) by linear regression analysis.

Example 2: Results of Mutagenesis

Mutation design was based on, inter alia, structural data (e.g. crystal structure data, homolog models, etc.) of the following: P1A crystal structure (Knox and Moews, *J. Mol Biol.*, 220, 435-455 (1991)), CTX-M-44 (1BZA (Ibuka et al. *Journal of Molecular Biology* Volume 285, Issue 5 2079-2087 (1999), 1 IYS (Ibuka et al. *Biochemistry,* 2003, 42 (36): 10634-43), 1IYO, 1IYP and 1IYQ (Shimamura et al. 2002 *J. Biol. Chem.* 277:46601-08), *Proteus vulgaris* K1 (1HZO, Nugaka et al. *J Mol Biol.* 2002 Mar. 15; 317(1):109-17) and *Proteus penneri* HugA (Liassine et al. *Antimicrob Agents Chemother.* 2002 January; 46(1):216-9. 2002), and reviewed in Bonnet, *Antimicrob. Agents Chemother* 48(1): 1-14 (2004) (for CTM-X), the contents of all of these documents are hereby incorporated by reference in their entirety). In some embodiments, the present mutations are informed by analysis of structural data (e.g. crystal structure data, homolog models, etc.) of any one of the following β-lactamases: P1A, P2A, P3A, CTX-M-3, CTX-M-4, CTX-M-5, CTX-M-9, CTX-M-10, CTX-M-14, CTX-M-15, CTX-M-16, CTX-M-18, CTX-M-19, CTX-M-25, CTX-M-26, CTX-M-27, CTX-M-32, CTX-M-44, CTX-M-45, and CTX-M-54. Such information is available to one skilled in the art at known databases, for example, Swiss-Prot Protein Sequence Data Bank, NCBI, and PDB.

Results from site-directed and random mutagenesis are summarized in Tables 2 and 3, respectively. Enzymatic activity for selected mutants is presented in Table 4 and kinetic parameters are represented in Table 5. Kinetic parameters for previous enzymes P1A, P3A and P2A are also included in that table.

Mutation Block 1. I72S, Q135M and T160F

The first block of mutations including I72S, Q135M and T160F were introduced in mutagenic primers in one reaction using The QUIKCHANGE Multi Site-Directed mutagenesis kit (for short later called Multi kit), Stratagene. Plasmid carrying the penP gene was used as template in the mutagenesis reaction. Mutant single-stranded plasmids were transformed into *E. coli* XL10Gold and selected with kanamycin/chloramphenicol. Competent XL10 Gold cells are provided with the Multi kit. Colonies (10-30) were picked and tested with nitrocefin to verify β-lactamase activity. Part of the colony was used as template in PCR and the resulting fragment, if clean, was sent to DNA sequencing. The rest of the colony was cultivated in Luria supplemented with appropriate antibiotic, overnight, at 37° C., and a part of the culture was stored in glycerol (≤10%, final), another part is used for plasmid isolation. After the desired mutations were confirmed with DNA sequencing, the mutant clones were characterized in more detail. Periplasmic lysates were prepared and analyzed in SDS PAGE and the kinetics of cefotaxime hydrolysis were measured spectrophotometrically.

Mutation Block 2. A232G, A237S, A238G and S240D

Figure 7:
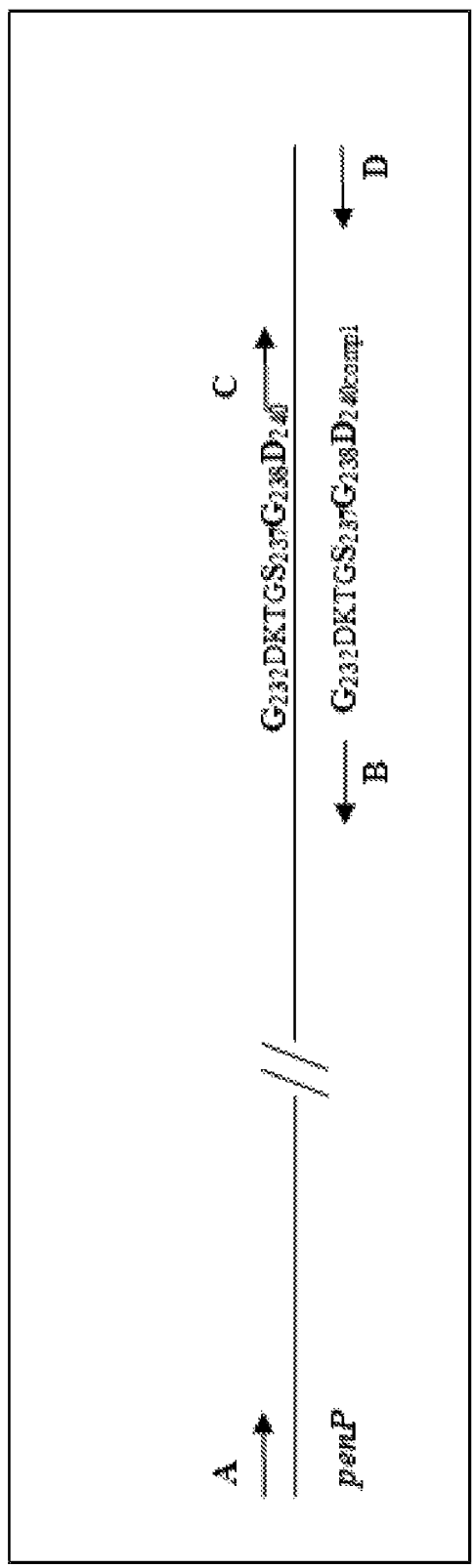
FIG. 7 demonstrates the SOE (spliced overlap extension) technique. The target amino acids of the B3 β-strand of P1A are so closely situated to each other that all four amino acids can be exchanged using the SOE technique. The region encompassing the exchanges contains 24 nucleotides (8 herein, mutations may be made to this sequence to generate the inventive beta-lactamases.

The target amino acids of the B3 β-strand of P1A are so closely situated to each other that the Multi-Site protocol was not suitable, at least in one round. Instead, all four amino acids were exchanged using the SOE technique. The region encompassing the exchanges contained 24 nucleotides (8 amino acid codons) and was included in the overlap extension part of two PCR primers. The mutated penP gene was first PCR'ed in two parts, using primers A+B and C+D (FIG. 7). The two PCR products were then combined and amplified using primers A and D, complementary to the 5' and 3' parts of the penP gene. Cloning sites were included in primers A and D. Once the construct was ready, further mutations were added using the Multi kit.

Further Mutations, R244T and D276R(K)

These mutations were added using the Multi-Site kit technique and the previously made mutant plasmids as templates. A list of the constructed mutations is shown in Table 1. The number of mutation combinations was increased easily and consequently, the characterization was done with more robust methods than measuring the cefotaxime degradation kinetics of individual clones. Primary characterization was the determination of the cefotaxime MIC.

TABLE 1

Constructed mutations and other possible combinations

| Clone | Technique | Amino acid replacements |
|---|---|---|
| Block 1 | Multi kit | I72S, Q135M, T160F |
|  | Multi kit | I72S, T160F |
|  | Multi kit | I72S, Q135M |
|  | Multi kit | I72S |
|  | Multi kit | Q135M |
|  | Multi kit | T160F |
| Block 2 | SOE | A232G, A237S, A238G, S240D |
|  | SOE + Multi kit | A232G, A237S, A238G, S240D + R244T |
|  | SOE + Multi kit | A232G, A237S, A238G, S240D + D276R(K) |
|  | SOE + Multi kit | A232G, A237S, A238G, S240D + R244T + D276R(K) |
|  | SOE + Multi kit | A232G, A237S, A238G, S240D + I72S, Q135M, T160F |
|  | SOE + Multi kit | A232G, A237S, A238G, S240D + I72S, Q135M, T160F + R244T |
|  | SOE + Multi kit | A232G, A237S, A238G, S240D + I72S, Q135M, T160F + D276R(K) |
|  | SOE + Multi kit | A232G, A237S, A238G, S240D + I72S, Q135M, T160F + R244T + D276R(K) |
|  | Multi kit | R244T |
|  | Multi kit | D276R(K) |
|  | Multi kit | R244T + D276R(K) |
|  | Multi kit | I72S, Q135M, T160F + R244T |
|  | Multi kit | I72S, Q135M, T160F + D276R(K) |
|  | Multi kit | I72S, Q135M, T160F + R244T + D276R(K) |

TABLE 2

P1A mutants made using site-directed mutagenesis. *B. subtilis* and *E. coli* strain numbers, mutations and plasmid names are marked.

| B. subtilis strain | Amino acid replacements | Plasmid name in B. subtilis | E. coli strain |
|---|---|---|---|
| IS191 | Block 2 = A232G, A237S, A238G, S240D | pCTX-42 | IS189 |
| IS197 | Q135M | pIS197 | IS193 |
| IS215 | R244T + D276K | pIS215 | IS207 |
| IS217 | R244T | pIS217 | IS108 |
| IS219 | Block 2 + D276T | pIS219 | IS209 |
| IS221 | Block 2 + D276K | pIS221 | IS210 |
| IS222 | I72S | pIS222 | IS212 |
| IS224 | Block 2 + Q135M | pIS224 | IS214 |
| IS227 | Block 1 = I72S, Q135M, T160F | pRSH227 | SOE |
| IS229 | Block 2 + R244T | pRSH229 | SOE |

TABLE 3

P1A mutants generated with random mutagenesis. *B. subtilis* and *E. coli* strain numbers, mutations and plasmid names are marked.

| B. subtilis strain | Amino acid replacements | Plasmid name in B. subtilis | E. coli strain |
|---|---|---|---|
| IS158 | F33Y, D276N | pRSH158 |  |
| IS230 | F33Y, S240P, D276N | pRSH230 | IS181 |
| IS232 | F33Y, A238T, D276N | pRSH232 | IS180 |
| IS234 | R55R, A123A, T243I, S266N, D276N | pRSH234 | IS176 |

TABLE 4

Preliminary enzymatic activities of P1A mutants measured from *B. subtilis* supernatants. Values are represented as multiples of P1A.

| B. subtilis strain | Amino acid replacements | AMP | CTX | CRO | CXM | CAZ |
|---|---|---|---|---|---|---|
| RS310 | P1A strain | 1.00 | 1.00 | 1.00 | 1.00 | 1.00 |
| IS191 | A232G A237S A238G S240D | 0.16 | 2.17 | 2.91 | 3.22 | 1.28 |
| IS197 | Q135M | 0.15 | 1.32 | 1.09 | 1.83 | 0.55 |
| IS203 | T160F | 0.01 | 0.01 | 0.00 | 0.00 | 0.13 |
| IS215 | R244T D276K | 0.44 | 0.50 | 0.93 | 0.81 | 0.26 |
| IS217 | R244T | 0.22 | 0.00 | 0.00 | 0.05 | 0.11 |
| IS219 | A232G A237S A238G S240D D276R | 0.05 | 7.22 | 15.99 | 7.67 | 0.27 |
| IS221 | A232G A237S A238G S240D D276K | 0.06 | 9.39 | 15.95 | 9.87 | 0.38 |
| IS222 | I72S | 0.71 | 0.00 | 0.15 | 0.18 | 0.00 |
| IS224 | A232G A237S A238G S240D Q135M | 0.02 | 4.74 | 5.18 | 6.37 | 1.24 |
| IS230 | F33Y S240P D276N | 0.02 | 8.07 | 9.26 | 4.76 | 8.98 |
| IS232 | F33Y A238T D276N | 0.08 | 12.34 | 9.14 | 5.71 | 26.73 |
| IS233 | A238T | 0.07 | 4.17 | 5.25 | 4.76 | 12.70 |
| IS234 | T243I S266N D276N | 0.57 | 6.04 | 11.03 | 6.86 | 11.23 |
| IS235 | G156R A238T | 0.03 | 1.66 | 2.09 | 1.34 | 5.42 |

AMP = ampicillin, CTX = cefotaxime, CRO = ceftriaxone, CXM = cefuroxime and CAZ = ceftazidime.
P1A values used for the calculations are means of two different experiments.

TABLE 5

Kinetic parameters measured for the P1A mutant strains. Kinetic parameters for IS230 degrading cefuroxime are not reliable as the original curve did not obey Michaelis-Menten kinetics. Moreover, it should be noted that kinetic parameters for IS219 and IS221 are near one another except when cefotaxime is degraded; when the $V_{max}$ for IS219 is increased, it is decreased for IS221. On the other hand, the affinity of IS219 towards cefotaxime has not increased with the same amount as IS221's.

| | Ceftriaxone | | | | Cefotaxime | | | | Cefuroxime | | | |
|---|---|---|---|---|---|---|---|---|---|---|---|---|
| | $V_{max}$ (nmol/s) | $K_m$ (mM) | $k_{cat}$ (1/s) | $k_{cat}/K_m$ ($M^{-1} * s^{-1}$) | $V_{max}$ (nmol/s) | $K_m$ (mM) | $k_{cat}$ (1/s) | $k_{cat}/K_m$ ($M^{-1} * s^{-1}$) | $V_{max}$ (nmol/s) | $K_m$ (mM) | $k_{cat}$ (1/s) | $k_{cat}/K_m$ ($M^{-1} * s^{-1}$) |
| P1A (A18K31) | 2.81 | 179 | 25 | $1.41 * 10^5$ | 1.18 | 232 | 16 | $6.8 * 10^4$ | 1.25 | 107 | 23 | $2.11 * 10^5$ |
| IS219 | 0.37 | 47 | 171 | $3.62 * 10^6$ | 1.51 | 164 | 60 | $3.68 * 10^5$ | 0.94 | 140 | 126 | $8.98 * 10^5$ |
| IS221 | 0.30 | 30 | 103 | $3.46 * 10^6$ | 0.43 | 66 | 43 | $6.47 * 10^5$ | 0.90 | 108 | 89 | $8.22 * 10^5$ |
| IS227 | Low | Low | Low | Low | Low | Low | Low | Low | | | | |
| IS229 | Low | Low | Low | Low | 3.10 | 574 | 136 | $2.37 * 10^5$ | | | | |
| P3A(1 | 0.25 | 55 | 54 | $9.89 * 10^5$ | 0.24 | 230 | 17 | $7.3 * 10^4$ | ND | ND | ND | ND |
| IS158 | 1.27 | 33 | 45 | $1.36 * 10^6$ | 0.57 | 144 | 20 | $1.41 * 10^5$ | ND | ND | ND | ND |
| IS232 (IS180) | 0.47 | 4 | 27 | $6.25 * 10^6$ | 0.31 | 14 | 23 | $1.69 * 10^6$ | low | low | low | low |
| IS234 (IS176) | 1.09 | 37 | 53 | $1.45 * 10^6$ | 0.61 | 33 | 30 | $8.88 * 10^5$ | 0.77 | 17 | 38 | $2.19 * 10^6$ |
| IS230 (ISI81) | 0.66 | 18 | 32 | $1.80 * 10^6$ | 0.47 | 21 | 23 | $1.09 * 10^6$ | 0.50 | 7 | 24 | $3.27 * 10^6$ |
| P2A(1 | | 68 | 95 | $1.40 * 10^6$ | 0.79 | 66 | 479 | $7.28 * 10^6$ | 0.37 | 27 | 221 | $7.99 * 10^6$ |

Low = not enough activity for measurements; ND or empty cell = not done.

TABLE 6

$V_{max}$ and $K_m$ values of selected mutants represented as relative values of P1A activities. If $K_m < 1.0$, the mutant's affinity towards its ligand increased. If $K_m > 1.0$, the affinity decreased. The opposite is true for $k_{cat}$ and $V_{max}$.

| | Ceftriaxone | | | | Cefotaxime | | | | Cefuroxime | | | |
|---|---|---|---|---|---|---|---|---|---|---|---|---|
| | $V_{max}$ | $K_m$ | $k_{cat}$ | $k_{cat}/K_m$ | $V_{max}$ | $K_m$ | $k_{cat}$ | $k_{cat}/K_m$ | $V_{max}$ | $K_m$ | $k_{cat}$ | $k_{cat}/K_m$ |
| P1A (A18K31) | 1.00 | 1.00 | 1.00 | 1.00 | 1.00 | 1.00 | 1.00 | 1.00 | 1.00 | 1.00 | 1.00 | 1.00 |
| IS219 | 0.13 | 0.26 | 6.76 | 25.64 | 1.29 | 0.71 | 3.81 | 5.39 | 0.75 | 1.31 | 5.56 | 4.25 |
| IS221 | 0.11 | 0.17 | 4.09 | 24.46 | 0.37 | 0.29 | 2.70 | 9.48 | 0.71 | 1.01 | 3.93 | 3.89 |
| IS227 | low | low | low | low | low | low | low | low | — | — | — | — |
| IS229 | low | low | low | low | 2.64 | 2.47 | 8.58 | 3.47 | — | — | — | — |
| P3A | 0.09 | 0.31 | 2.15 | 7.00 | 0.20 | 0.99 | 1.07 | 1.07 | — | — | — | — |
| IS158 | 0.45 | 0.19 | 1.80 | 9.63 | 0.48 | 0.62 | 1.28 | 2.06 | — | — | — | — |
| IS232 (IS180) | 0.17 | 0.02 | 1.08 | 44.25 | 0.26 | 0.06 | 1.44 | 24.70 | — | — | — | — |
| IS234 (IS176) | 0.39 | 0.20 | 2.10 | 10.26 | 0.52 | 0.14 | 1.87 | 13.00 | 0.61 | 0.16 | 1.66 | 10.38 |
| IS230 (IS181) | 0.24 | 0.10 | 1.27 | 12.70 | 0.40 | 0.09 | 1.45 | 15.99 | 0.40 | 0.07 | 1.08 | 15.48 |
| P2A | — | 0.38 | 3.76 | 9.87 | 0.67 | 0.28 | 30.18 | 106.55 | 0 29 | 0.25 | 9.78 | 37.81 |

Low = low activity; — = not done

Enzymatic Activity and Kinetic Parameters

From the kinetic parameters measured for P1A against cefotaxime, ceftriaxone and cefuroxime, without wishing to be bound by theory, it was deduced that P1A has a low intrinsic cephalosporinase activity. In general, the mutants' affinity towards ligands has increased (i.e. decreased Km). $V_{max}$ increased and the affinity decreased (Km increased) in the IS229 (Block 2+R244T) mutant (Table 5). For IS229, the $k_{cat}$ increased the most.

The random mutagenesis screen with ceftriaxone preferred mutants with low Km (high affinity) towards the antibiotic. Decrease in Km by subsequent mutation rounds was seen in the mutation series P3A→IS158→IS232; IS232 had extremely high affinity towards ceftriaxone. The $V_{max}$ for ceftriaxone did not decrease sequentially being the highest for IS158 but $k_{cat}$, nevertheless, decreased through the mutation rounds. The first two mutants of this round did not have cefotaximase activity but IS232 with additional A238T had cefotaximase activity.

Site-directed Block2 (IS191) mutations alone did not markedly increase P1A-derivative's activity towards cephalosporins but the activity towards ampicillin was reduced 20 fold (Table 4). The cephalosporinase activity of Block2+ D276R/K (IS219/IS221) was considerably better than that of IS191's. The kinetic parameters of the IS219 and IS221 site-directed mutants revealed that the site-directed mutagenesis preferably increased the enzyme's affinity towards the target antibiotics.

Stability Assay/Glucose Stress Test

To test the stability of mutants in B. subtilis growth conditions, a shaker flask cultivation with RS310, IS219 and IS232 was performed. The cultivation was made in two different glucose concentrations of 5 g/l and 10 g/l.

Figure 2:
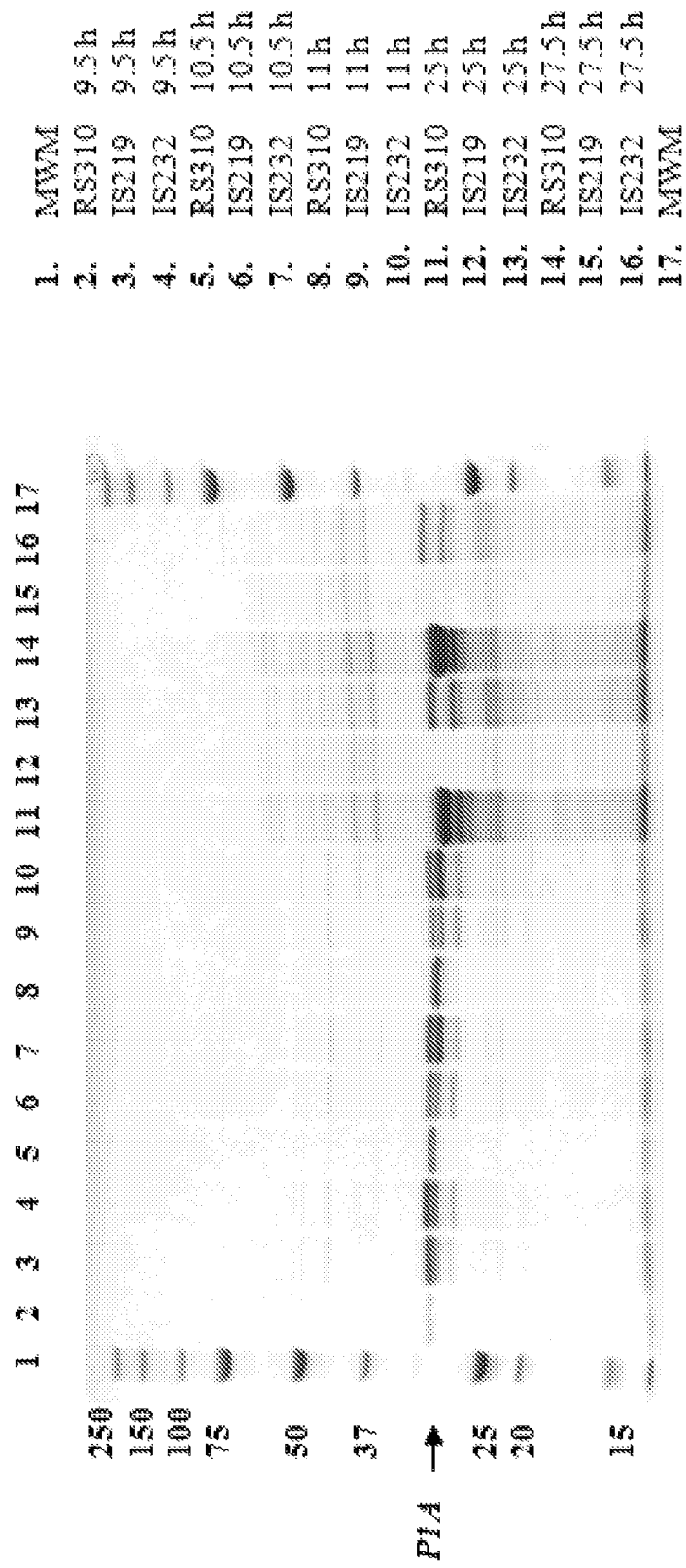
FIG. 2 shows a 12% Bis-Tris Criterion XT SDS-PAGE (BioRad) gel with supernatant samples (see labels of the samples to the right of the gel) from a 5 g/l glucose *B. subtilis* growth. 14 µl of each supernatant was applied on the gel. MWM=molecular weight marker Precision Plus (BioRad), RS310=P1A *B. subtilis* strain and "P1A→" denotes the right size of P1A and the mutant proteins.

P1A (RS310) and the two mutants IS219 and IS232 were cultivated in shaker flasks (100 ml) in minimal medium with 5 or 10 g/l glucose. The condition of the cells was monitored with microscope, the glucose consumption measured from 5 g/l growth and samples from the culture supernatants (concentrated and non-concentrated) were run on 12% Bis-Tris SDS-PAGE (Criterion, BioRad) (FIGS. 1 and 2). The ODs of the cell cultures were also monitored.

In 10 g/l glucose cultures, P1A and IS232 were produced in comparable amounts but the production of IS219 was lower (lanes 2-4, FIG. 1). During concentration, the IS219 yield was further reduced (lanes 6, 9 and 16, FIG. 1). A faint band ~29 kDa can be seen on lane 16 in FIG. 1. P1A and IS232, again, could be concentrated (lanes 5, 7, 8, 10, 15 and 16 FIG. 1).

In the presence of 5 g/l glucose, P1A strain RS310 started growing slower than the other two strains. However, by the end of the cultivation the amount of P1A had superseded the amount of the other proteins (FIG. 2). The mutant strain IS219 started to produce roughly at the same velocity as the strain IS232 but by 10 hours of cultivation its production had started to lag behind IS232 and its amount was decreased over time. All glucose was consumed by 9.5 hours of cultivation both in IS219 and IS232 cultivations and from that point on it is assumed that the amount of proteases started to increase. Because RS310 grew slower, it still had some glucose left at 11 hours of cultivation but also RS310 had consumed all glucose by the following morning. Because no samples were taken from RS310 during the night, the exact time-point at which RS310 had used all its glucose and started to produce proteases cannot be stated. By 27.5 hours of cultivation the amount of P1A had increased but the amount of both IS219 and IS232 had decreased from the previous day. From the study, without wishing to be bound by theory, it can be deduced that IS232 tolerates proteases better than IS219, which does not tolerate them at all.

Based both on 10 g/l glucose and 5 g/l glucose cultivations, without wishing to be bound by theory, it can be said that modifications to P1A reduce the protein's protease tolerance. Glucose deprivation lead to the appearance of degradation products in the case of IS219 and IS232 and the amount of degradation products was increased after all glucose was consumed. IS219 protein was more sensitive to degradation as its amount decreased more than that of IS232. Without wishing to be bound by theory, this may indicate either lower secretability or greater sensitivity to *Bacillus* proteases, or both. In conclusion, production of IS219 was not possible using the same growth conditions as for RS310 and IS232. The glucose stress test also demonstrated that this test can be used to estimate the protease tolerance of the generated mutants.

Figure 5:
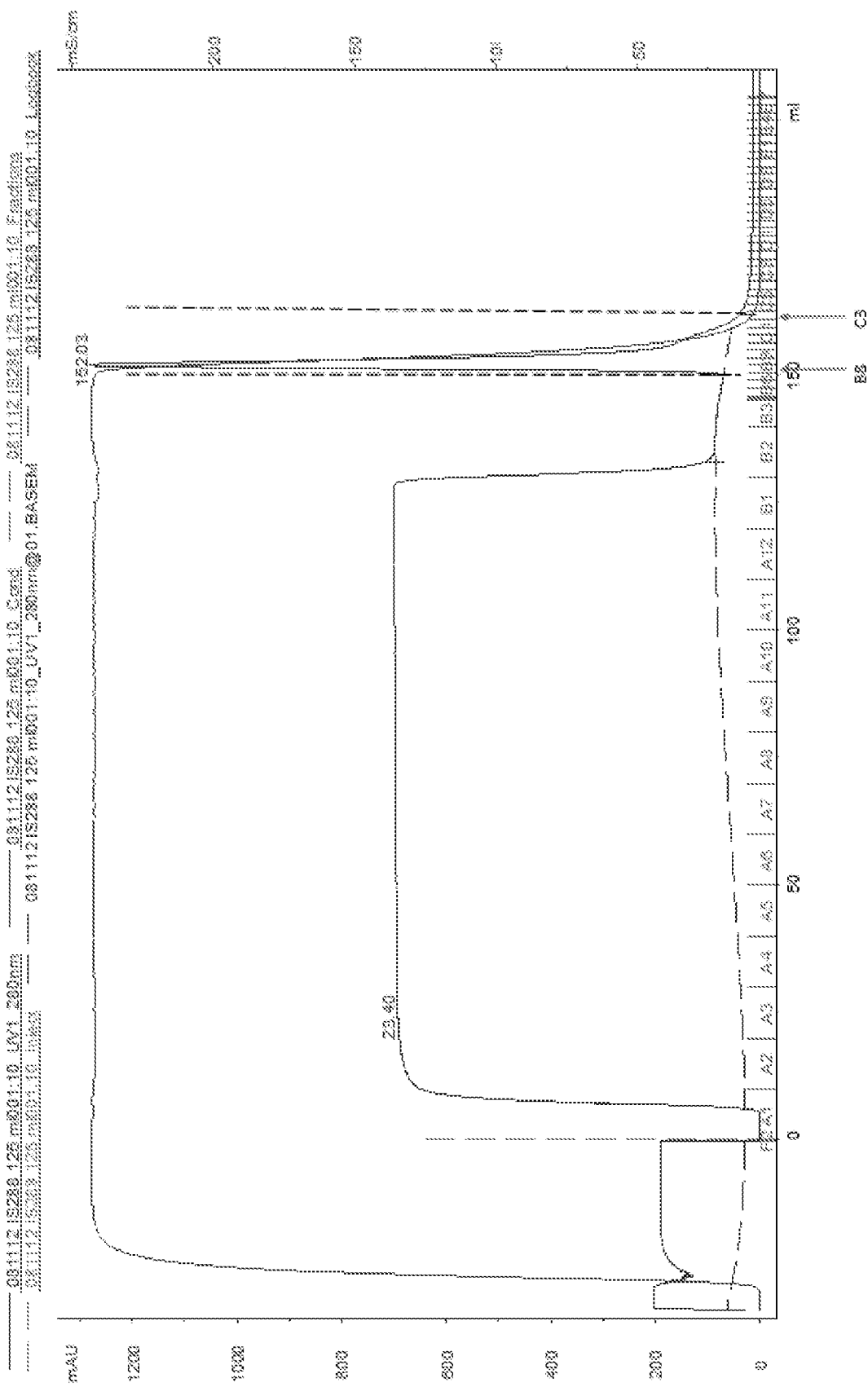
FIG. 5 shows an elution diagram from a HIC run. The places of collected elution fractions are marked with arrows and black dashed lines (dashed lines farthest to the right) both perpendicular to the X-axis. Flow-through fractions A1-B1 can be easily seen on the diagram. The $A_{280}$ graph is represented with a solid line (second line from the top), conductivity of the eluted solution by a solid line (top line). Sample injection is marked with a dashed line (dashed line farthest to the left) and fractions with multiple solid lines both perpendicular to the X-axis. The section before zero at the X-axis represents the column equilibration with buffer A.

With the glucose stress test it was demonstrated that Block2+D276R=IS219 (and most likely Block2+D276K=IS221) mutation decreases the enzyme's protease tolerance. Most likely, without wishing to be bound by theory, the instability is due to D276R mutation, which creates a protease cleavage site on the surface of the protein.

A D276N mutation on IS191, which would result in a Block2+D276N-mutant was made. Without wishing to be bound by theory, an aspartic acid to asparagine mutation is expected to increase the ceftriaxone (and maybe cefotaxime) activity of IS191 but at the same time keep the enzyme more resistant to proteases than IS219 (and IS221) is. R244T mutation could be combined with Block2 and D276N to see whether we can increase the $V_{max}$ (and $k_{cat}$) with this mutation. R244T mutation could also be combined with IS219 and IS221.

An activity assay (Table 4) R244T (IS217) mutation abolished nearly all enzymatic activity of P1A. Some of the activity was gained with a double mutant R244T+D276K (IS215), but not to the level of the wild type enzyme. Thus, R244T mutation alone cannot provide P1A with cephalosporinase activity.

Based on kinetic data (Table 5) Block1 mutation (I72S/Q135M/T160F, IS227) did not improve P1A's ability to hydrolyze cephalosporins. In other activity assays neither did Q135M or T160F alone increase P1A's ability to hydrolyze cephalosporins, instead, both single mutations abolished nearly all P1A's enzymatic activity, even towards ampicillin. There was, however, a Block2+Q135M-mutant (IS224), which had an activity towards cefotaxime and ceftriaxone between Block2 (IS191) and Block2+D276R/K (IS219/IS221) mutants. Without wishing to be bound by theory, Block1 may "loosen" the O-loop where the catalytic Glu166 is located. T160F mutation is quite a large modification in the core of a protein's structure. It might disrupt the structure totally or at least incapacitate the protein from functioning properly. To avoid this possibility, two compensatory mutations were added to accompany T160F mutation in P1A, namely I72S and Q135M and this combination of mutations was called "Block1".

Example 3: Results from Production and Purification of P1A Mutant IS288

The results of the purification are reported as elution peak figures (FIGS. 3, 4, and 5) and peak tables, as protein concentration and as SDS-PAGE picture(s) (FIG. 6).

Chromatograms from Hydrophobic Interaction Chromatography

Hydrophobic interaction chromatography (HIC) was run on three separate occasions with differing parameters. In the first run (16 Oct. 8, FIG. 3) the sample volume was ~50 ml, volume of flow through fractions 5 ml, wash volume for the unbound sample 2 CV, and the volume of eluted fractions 1.0 ml. In the following HIC run (Apr. 11, 2008, FIG. 4) the sample volume was increased to 65 ml, flow-through fraction volume to 10 ml, and wash volume for unbound sample to 3 CV and fraction size to 1.5 ml. In the last run (Dec. 11, 2008, FIG. 5) only the sample volume and wash volume for unbound sample differed from the preceding run being 125 ml and 4 CV, respectively.

All the graphs of HIC runs (FIGS. 3, 4, and 5) represent the same overall form. The flow through fraction gave constant absorbance ~700 mAU at 280 nm throughout the sample application while during washing of unbound sample, the absorbance at 280 nm dropped to zero rising again when the bound protein was eluted. The conductivity of the sample was slightly lower in samples applied in FIG. 3 and FIG. 4 than in running buffer A containing 2 M $(NH_4)_2SO_4$ while in the run on Dec. 11, 2008 it stayed the same as in the A-buffer. In the two first runs the $(NH_4)_2SO_4$ concentration of the ammonium sulphate filtrate was estimated as 2.7 M and in the last run 2.6 M. It seems that the 2.6 M estimation was closer to the actual $(NH_4)_2SO_4$ concentration of the ammonium sulphate filtrate as the conductivity of the out coming solution did not drop during sample application (FIG. 5).

The elution that started right after the elution buffer (buffer B) was applied on the column. This indicated that the protein in the sample was barely bound to the column as it eluted so early in the gradient. Thus, it was vital that the conductivity of the sample never got less than ~240 mS/cm.

Figure 3:
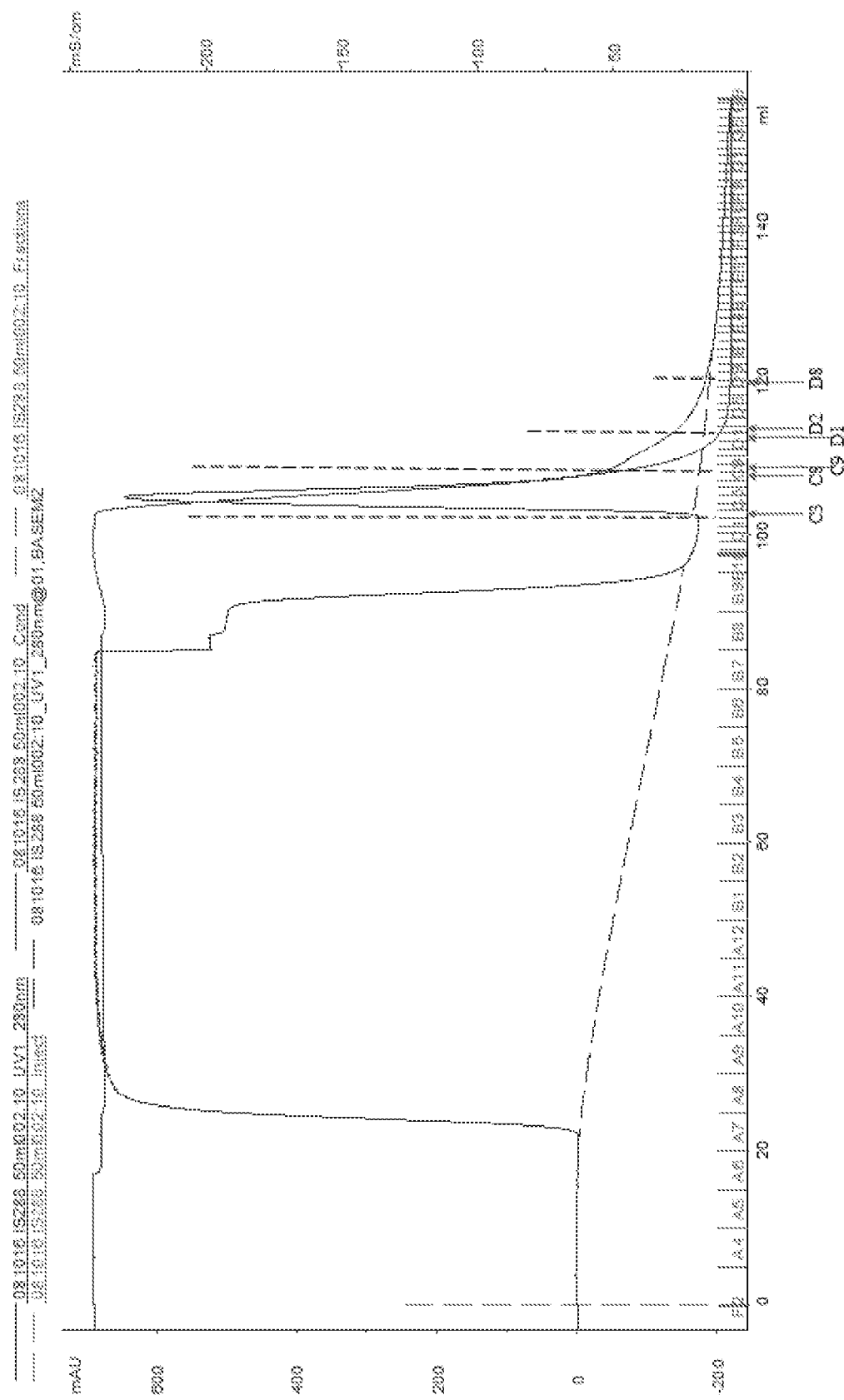
FIG. 3 shows an elution diagram from a HIC run. The places of collected elution fractions are marked with arrows and black dashed lines (dashed lines farthest to the right) both perpendicular to the X-axis. Flow-through fractions A7-B8 can be easily seen on the diagram. The $A_{280}$ graph is represented with a solid line (top line), conductivity of the eluted solution by a solid line (second line from the top). Sample injection is marked with a dashed line (dashed line farthest to the left) and fractions with multiple solid lines both perpendicular to the X-axis.
Figure 4:
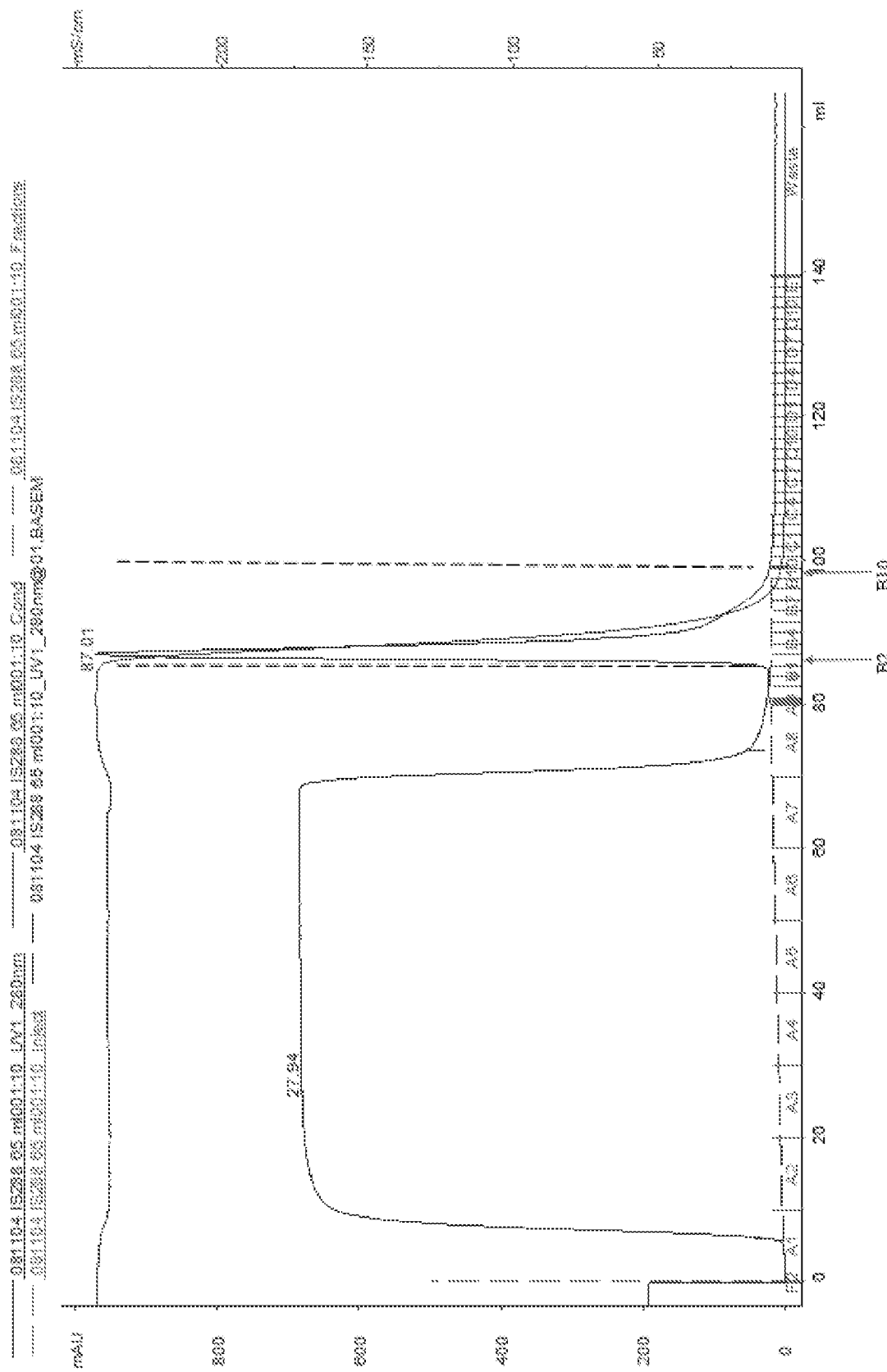
FIG. 4 shows an elution diagram from a HIC run. The places of collected elution fractions are marked with arrows and black dashed lines (dashed lines farthest to the right) both perpendicular to the X-axis. Flow-through fractions A1-A8 can be easily seen on the diagram. The $A_{280}$ graph is represented with a solid line (second line from the top), conductivity of the eluted solution by a solid line (top line). Sample injection is marked with a dashed line (dashed line farthest to the left) and fractions with multiple solid lines both perpendicular to the X-axis.

The bound protein eluted as a typical elution peak with steep ascending slope and a gentle descending slope giving slightly asymmetrical peak. The size of the peak was largest in the first run, ~18 ml (18×1 ml fractions) (FIG. 3). This peak was collected in three sets: first of 6 ml (fractions C3-C8), second of 5 ml (fractions C9-D1) and third of 7 ml (fractions D2-D8) as there was a "shoulder" in the elution peak between fractions C8 and C9 and it was considered that the last 7 fractions could be too diluted for concentration. In the two subsequent HIC runs (Apr. 11, 2008 and Dec. 11, 2008, FIGS. 4 and 5, respectively) the elution peak was 13.5 ml (9×1.5 ml fractions, Apr. 11, 2008) and 12 ml (8×1.5 ml fractions, Dec. 11, 2008) and the whole peak was pooled to one fraction.

In Table 7, the statistical values for $A_{280}$ graphs of the three HIC runs are given. The area of the peak was used to estimate the protein content of that sample and it was used in estimating the dilution factor for different samples in the BCA assay. The calculations required the theoretical extinction coefficient of the protein, which was calculated using ProtParamTool at ExPASy web service. For IS288, this coefficient was 25440 $M^{-1}$ $cm^{-1}$ and gave $A_{280}$ 0.869 for 0.1% (=1 g/l) solution.

Using the proportion above, the amounts of protein in eluted protein samples and the known volumes of these samples, the protein amount eluted from the column was calculated. The formula used was: $((mAU*ml)*10^{\wedge}-3/V_{fraction})/0.869*V_{fraction} \rightarrow (mAU*ml)*10^{\wedge}-3/0.869$, which resulted in: 3.36 mg protein 161008, 2.95 mg 041108, and 3.60 mg 121108.

Ultra Filtration and Concentration of Flow-Through and Eluted Protein Fractions

From each of the purifications one, two or three of the flow-through fractions were selected for concentration as well as all fractions containing the eluted protein peak. The selected samples are represented in Table 8. Also represented in the table are the starting volume of that sample as well as final volume and concentration factor.

TABLE 8

Samples selected for ultra filtration and concentration
with Amicon Ultra-4, 10000 NMWL
The original volume of the sample and the final volume of the sample
after concentration as well as the concentration factor are presented.
The concentration factor was calculated by dividing the original
volume by the final volume of the sample after concentration.

| Date of purification | Selected fractions | Original volume (ml) | Final volume (µl) | Conc. factor |
| --- | --- | --- | --- | --- |
| 16th Oct. 2008 | B1 (FT) | 5 | 750 | 6.7 X |
| | B7 (FT) | 4.5 | 1000 | 4.5 X |
| | B8 (FT) | 5 | 750 | 6.7 X |
| | C3-C8 (Protein Peak) | 6 | 900 | 6.7 X |
| | C8-D1 (Protein Peak) | 5 | 900 | 5.6 X |
| | D2-D8 (Protein Peak) | 7 | 900 | 7.8 X |
| 4th Nov. 2008 | A2 (FT) | 9.5 | 750 | 12.7 X |
| | A7 (FT) | 9.5 | 750 | 12.7 X |
| | B2-B10 (Protein Peak) | 13 | 700 | 18.6 X |
| 12th Nov. 2008 | B1 (FT) | 9.5 | 900 | 10.6 X |
| | B8-C3 (Protein Peak) | 11 | 1200 | 9.2 X |

Flow-through fractions selected for the ultra filtration were from the beginning ($B1_{161008}$ and $A2_{041108}$) and from the end of sample application ($B7_{161008}$, $B8_{161008}$, $A7_{041108}$ and $B1_{121108}$). These samples were analysed in order to see if the capacity of the column was exceeded with that particular sample amount.

Moreover, ammonium sulphate filtrates for each of the purifications were ultra filtrated and concentrated and the once concentrated flow through fractions were still further concentrated with MultiScreen plates with Ultracell-10 membrane, 10000 NMWL. The results of that concentration are presented in Table 9.

TABLE 7

Peak table from three separate HIC runs
The date of the run, peak name, retention time i.e. the volume at
which the peak reaches its top, area of the peak, and the maximum
height of the peak are given. The area of the peak was used to
estimate the amount of eluted protein in the elution fraction.

| Date | Peak name | Retention (ml) | Area (mAU*ml) | Height (mAU) | Estimated protein amount (mg) |
| --- | --- | --- | --- | --- | --- |
| 16 Oct. 2008 | Flow through fraction | 84.48 | 44814.9666 | 816.803 | |
| | Wash unbound sample | 86.54 | 4640.2506 | 659.512 | |
| | Eluted sample | 93.08 | 2923.2825 | 814.968 | 3.36 |
| 4 Nov. 2008 | Flow through fraction | 27.94 | 42450.2080 | 673.843 | |
| | Eluted sample | 87.01 | 2562.0783 | 953.277 | 2.95 |
| 12 Nov. 2008 | Flow-through fraction | 23.40 | 78004.2505 | 658.094 | |
| | Eluted protein | 152.03 | 3126.5816 | 1214.232 | 3.60 |

TABLE 9

Samples selected for ultra filtration and concentration with
MultiScreen Filter Plates with Ultracell-10 membrane, 10000 NMWL
Both the original volume and the volume of the sample after
concentration are indicated. Concentration factor was calculated
by dividing the original sample volume with the final sample volume.

| Date of purification | Selected fractions | Original volume (ml) | Final volume (µl) | Conc. factor |
|---|---|---|---|---|
| 16$^{th}$ Oct. 2008 | AS-sup 161008 | 500 | 420 | 1.2 X |
| | B1 (FT) | 400 | 125 | 3.2 X |
| | B7 (FT) | 1200 | 300 | 4.0 X |
| | B8 (FT) | 380 | 115 | 3.3 X |
| 4$^{th}$ Nov. 2008 | AS-sup 041108 | 500 | 440 | 1.1 X |
| | A2 (FT) | 360 | 115 | 3.1 X |
| | A7 (FT) | 700 | 265 | 2.1 X |
| 12$^{th}$ Nov. 2008 | AS-sup 121108 | 500 | 455 | 1.1 X |
| | B1 (FT) | 430 | 165 | 2.6 X |

The flow through fractions of the HIC runs were, thus, concentrated by a factor of 16 or more. The final concentration factors of the flow through fractions are listed in Table 10.

TABLE 10

Final concentration factors of flow through samples
The final concentration factors were calculated by multiplying
the concentration factor of the first concentration with
the concentration factor of the second concentration.

| Date of purification | Selected fractions | Conc. factor |
|---|---|---|
| 16$^{th}$ Oct. 2008 | B1 (FT) | 20.0 X |
| | B7 (FT) | 16.7 X |
| | B8 (FT) | 21.2 X |
| 4$^{th}$ Nov. 2008 | A2 (FT) | 39.1 X |
| | A7 (FT) | 35.8 X |
| 12$^{th}$ Nov. 2008 | B1 (FT) | 33.0 X |

BCA Assay Results

Results from the BCA assay are presented in Table 11. The protein concentration of the flow through fractions was measured before the last concentration step with Multi-Screen plates with Ultracell-10 membrane.

TABLE 11

Protein concentrations of HIC flow-through and peak fractions
The protein concentration was determined from two replicates
of two different dilutions of a given sample. The final
volume of the sample was measured after concentration.

| Sample name | Protein concentration in the sample (mg/ml) | Final volume of the sample (ml) | Amount of protein in the sample (mg) |
|---|---|---|---|
| B1$_{161008}$ | 0.02 | 0.75 | 0.015 |
| B8$_{161008}$ | 0.01 | 0.75 | 0.008 |
| C3-C8$_{161008}$ | 9.59 | 0.9 | 8.63 |
| C9-D1$_{161008}$ | 0.10 | 0.9 | 0.09 |
| D2-D8$_{161008}$ | 0.72 | 0.9 | 0.65 |
| Total protein amount in fractions C3-D8 | | | 9.37 |
| A2$_{041108}$ | 0.00 | 0.75 | 0.00 |
| B2-B10$_{041108}$ | 9.45 | 0.7 | 6.62 |
| B1$_{121108}$ | 0.08 | 0.9 | 0.07 |
| B8-C3$_{121108}$ | 7.56 | 1.2 | 9.07 |

Chromatograms from HIC runs gave rather high, ~700 mAU, A$_{280}$ values throughout sample application for the out coming solution. The eluted protein peaks contained sufficient amounts of protein. They were near the presumed binding capacity of the column, 10 mg. The area of the peak from the Äkta gave three times lower estimates for protein amount than the BCA assay.

SDS-PAGE

Figure 6:
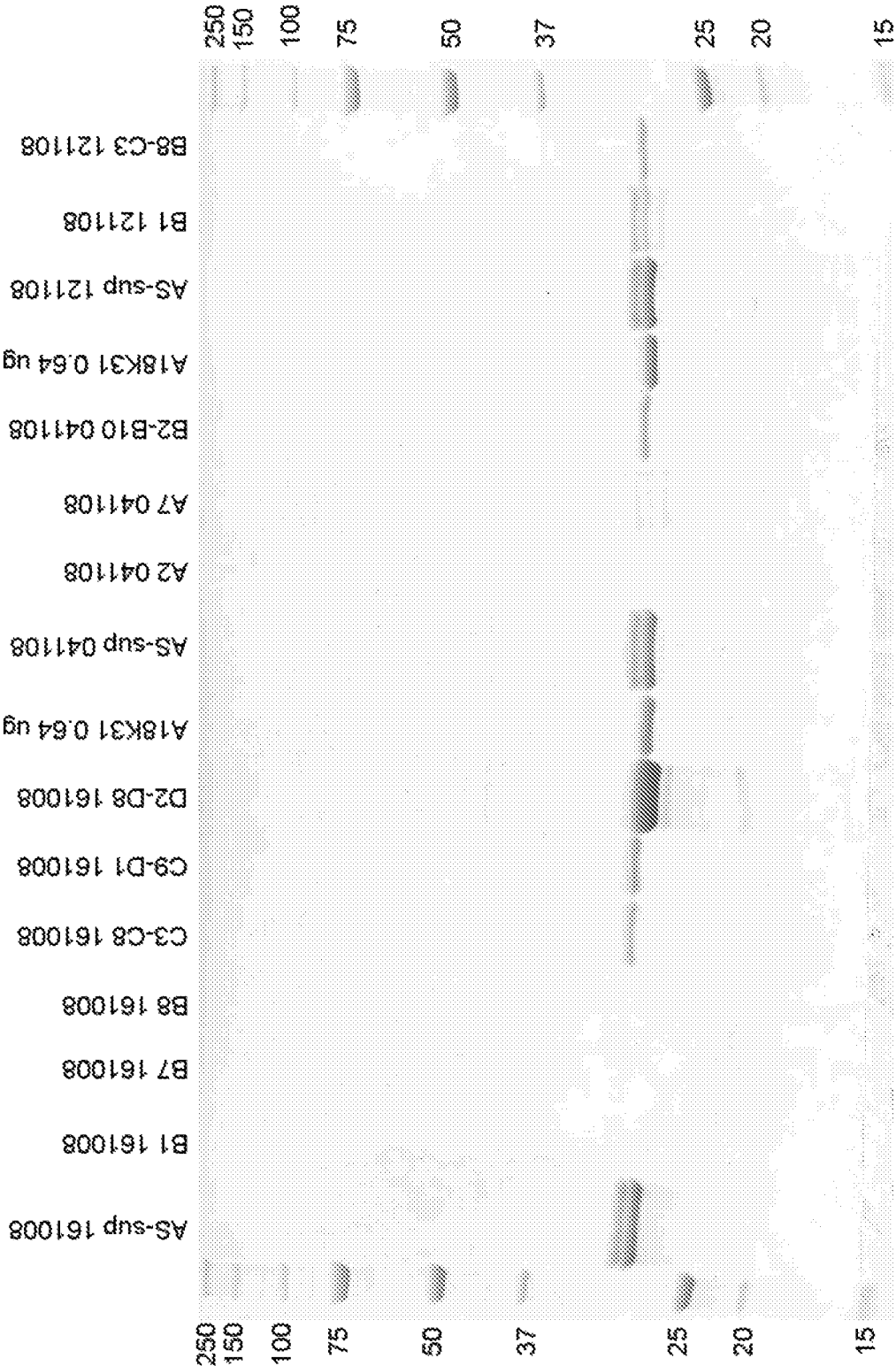
FIG. 6 shows a SDS-PAGE gel of the fractions of the three HIC purifications shown in FIGS. 3-5. AS-sup=ammonium sulphate filtrate used in the particular purification, i.e. starting material for purification. B1 161008, B7 161008, B8 161008, A2 041108, A7 041108, and B1 121108: flow through fractions of each of purifications. C3-C8 161008, C9-D1 161008, D2-D8 161008, B2-B10 041108, and B8-C3 121108: eluted protein peak, pooled fractions. A18K31 P1A: reference material, 0.64 µg/lane.

The maximum volume (17.5 µl) of sample was loaded on the SDS-PAGE (FIG. 6) for ammonium sulphate filtrates and flow through fractions, except for B1$_{121108}$ for which 6.5 µl was loaded. The volume of the samples from protein peaks was calculated so that there would be ~0.5 µg of protein per lane and assumed that all protein in the sample would be P1A derivative IS288. The SDS-PAGE is represented in FIG. 6.

Ammonium sulphate filtrate samples all contain a double band near 30 kDa (MW of IS288 is 29288 Da, and of P1A 29273 Da). The same double band accompanied by a slightly smaller extra band can be clearly seen in flow through fraction B1$_{121108}$ and somewhat more faintly in flow through fraction A7$_{041108}$. On the other hand, both of these extra bands have been removed from eluted protein peaks. Some minor impurities can be seen on the last pooled fractions of purification D2-D8 161008, when ~10 times the intended amount of protein was loaded. It can be concluded that the purified protein was the major protein form and that by molecular weight analysis it was the P1A variant IS288.

Example 4: Test of a Microbiological Screening Assay for Beta-Lactamase Activity The 50% effective inhibitory concentration (EC$_{50}$) of ampicillin and ceftriaxone against *Escherichia coli* was determined in the absence and presence of P1A β-lactamase. For the purposes of these studies, the stated effective concentration was the initial concentration of ampicillin or ceftriaxone added at the beginning of the experiment, and not a concentration measured during the course of the experiment or at the end of the incubation period. The results of the analysis are presented in Tables 12-14.

Initial evaluation utilized P1A at concentrations of 0.5 ng/mL to 5 µg/mL and ampicillin or ceftriaxone at concentrations of 0.13 µg/mL to 128 µg/mL. Addition of the lowest concentration of P1A (0.5 ng/mL) shifted the EC$_{50}$ of ampicillin from 16 µg/mL to greater than the highest test concentration of 128 µg/mL when added simultaneously and to 64 µg/mL when P1A was pre-incubated with ampicillin prior to addition of the bacteria (Table 12). Using the same concentrations of P1A with 0.13 µg/mL to 128 µg/mL of ceftriaxone, it was observed that ceftriaxone was completely inhibitory at the lowest concentration (EC$_{99}$<0.13 µg/mL) and the EC$_{50}$ of ceftriaxone was shifted to 0.25 µg/mL in the presence of 5 ng/mL P1A when added simultaneously and to 128 µg/mL when 50 ng/mL P1A was preincubated with the antibiotic. Based on this analysis, the concentrations of P1A and ceftriaxone were adjusted to bracket the inhibitory concentrations of both.

Using concentration of P1A from 5 µg/mL to 50 ng/mL with 0.13 µg/mL to 128 µg/mL of ampicillin, the EC$_{50}$ of ampicillin was shifted from 16 µg/mL in the absence of P1A to 128 µg/mL in the presence of 50 µg/mL when pre-incubated or added simultaneously. Lower concentrations of P1A (5 µg/mL) had no effect on the ampicillin EC$_{50}$. The EC$_{50}$ of ceftriaxone was shifted from 0.03 µg/mL in the absence of P1A to greater than 4 µg/mL in the presence of 50 ng/mL or greater P1A when preincubated or added simultaneously (Table 13). Lower concentrations of P1A (50 µg/mL to 5 ng/mL) had no effect on the ceftriaxone EC$_{50}$.

Results with the simultaneous addition of P1A with ampicillin or ceftriaxone were confirmed through repeat analysis (Table 14).

TABLE 12

Effective inhibitory concentration (EC$_{50}$) of ampicillin and ceftriaxone in the absence and presence of P1A determined by micro broth dilution analysis.

| P1A Concentration | Ampicillin EC$_{50}$(µg/mL) | | Ceftriaxone EC$_{50}$(µg/mL) | |
|---|---|---|---|---|
| | Pre incubation | Simultaneous | Pre incubation | Simultaneous |
| 0 | 16 | 16 | <0.13 | <0.13 |
| 0.5 ng/mL | 64 | >128 | <0.13 | <0.13 |
| 5 ng/mL | 128 | >128 | <0.13 | 0.25 |
| 50 ng/mL | >128 | >128 | >128 | >128 |
| 500 ng/mL | >128 | >128 | >128 | >128 |
| 5 µg/mL | >128 | >128 | >128 | >128 |

Antibiotics were either added to the P1A and incubated for 30 min at 37° C. (Pre-incubation) prior to addition of bacteria, or added to the plates following the addition of P1A and bacteria (Simultaneous). All concentrations and combinations were evaluated in triplicate in a 96-well plate format. Following overnight incubation, the OD$_{625}$ of the plates was measured in a Spectramax 384 plate reader and the data were imported into a customized Excel spreadsheet for the determination of the 50% effective inhibitory concentration at (EC$_{50}$) by linear regression analysis. For the purposes of these studies, the stated effective concentration is the initial concentration of ampicillin or ceftriaxone added at the beginning of the experiment, and not a concentration measured during the course of the experiment or at the end of the incubation period.

TABLE 13

Effective inhibitory concentration (EC$_{50}$) of ampicillin and ceftriaxone in the absence and presence of P1A determined by micro broth dilution analysis.

| P1A Concentration | Ampicillin EC$_{50}$(µg/mL) | | Ceftriaxone EC$_{50}$(µg/mL) | |
|---|---|---|---|---|
| | Pre incubation | Simultaneous | Pre incubation | Simultaneous |
| 0 | 16 | 16 | 0.02 | 0.02 |
| 5 pg/mL | 16 | 16 | NA | NA |
| 50 pg/mL | 128 | 128 | 0.02 | 0.02 |
| 500 pg/mL | >128 | >128 | 0.03 | 0.03 |
| 5 ng/mL | >128 | >128 | 0.03 | 0.03 |
| 50 ng/mL | >128 | >128 | >4 | >4 |
| 500 ng/mL | NA | NA | >4 | >4 |

Antibiotics were either added to the P1A and incubated for 30 min at 37° C. (Pre-incubation) prior to addition of bacteria, or added to the plates following the addition of P1A and bacteria (Simultaneous). All concentrations and combinations were evaluated in triplicate in a 96-well plate format. Following overnight incubation, the OD$_{625}$ of the plates was measured in a Spectramax 384 plate reader and the data were imported into a customized Excel spreadsheet for the determination of the 50% effective inhibitory concentration (EC$_{50}$).

TABLE 14

Effective inhibitory concentration (EC$_{50}$) of ampicillin and ceftriaxone in the absence and presence of P1A determined by microbroth dilution analysis.

| P1A Concentration | Ampicillin EC$_{50}$(µg/mL) Simultaneous | Ceftriaxone EC$_{50}$(µg/mL) Simultaneous |
|---|---|---|
| 0 | 16 | 0.03 |
| 5 pg/mL | 16 | NA |
| 50 pg/mL | 128 | 0.03 |
| 500 pg/mL | >128 | 0.03 |
| 5 ng/mL | >128 | 0.03 |
| 50 ng/mL | >128 | >4 |
| 500 ng/mL | NA | >4 |

Antibiotics were added to the P1A bacteria (Simultaneous). All concentrations and combinations were evaluated in triplicate in a 96-well plate format. Following overnight incubation, the OD$_{625}$ of the plates was measured in a Spectramax 384 plate reader and the data were imported into a customized Excel spreadsheet for the determination of the 50% effective inhibitory concentration at (EC$_{50}$) by linear regression analysis.

These results demonstrated that P1A effectively inhibited the activity of ampicillin and ceftriaxone in an in vitro microbiological assay and indicated that P1A is 1,000-fold more active against ampicillin than ceftriaxone in the microbiological assay.

Next, the 90% effective inhibitory concentration (EC$_{90}$) of ampicillin, ceftriaxone, ceftazidime, meropenem, cefepime, cefazolin, amp/sulbactam, cefoperazone, cefotaxime, and cefuroxime against *Escherichia coli* was determined in the absence and presence of P1A, P3A, or P4A β-lactamase. For the purposes of these studies, the stated effective concentration was the initial concentration of ampicillin, ceftriaxone, ceftazidime, meropenem, cefepime, cefazolin, amp/sulbactam, cefoperazone, cefotaxime, and cefuroxime added at the beginning of the experiment, and not a concentration measured during the course of the experiment or at the end of the incubation period. The results of the analysis are presented in Tables 15-17. Each box in the below tables (Tables 15-17) has two numbers separated by a slash—the two numbers are duplicate assays, all of which showed tight agreement.

Specifically, the assay was performed by diluting (2-fold steps) the chosen antibiotic across the rows of a 96 well dish. The MIC was determined as the point at which the diluted antibiotic transitions from killing to not killing the bacteria (in this case, an *E. coli* strain that is sensitive to all antibiotics). P1A, P3A, and P4A were diluted (10 fold steps) down the columns (the β-lactamase concentrations increased down the columns). As the β-lactamase concentration increased, it reached a level at which it degraded the antibiotic sufficiently to alter the apparent MIC reading (the MIC didn't actually change, but it appeared to change because the amount of antibiotic remaining in the well was less that the amount loaded into the well). In most cases, there were two break points, the first in which the MIC appeared to increase a bit, and then at ten-fold concentration higher where the MIC exceeded the maximum amount of antibiotic tested. The latter point was used as the cut-off point. It is important to note that with this *E. coli*, the MIC was different for each antibiotic. However, for this assay, the absolute MIC is not the most important parameter. The most relevant readout was the β-lactamase concentration at which the apparent MIC increases to the maximum amount of antibiotic tested.

When the cut-off point occurred at low β-lactamase concentration, this implied that the β-lactamase was potent at degrading that antibiotic. When it took a lot of β-lactamase to move the MIC, then the β-lactamase was relatively weak for that antibiotic. This assay was designed, without wishing to be bound by theory to provide predictions of in vivo efficacy for each β-lactamase for a given antibiotic. These data can be combined with the in vitro kinetic data.

TABLE 15

Antibiotic activity of ampicillin and ceftriaxone in the presence of bacterial culture supernatants from *bacillus* strains expressing soluble β-lactamase proteins P1A (RS310), P3A (IS118), or P4A (IS288).

| | Ampicillin $EC_{90}$(µg/mL) | | Ceftriaxone $EC_{90}$(µg/mL) | |
|---|---|---|---|---|
| | Rep 1 | Rep 2 | Rep 1 | Rep 2 |
| RS310 Concentration | | | | |
| 0 | 2 | 4 | 0.008 | 0.02 |
| 5 pg/mL | 4 | 16 | NA | NA |
| 50 pg/mL | 32 | 128 | 0.008 | 0.008 |
| 500 pg/mL | >128 | >128 | 0.008 | 0.008 |
| 5 ng/mL | >128 | >128 | 0.06 | 0.008 |
| 50 ng/mL | >128 | >128 | >4 | >4 |
| 500 ng/mL | NA | NA | >4 | >4 |
| IS118 Concentration | | | | |
| 0 | 2 | 4 | 0.008 | 0.02 |
| 5 pg/mL | 4 | 8 | NA | NA |
| 50 pg/mL | 16 | 64 | 0.008 | 0.008 |
| 500 pg/mL | >128 | >128 | 0.5 | 0.06 |
| 5 ng/mL | >128 | >128 | NA | >4 |
| 50 ng/mL | >128 | >128 | >4 | >4 |
| 500 ng/mL | NA | NA | >4 | >4 |
| IS288 Concentration | | | | |
| 0 | 2 | 4 | 0.02 | 0.02 |
| 5 pg/mL | 2 | 16 | NA | 0.03 |
| 50 pg/mL | 4 | 32 | 0.5 | 0.13 |
| 500 pg/mL | 64 | 128 | >4 | 4 |
| 5 ng/mL | >128 | >128 | >4 | >4 |
| 50 ng/mL | >128 | >128 | >4 | >4 |
| 500 ng/mL | NA | NA | >4 | NA |

*E. coli* 29522 was incubated overnight in the presence of serial dilutions of antibiotic and the indicated amounts of P3-lactamase protein from cell culture supernatants in a 96 well plate. Bacterial density ($OD_{625}$) of the cultures was measured and the concentration at which the density was reduced by 90% relative to an untreated bacterial control ($EC_{90}$) was determined. The assay was performed on two separate days and the data reported as Rep1 and Rep2. NA=not assayed.

TABLE 16

Antibiotic activity of ceftazidime, meropenem, cefepime, and ceftriazone in the presence of bacterial culture supernatants from *bacillus* strains expressing soluble β-lactamase proteins P1A (RS310), P3A (IS118), or P4A (IS288).

| | Ceftazidime $EC_{90}$ (µg/mL) (high test 4 µg/mL) | Meropenem $EC_{90}$ (µg/mL) (high test 1 µg/mL) | Cefepime $EC_{90}$ (µg/mL) (high test 2 µg/mL) | Ceftriazone $EC_{90}$ (µg/mL) (high test 1 µg/mL) |
|---|---|---|---|---|
| RS310 Concentration | | | | |
| 0 | 0.13/0.5 | 0.06/0.06 | 0.06/0.03 | 0.06/0.06 |
| 50 pg/mL | 0.25/0.25 | 0.06/0.03 | 0.01/0.03 | 0.06/0.06 |
| 500 pg/mL | 0.13/0.25 | 0.06/0.06 | 0.06/0.06 | 0.06/0.13 |
| 5 ng/mL | 0.13/0.25 | 0.06/0.06 | 0.13/0.25 | 0.25/1.0 |
| 50 ng/mL | 0.5/0.5 | 0.03/0.06 | >2.0/>2.0 | >1.0/>1.0 |
| 500 ng/mL | >4.0/>4.0 | 0.03/0.03 | >2.0/>2.0 | >1.0/>1.0 |
| IS118 Concentration | | | | |
| 0 | 0.13/0.13 | 0.06/0.03 | 0.06/0.03 | 0.06/0.06 |
| 5 pg/mL | 0.13/0.25 | 0.06/0.03 | 0.03/0.03 | 0.06/0.13 |
| 50 pg/mL | 0.25/0.25 | 0.06/0.03 | 0.06/0.03 | 1.0/0.25 |
| 5 ng/mL | 0.13/0.25 | 0.06/0.06 | 0.13/0.13 | >1.0/>1.0 |
| 50 ng/mL | 1.0/2.0 | 0.03/0.06 | >2.0/>2.0 | >1.0/>1.0 |
| 500 ng/mL | >4.0/>4.0 | 0.06/0.06 | >2.0/>2.0 | >1.0/>1.0 |
| IS288 Concentration | | | | |
| 0 | 0.13/0.5 | 0.06/0.06 | 0.03/0.03 | 0.06/0.06 |
| 50 pg/mL | 0.25/0.25 | 0.06/0.03 | 0.03/0.03 | 0.13/>1.0 |
| 500 pg/mL | 0.13/0.25 | 0.06/0.03 | 0.06/0.06 | >1.0/>1.0 |
| 5 ng/mL | 0.25/0.5 | 0.03/0.03 | 0.25/0.25 | >1.0/>1.0 |
| 50 ng/mL | >4.0/>4.0 | 0.03/0.06 | >2.0/>2.0 | >1.0/>1.0 |
| 500 ng/mL | >4.0/>4.0 | 0.06/0.06 | >2.0/>2.0 | >1.0/>1.0 |

*E. coli* 29522 was incubated overnight in the presence of serial dilutions of antibiotic and the indicated amounts of P3-lactamase protein from cell culture supernatants in a 96 well plate. Bacterial density ($OD_{625}$) of the cultures was measured and the concentration at which the density was reduced by 90% relative to an untreated bacterial control (EC90) was determined. The assay was performed on two separate days and the data reported as two numeric values separated by a slash. NA=not assayed.

TABLE 17

Antibiotic activity of cefazolin, amp/sublactam, cefoperazone, cefotaxime, cefuroxime, and ceftriaxone in the presence of bacterial culture supernatants from *bacillus* strains expressing soluble β-lactamase proteins P1A (RS310), P3A (IS118), or P4A (IS288).

| | Cefazolin $EC_{90}$ (µg/mL) (high test 64 µg/mL) | Amp: Sublactam $EC_{90}$ (µg/mL) (high test 128:64 µg/mL) | Cefoperazone $EC_{90}$ (µg/mL) (high test 8 µg/mL) | Cefotaxime EC90 (µg/mL) (high test 2 µg/mL) | Cefuroxime $EC_{90}$ (µg/mL) (high test 128 µg/mL) | Ceftriaxone $EC_{90}$ (µg/mL) (high test 1 µg/mL) |
|---|---|---|---|---|---|---|
| RS310 Concentration | | | | | | |
| 0 | 2.0/2.0 | 4.0:2.0/4.0:2.0 | 0.25/0.13 | 0.004/0.008 | 4.0/4.0 | 0.03/0.03 |
| 50 pg/mL | 2.0/4.0 | 4.0:2.0/8.0:4.0 | 0.5/0.25 | 0.008/0.004 | 4.0/2.0 | 0.03/0.06 |

TABLE 17-continued

Antibiotic activity of cefazolin, amp/sublactam, cefoperazone, cefotaxime, cefuroxime, and ceftriaxone in the presence of bacterial culture supernatants from *bacillus* strains expressing soluble β-lactamase proteins P1A (RS310), P3A (IS118), or P4A (IS288).

|  | Cefazolin $EC_{90}$ (μg/mL) (high test 64 μg/mL) | Amp: Sublactam $EC_{90}$ (μg/mL) (high test 128:64 μg/mL) | Cefoperazone $EC_{90}$ (μg/mL) (high test 8 μg/mL) | Cefotaxime EC90 (μg/mL) (high test 2 μg/mL) | Cefuroxime $EC_{90}$ (μg/mL) (high test 128 μg/mL) | Ceftriaxone $EC_{90}$ (μg/mL) (high test 1 μg/mL) |
|---|---|---|---|---|---|---|
| 500 pg/mL | 16/16 | 4.0:2.0/4.0:2.0 | 2.0/4.0 | 0.004/0.004 | 4.0/4.0 | 0.13/0.13 |
| 5 ng/mL | >64/>64 | 8.0:4.0/16:8.0 | >8.01 >8.0 | 0.008/0.008 | 32/32 | 0.13/0.13 |
| 50 ng/mL | >64/>64 | 32:16/32:16 | >8.01 >8.0 | 1.0/0.25 | >128/>128 | >1.01 >1.0 |
| 500 ng/mL | >64/>64 | 128:64/128:64 | >8.01 >8.0 | >2.01 >2.0 | >128/>128 | >1.01 >1.0 |
| IS118 Concentration | | | | | | |
| 0 | 2.0/2.0 | 4.0:2.0/4.0:2.0 | 0.25/0.25 | 0.004/0.004 | 2.0/4.0 | 0.03/0.03 |
| 50 pg/mL | 4.0/4.0 | 4.0:2.0/8.0:4.0 | 0.5/0.5 | 0.004/0.004 | 8.0/4.0 | 0.13/0.13 |
| 500 pg/mL | 64/64 | 4.0:2.0/4.0:2.0 | 8.0/>8.0 | 0.008/0.008 | 8.0/8.0 | 0.25/0.5 |
| 5 ng/mL | >64/>64 | 8.0:4.0/16:8.0 | >8.01 >8.0 | 0.06/0.3 | 128/128 | >1.01 >1.0 |
| 50 ng/mL | >64/>64 | 32:16/32:16 | >8.01 >8.0 | >2.01 >2.0 | >128/>128 | >1.01 >1.0 |
| 500 ng/mL | >64/>64 | 128:64/128:64 | >8.01 >8.0 | >2.01 >2.0 | >128/>128 | >1.01 >1.0 |
| IS288 Concentration | | | | | | |
| 0 | 2.0/2.0 | 4.0:2.0/4.0:2.0 | 0.25/0.13 | 0.004/0.004 | 4.0/2.0 | 0.03/0.06 |
| 50 pg/mL | 4.0/4.0 | 4.0:2.0/4.0:4.0 | 0.5/0.5 | 0.02/0.008 | 8.0/8.0 | 0.25/0.25 |
| 500 pg/mL | >64/>64 | 4.0:2.0/4.0:2.0 | >8.01 >8.0 | 0.25/0.25 | 32/32 | >1.01 >1.0 |
| 5 ng/mL | >64/>64 | 4.0:2.0/8.0:4.0 | >8.01 >8.0 | >2.01 >2.0 | >128/>128 | >1.0/>1.0 |
| 50 ng/mL | >64/>64 | 8.0:4.0/8.0:4.0 | >8.0/>8.0 | >2.0/>2.0 | >128/>128 | >1.01 >1.0 |
| 500 ng/mL | >64/>64 | 32:16/32:16 | >8.0/>8.0 | >2.0/>2.0 | >128/>128 | >1.0/>1.0 |

*E. coli* 29522 was incubated overnight in the presence of serial dilutions of antibiotic and the indicated amounts of IR-lactamase protein from cell culture supernatants in a 96 well plate. Bacterial density (OD625) of the cultures was measured and the concentration at which the density was reduced by 90% relative to an untreated bacterial control (EC90) was determined. The assay was performed on two separate days and the data reported as two numeric values separated by a slash. NA=not assayed.

Without wishing to be bound by theory, these data suggest more activity in vitro than predicted from the corresponding kinetic data. For example, the ceftazidime kinetic data predicted a lack of therapeutic efficacy, but these data showed activity at 500 ng/ml with a 10-fold improvement for P4A. Next, it was observed that P1A and P3A were quite effective for ampicillin, while P4A lost some activity for ampicillin. The amp/sulbactam data verified that sulbactam effectively inhibited P1A, P3A, and P4A. Whereas the amp/sulbactam data verified that sulbactam is an effective β-lactamase inhibitor, this should not be interpreted to mean that these beta-lactamases will not be efficacious in vivo. Specifically, if the pharamokinetics for biliary excretion are different for the antibiotic and the inhibitor, then the antibiotic can be found in the small intenstine in the absence of its inhibitor. For example, P1A has been shown to be efficacious in humans with piperacillin/tazobactam. The meropenem data confirmed what was expected, that the P1A, P3A, and P4A β-lactamases are penicillinases and cephalosporinases. Finally, P4A was observed to be remarkably effective at degrading ceftriaxone, better than P3A. P4A was as good for ceftriaxone as it was for ampicillin. P4 also had improved activity for several important cephalosporins with the exception of cefepime. In comparison to P1A, P4A exhibited about 10-fold or greater β-lactamase activity for ceftriaxone, cefotaxime, ceftazidime, cefazolin, cefoperazone, and cefurxine.

Example 5: Analysis of the Antibiotic Degradation Properties of P1A, P3A, and P4A P1A and P4A were screened for degradation of ampicillin, ceftriazone, cefotaxime, cefozolin, cefuroxime, cefoperazone, cefepime, and ceftazidime in a microtiter plate activity assay that was designed to mimic the activity of the beta-lactamases in the gut in the presence of high antibiotic concentrations. The assay was performed by mixing 10, 100 or 1000 μg/ml of the indicated antibiotics with P1A or P4A, at concentrations of 10 or 100 ng/ml. Plates were either incubated for one hour at 37° C. after which *E. coli* (ATCC 25922) was added, or *E. coli* was added immediately after the addition of the beta-lactamase enzymes. The plates were incubated overnight and the bacterial growth quantified by measuring the absorbance at 625 nm ($OD_{625}$) in a Spectramax 384 Plus plate reader. The analysis was performed twice for each beta-lactamase and antibiotic. The beta-lactamase activity of the culture supernatants was determined as positive or negative based on the appearance of bacterial growth in the individual wells. An $OD_{625}$ of 1.0 or greater indicated maximal bacterial growth, therefore complete antibiotic degradation and high beta-lactamase activity. An $OD_{625}$ of less than 1.0 indicated low bacterial growth therefore incomplete antibiotic degradation, hence low beta-lactamase activity.

Figure 8:
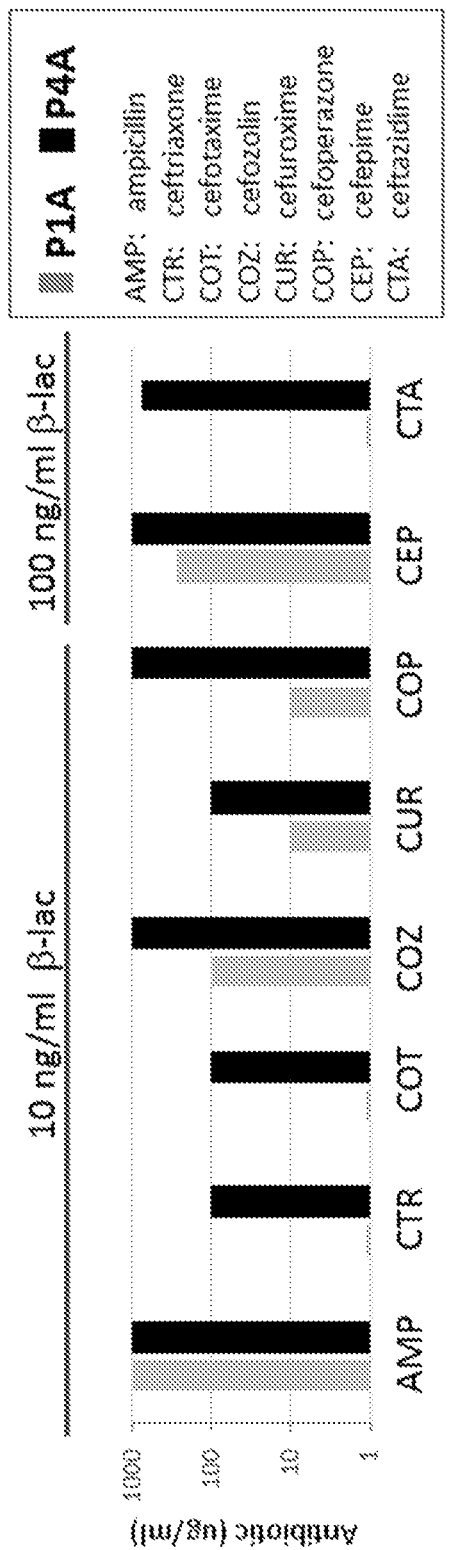

Results from the analysis are shown in FIG. 8. There was no difference in the readings obtained for the plates that were preincubated with the beta-lactamase and antibiotic compared to the plates that did not undergo preincubation.

For all antibiotics, except ampicillin, P4A showed improved activity relative to P1A. P1A showed no activity for ceftriaxone, cefotaxime, and ceftazidime. P4A shows greater efficacy for cefotaxime, cefozolin, cefoperazone, cefepime, and ceftazidime.

Accordingly, modification of five (P4A) amino acids in P1A boosted cephalosporinase activity 10-1000-fold. Oral administration of P4A can therefore protect the gut flora from commonly used cephalosporins and extend the clinical utility of this prophylactic strategy to the prevention of, for example, CDI. Specifically, the assays presented herein show that, at concentrations that should be readily achievable in the small intestine, P4A can degrade cephalosporins and other antibiotics and have an improved substrate profile relative to P1A.

Definitions

The following definitions are used in connection with the invention disclosed herein. Unless defined otherwise, all technical and scientific terms used herein have the same meaning as commonly understood to one of skill in the art to which this invention belongs.

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

An "effective amount," when used in connection with medical uses is an amount that is effective for providing a measurable treatment, prevention, or reduction in the rate of pathogenesis of a disease of interest.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g. inventive β-lactamases and/or pharmaceutical compositions (and/or additional agents) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. For example, administration of therapeutic agents to a patient suffering from a GI tract disorder (e.g. CDI) provides a therapeutic benefit not only when the underlying condition is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. In certain embodiments, the effect will result in a quantifiable change of two-fold, or three-fold, or four-fold, or five-fold, or ten-fold. Therapeutic benefit also includes halting or slowing the progression of the underlying disease or disorder or reduction in toxicity, regardless of whether improvement is realized.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A beta-lactamase comprising an amino acid sequence having at least 95% sequence identity with SEQ ID NO: 1 and the following mutations according to Ambler classification:
    an aliphatic hydrophobic residue other than alanine (A) at position 232,
    a polar and neutral hydrophilic residue other than alanine (A) at position 237,
    an aliphatic hydrophobic residue other than alanine (A) at position 238,
    a polar and negative hydrophilic residue other than serine (S) at position 240, and
    a polar and neutral hydrophilic residue other than (R) at position 244.

2. The beta-lactamase of claim 1, wherein the beta-lactamase has a further mutation of a polar and positive hydrophilic residue other than aspartate (D) at position 276 according to Ambler classification.

3. The beta-lactamase of claim 1, wherein the aliphatic hydrophobic residue is selected from glycine (G), leucine (L), isoleucine (I), methionine (M), and valine (V).

4. The beta-lactamase of claim 1, wherein the polar and neutral hydrophilic residue is selected from asparagine (N), glutamine (Q), serine (S), threonine (T), proline (P), and cysteine (C).

5. The beta-lactamase of claim 1, wherein the polar and negative hydrophilic residue is selected from aspartate (D) and glutamate (E).

6. The beta-lactamase of claim 2, wherein the polar and positive hydrophilic residue is selected from arginine (R) and lysine (K).

7. A polynucleotide comprising a polynucleotide sequence encoding the beta-lactamase of claim 1.

8. A host cell comprising the polynucleotide of claim 7.

9. A pharmaceutical composition, comprising the beta-lactamase of claim 1 and a pharmaceutically acceptable carrier or excipient.

10. The pharmaceutical composition of claim 9, wherein the pharmaceutical composition is formulated for oral administration, optionally selected from a tablet, multi-particulate sprinkle, and a multi-particulate capsule.

11. A method for preventing an antibiotic-induced adverse effect in the gastrointestinal (GI) tract, comprising administering an effective amount of a beta-lactamase to a patient in need thereof, wherein the beta-lactamase comprises an amino acid sequence having at least 95% sequence identity with SEQ ID NO: 1 and the following mutations according to Ambler classification:
- an aliphatic hydrophobic residue other than alanine (A) at position 232,
- a polar and neutral hydrophilic residue other than alanine (A) at position 237,
- an aliphatic hydrophobic residue other than alanine (A) at position 238,
- a polar and negative hydrophilic residue other than serine (S) at position 240, and
- a polar and neutral hydrophilic residue other than (R) at position 244.

12. The method of claim 11, wherein the beta-lactamase has a further mutation of a polar and positive hydrophilic residue other than aspartate (D) at position 276 according to Ambler classification.

13. The method of claim 11, wherein the aliphatic hydrophobic residue is selected from glycine (G), leucine (L), isoleucine (I), methionine (M), and valine (V).

14. The method of claim 11, wherein the polar and neutral hydrophilic residue is selected from asparagine (N), glutamine (Q), serine (S), threonine (T), proline (P), and cysteine (C).

15. The method of claim 11, wherein the polar and negative hydrophilic residue is selected from aspartate (D) and glutamate (E).

16. The method of claim 12, wherein the polar and positive hydrophilic residue is selected from arginine (R) and lysine (K).

17. The method of claim 11, wherein the subject is being administered or will be administered an antibiotic.

18. The method of claim 11, wherein the antibiotic-induced adverse effect in the gastrointestinal (GI) tract is selected from *C. difficile* infection (CDI), *C. difficile*-associated disease, and antibiotic-associated diarrhea (AAD).

* * * * *